(12) United States Patent
Reboud-Ravaux et al.

(10) Patent No.: US 7,919,468 B2
(45) Date of Patent: Apr. 5, 2011

(54) COMPOUNDS USEFUL AS MODULATORS OF THE PROTEASOME ACTIVITY

(75) Inventors: Michèle Claude Yvonne Reboud-Ravaux, Paris (FR); Joëlle Vidal, Rennes (FR); Sandrine Piguel, Massy (FR); Nicolas Basse, Saint Jean de Braye (FR); Alexandra Ferrier-Berthelot, la Bergiere (FR); Maurice Pagano, Limours (FR)

(73) Assignees: Centre National de la Recherche Scientifique (C.N.R.S.), Paris (FR); Universite Pierre et Marie Curie, Paris (FR)

( * ) Notice: Subject to any disclaimer, the term of this patent is extended or adjusted under 35 U.S.C. 154(b) by 103 days.

(21) Appl. No.: 11/918,060

(22) PCT Filed: Dec. 22, 2005

(86) PCT No.: PCT/EP2005/013893
§ 371 (c)(1),
(2), (4) Date: Oct. 9, 2007

(87) PCT Pub. No.: WO2006/105811
PCT Pub. Date: Oct. 12, 2006

(65) Prior Publication Data
US 2009/0069222 A1    Mar. 12, 2009

Related U.S. Application Data

(60) Provisional application No. 60/668,946, filed on Apr. 7, 2005.

(51) Int. Cl.
A61K 38/06 (2006.01)
A61K 38/12 (2006.01)
C07K 5/087 (2006.01)

(52) U.S. Cl. ............... 514/20.1; 514/21.1; 514/21.9; 530/331

(58) Field of Classification Search ............ None
See application file for complete search history.

(56) References Cited

FOREIGN PATENT DOCUMENTS

| EP | 0 248 231 | 12/1987 |
| EP | 0 818 462 | 1/1998 |
| EP | 0 832 900 | 4/1998 |
| WO | WO 02/081501 | 10/2002 |

OTHER PUBLICATIONS

J. Adams. Potential for proteasome inhibition in the treatment of cancer. Drug Discovery Today. Apr. 2003, vol. 8, No. 7, pp. 307-315.*
Berthelot, Alexandra et al:, "Synthesis of Macrocyclic Peptide Analogues of Proteasome Inhibitor TMC-95A" Journal of Organic Chemistry, 68(25) 9835-9838 Coden: JOCAH; ISSN: 0022-3263, 2003, XP002395076.
Kim Hanyoung et al:, "Solid-Phase Synthesis of Kojic Acid-Tripeptides and Their Tyrosinase Inhibitory Activity, Storage Stability, and Toxicity" Bioorganic & Medicinal Chemistry Letters, 14(11), 2843-2846 Coden:BMCLE8; ISSN: 0960-894X, 2004, XP002395077,. Abstract, Figure 1.
Koenig, Stephan et al:, "Dimerization Inhibitors of HIV-A Protease: Synthesis and Inhibitory Activity of Modified Peptides", Innovations and Perspectives in Solid Phase Synthesis & Combinatorial Libraries: Peptides, Proteins and Nucleic Acids—Small Molecule Organic Chemistry Diversity, Collected Papers, International Symposium, 7th Southampton, United Kingdom, Sep. 18-22, 2002, XP008065950 See Table 1.
Schramm H J et al:, The Inhibition of Human Immunodeficiency Virus Protease by Interface Peptides:, Antiviral Research, Elsevier Science BV., Amsterdam, NL, vol. 30, No. 2/3, 1996 pp. 155-170, XP000984896, ISSN: 0166-3542, Abstract; Table 1.
Kaiser Markus et al:, "The Core Structure of TMC-95A is a Promising Lead for Reversible Proteasome Inhibition", Angewandte Chemie, International Edition, 41(5), 780-783, Coden: ACIFEF5; ISSN: 1433-7851, 2002, XP002395078.
Kaiser, Markus et al:, "Binding Mode of TMC-95A Analogues to Eukaryotic 20S Proteasome", Chembiochem, 5(9), 1256-1266 Coden:, CBCHFX; ISSN: 1439-4227, 2004, XP002395079.
Kaiser, Markus et al:, "TMC-95A Analogues With Endocyclic Biphenyl Ether Group as Proteasome Inhibitors", Chemistry & Biodiversity, 1(1), 161-173 Coden: CBHIAM; ISSN: 1612-1872, 2004, XP008065954.

(Continued)

*Primary Examiner* — Jeffrey E Russel
(74) *Attorney, Agent, or Firm* — Young & Thompson

(57) ABSTRACT

Compounds of the following general formula (I):

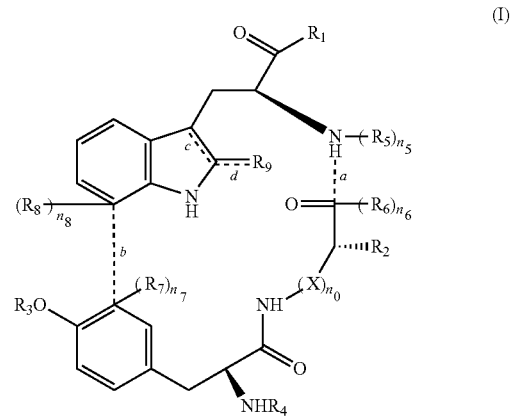

are provided. The compounds can be used as modulators of the proteasome activity, in the preparation of a medicament useful for the prevention or treatment of diseases wherein the proteasome is involved, such as diseases of inflammatory processes, various hematological and solid tumor cancers, immunological and autoimmune diseases, cardiac pathologies, myopathies, AIDS, cystic fibrosis, Alzheimer's and Parkinson's disease, or in the preparation of cosmetic compositions or phytosanitary compositions.

12 Claims, 4 Drawing Sheets

OTHER PUBLICATIONS

Kaiser, Markus et al:, "Synthesis of a TMC-95A Ketomethylenen Analogue by Cyclization Via Intromolecular Suzuki Coupling", Organic Letters, 5(19), 3435-3437 Coden: ORLEF7; ISSN: 1523-7060, 2003-XP002395080.

Kaiser, Markus et al:, "Synthesis of TMC-95A Analouges. Sturcture-Baseed Predicitonof Cyclization Propensities of Linear Precursors", Letters in Peptide Science, Volume Date 2002, 9)2-3), 65-70 Coden: LPSCEM; ISSN: 0929-5666, 2003, XP002395081.

Takashi T et al:, "Structure-Activity Relation of Lwamide Peptides Synthesized With a Multipeptide Synthesizer", Peptide Chemistry, Mino, Osaka, JP, 1996, pp. 193-196, XP002229806, ISSN: 0388-.3698 Table 2.

Rousseau, Patrice et al:, "Mechanism of Action of the .Alpha -Amylase Inhibitor (.Alpha.-AI1) of Kidney Bean: Use of Synthetic Peptides to Detect Regions of .Alpha.AI1 Interactiong With Pig Pancreatic .Alpha.-Amylase (PPA)", Cost 98: Effects of Antinutrients on the Nutritional Value of Legume Diets, Proceedings of the Scientific Workshop, $2^{nd}$, $3^{rd}$, Budapest, Aberdeen UK, and Gozd Martuljek, Slovenia, 1995 and 1996, Meeting Date 1995, vol. 2, 13-16. Editor(s): Bardoc, 1996, XP008065957.

Salvadori, Sevvero et al:, "PHE3-Substituted Analogs of Deltorphin C. Spatial Conformation and Topography of the Aromatic Ring in Peptide Recognition by .Delta. Opiod Receptors", Journal of Medicinal Chemistryk, 36 (24), 3748-56 Coden: JMCMAR; ISSN: 0022-2623, 1993, XP002395082.

Vavrek, Raymond J. et al:, "Selectivity of Minimum Sturcture Enkephalins", Life Sciences, 31(20-21)M 2249-52 Coden: LIFSAK; ISSN: 0024-3205, 1982 XP002395083 Abstract; Compounds 8,25,26,28.

* cited by examiner peptide aldehyde

MG132: Z-Leu-Leu-Leu-H
others:
PSI: Z-Ile-Glu(OtBu)-Ala-Leu-H (SEQ ID NO: 1)
MG115: Z-Leu-Leu-nVal-nNVa-H
MG101: Ac-Leu-Leu-Nle-H peptide boronates

PS-341 or bortezomib or Velcade® peptide vinyl sulfones

NL₃VS

Epoxomycin

Eponemycin epigallocatechin-3-gallate lactacystin     clasto-lactacystin

COMPOUNDS USEFUL AS MODULATORS OF THE PROTEASOME ACTIVITY

The present invention relates to compounds active as modulators (inhibitors or activators) of the proteasome activity in mammals, including man, to their process for their preparation, and to their uses for the treatment of pathologies involving the proteasome.

The ubiquitin-proteasome system is the major pathway of proteolysis in eukaryotic cells (Ciechanover, A. *EMBO J.,* 1998, 17, 7151-7160). The eukaryotic proteasome 26S (2.4 MDa) is a multicatalytic protease consisting of a 20S proteolytic core particle and a 19S regulatory subunit at either or both ends (Groll, M.; Huber, R. *Int. J. Biochem. Cell Biol.* 2003, 35, 606). The multifunctional complex is composed of at least 44 polypeptides and has unique properties. Among them, we can point out the 6 active sites (two of chymotryptic-, two of tryptic- and two of caspase-like activities) which are segregated in a secluded compartment which favours a processive degradation of proteins. Proteasome is also a N-terminal threonine hydrolase. Proteasome 26S recognizes polyubiquinated protein and is ATP-dependent. Mammalian cells contain another regulatory complex that associates with the 20S proteasome: the 11S regulator or PA28 which promotes the production of antigenic peptides. The 20S proteasome degrades oxidized proteins (Davies K. J. A. *Biochimie,* 2001, 301-310) and also an increasing amount of non ubiquitinylated proteins such as the proto-oncogenic c-Fos protein (Bossis G., Frerrar P., Acquaviva C., Jariel-Encontre I., Piechaczyk M. *Mol. Cell. Biol.* 2003, 23, 7425-7436).

Proteasomes are found in both the nucleus and the cytoplasm of eukaryotic cells. In the cytoplasm, proteasomes localize near centrosomes, on the outer surface of the endoplasmic reticulum and in cytoskeletal networks.

In addition to removing of damaged and unneeded proteins, proteasome degrades key regulatory proteins, which are crucial for many intracellular processes, including cell progression, apoptosis, NF-κB activation and antigen presentation (Coux, O.; Tanaka, K.; Goldberg, A. L. *Annu. Rev. Biochem.* 1996, 65, 801-847; Ciechanover, A. *EMBO J.,* 1998, 17, 7151-7160). Many proteasome substrates are known mediators of pathways that are dysregulated with neoplasia (Adams J. *Cancer Cell* 2003, 5, 417-421; Adams J. *Nature Reviews/Cancer* 2004, 4, 349-359). Proteasome affects cell-cycle progression by regulating the cyclins, and increasing or decreasing the apoptotic activity through effects on caspases, Bcl2 activity and nuclear factor NF-κB.

Remarkably, an empirical finding is that malignant cells are more susceptible to certain proteasome inhibitors than normal cells: reversal or bypass of some of the effects of the mutations in cell-cycle and apoptotic checkpoints that have led to tumorigenesis; higher dependency of malignant cells to proteasome system to remove aberrant proteins, dependence of some tumors to maintain drug or radiation resistance (Adams J. *Nature Reviews/Cancer* 2004, 4, 349-359; Boccadoro M., Morgan G., Canevagh J.) *Cancer Cell Intern.* 2005, 5:18; doi:10..1186/1475-2867-5-18).

Among natural and synthetic proteasome inhibitors (their structures are precisely described below), only two compounds are in clinical development: Velcade® (bortezomib, or PS341) in cancer and PS-519 in inflammation. In addition to direct apoptotic effects, proteasome inhibitors are reported to enhance sensitivity to standard chemotherapy, radiation therapy or immunotherapy, and to overcome drug resistance. NF-κB is activated by radiotherapy and chemotherapy in malignant tissues and proteasome inhibition blocks NF-κB activation by preventing proteasomal degradation of IκB (Cusak. Jr et al. *Cancer Res.,* 2001, 61, 3535-3540).

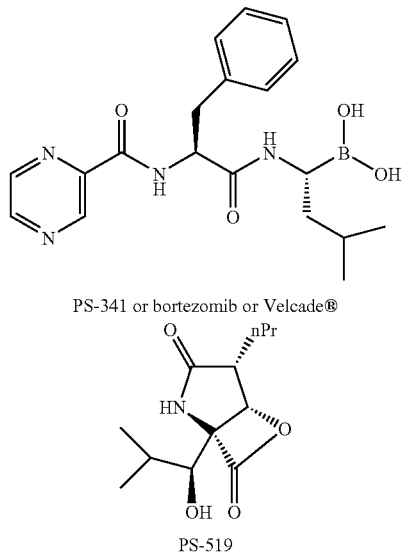

PS-341 or bortezomib or Velcade®

PS-519

Bortezomib is the first proteasome inhibitor to be approved for the treatment of multiple myeloma based on several types of data: direct inhibition of cancer cells, interference with the adhesion of multiple myeloma cells to bone marrow stroma cells and with production Il-6 in the bone marrow, anti-angiogenic properties (Adams J. *Cancer Cell* 2003, 5, 417-421).

Bortezomib is administered as cyclical therapy (twice-weekly treatment for 2 weeks every 3 weeks). Proteasome activity is maximally inhibited over 1 h after dosing (Orlowski R Z et al. *J. Clin. Oncol.* 2002, 20, 4420-4427). Adverse events have been reported in 30% patients enrolled in clinical trials (thrombocytopaenia, fatigue, peripheral neuropathy and neutropenia). Trials are in progress to investigate the use of bortezomib alone or in numerous combinations in order to evaluate its therapeutic value in various cancers (solid and liquid tumors). Results on non-Hodgkin's lymphoma, colorectal, lung, breast and prostate cancers appear to be encouraging.

A rather limited number of proteasome inhibitors have been reported (Kisselev A. F., Goldberg A. L. *Chemistry & Biology,* 2001, 8, 739-758; Reboud-Ravaux M (2002) "*Proteasome inhibitors*" in Protein Degradation in Health and Diseases, M. Reboud-Ravaux (Ed.), Progress in Molecular and Subcellular Biology, Springer-Verlag, Berlin, Heidelberg, New York; Papapostolou D., Reboud-Ravaux M. *J. Soc. Biol.,* 2004, 198, 263-278). Most are short peptides linked at the C-terminus to a reactive group (FIG. 1) which binds to the catalytic $O^\gamma$-Thr1 of the 6 catalytic sites of the proteasome with formation of a reversible (peptide aldehydes), poorly reversible (peptide boronates), or irreversible covalent adduct peptide vinyl sulfones, peptide epoxyketones) (FIGS. 2A and 2B).

The natural product lactacystin is a non peptidic molecule which cannot penetrate the cells (FIG. 2B). At neutral pH, it is rapidly hydrolyzed to give B3-lactone which easily enters cells. The β-lactone reacts with $O^\gamma$-Thr1 to give a stable covalent acyl-enzyme ($t_{1/2}$=20 h). Lactacystin does not react specifically with proteasome since cathepsin A, a lysosomal carboxypeptidase and cytosolic tripeptidyl peptidase II are also inhibited. The natural epoxyketones (epoxomicin and eponemicin) have the unique particularity to react with O$^\gamma$ and α-NH$_2$ of Thr1. This probably explains that these compounds are the most selective proteasome inhibitors but they irreversibly inhibit proteasome. Several polyol compounds such as (−)epigallocatechin-3-gallate give stable acyl-enzymes upon reaction with proteasomes.

Non covalent inhibitors have been investigated less extensively, and in principle, should lower side-effects. Only three classes of such inhibitors are known. Ritonavir (Schmidtke, G.; Holzhütter, H.-G.; Bogyo, M.; Kairies, N.; Groll, M.; De Giuli, R.; Emch, S.; Groettrup, M. *J. Biol. Chem.* 1999, 274, 35734-35740) and benzylstatine derivatives (Furet, P.; Imbach, P.; Noorani, M.; Koeppler J.; Laumen, K.; Lang, M.; Guagnano, P. F.; Roesel, J.; Zimmermann, J.; García-Echeverría, C. *J. Med. Chem.* 2004, 47 (20), 4810-4813.; Furet, P.; García-Echeverría, C.; Imbach, P.; Lang, M.; Zimmermann, J. (Novartis) PCT Int. Appl., WO 2001089282; 2001.) were shown to inhibit proteasome non covalently (FIG. 3). A cyclic peptide TMC-95A which is a metabolite of *Apiospora montagnei* is a potent reversible inhibitor with no inhibition of m-calpain, cathepsin-L and trypsin (Onuki, T.; Sugita, N., Kono, O.; Kogushi, Y.; Murakami, T.; Nishio, M., (Tanabe Seiyaku Co., Ltd) JP 11029595; 1999; Koguchi, Y.; Kohno, J.; Nishio, M.; Takahashi, K.; Okuda, T.; Ohnuki, T.; Komatsubara, S., *J Antibiot* (Tokyo) 2000, 53, (2), 105-9; Kohno, J.; Koguchi, Y.; Nishio, M.; Nakao, K.; Kuroda, M.; Shimizu, R.; Ohnuki, T.; Komatsubara, S., *J Org Chem* 2000, 65, (4), 990-5). Some macrocyclic derivatives of TMC-95 were prepared and were shown to be non covalent inhibitors of proteasome (Kaiser, M.; Groll, M.; Renner, C.; Huber, R.; Moroder, L., *Angew. Chem. Int. Ed.* 2002, 41, (5), 780-783; Kaiser, M.; Siciliano, C.; Assfalg-Machleidt, I.; Groll, M.; Milbradt, A. G.; Moroder, L., *Org. Lett.* 2003, 5, (19), 3435-3437; Kaiser, M., Groll, M., Siciliano, C., Assfalg-Machleidt I., Weyher E., Kohno J., Milbradt A. G., Renner G., Huber R., Moroder L. *ChemBioChem.* 2004, 5, 1256-1266; Lin, S.; Yang, Z. Q.; Kwok, B. H.; Koldobskiy, M.; Crews, C. M.; Danishefsky, S. J., *J. Am. Chem. Soc.* 2004, 126, (20), 6347-6355). X-ray analysis of the complex formed between proteasome and TMC-95A proved a non-covalent binding to active sites (Groll, M.; Huber, R.; Kaiser, M.; Renner, C.; Moroder, L.; Kohno, J. Crystals of proteasome-inhibitor complex. *PCT Int. Appl., WO* 2002081501; 2002; Groll, M.; Koguchi, Y.; Huber, R.; Kohno, J. *J. Mol. Biol.* 2001, 311, 543-548).

Proteasome inhibitors are potential drugs by retarding or blocking the degradation of specific proteins in disorders associated with their excessive degradation. Among them, are found: inflammatory processes (Elliott et al. *J. Med. Chem.* 2003, 81, 235-245), various cancers (Adams J. *Cancer Cell* 2003, 5, 417-421; Adams J. *Nature Reviews/Cancer* 2004, 4, 349-359), immunological and auto-immune diseases (Schwartz et al. *J. Immunol.* 2000, 164, 6147-6157), muscle wasting (Lecker et al. *FASEB J.* 2004, 18, 39-51), ischemia and cardiac pathologies (Wojcik and Napoli *Stroke* 2004, 35, 1506-1518), myopathies (Galbiati et al. *J. Biol. Chem.* 2000, 275, 37702-37711), cystis fibrosis (Chen et al. *Biochemistry* 2000, 39, 3797-3803).

Proteasome activators are susceptible to favor degradation of oxidized proteins and prevent the formation of protein aggregates as observed in Alzheimer's and Parkinson's diseases (Cookson *Ann. Neurol.* 2004, 56, 315-316). Aggregated, cross-linked and oxidized proteins can inhibit 20S proteasome (Davies *Biochimie* 2001, 83, 301-310). Consequently, an increase of proteasome activity can be beneficial in aging processes, noticeably in cutaneous aging.

The main goal of the present invention is to provide new compounds acting as modulators of the proteasome activity (inhibitors or activators), and having the following advantages when compared to the prior art compounds mentioned above:

a. they are mild, controllable and reversible inhibitors, with no creation of a covalent bond between the enzyme and the inhibitor. Due to the implication of proteasome in a large variety of physiological processes, an irreversible permanent inhibition of proteasome would likely be detrimental.

b. they are low-molecular-weight molecules and their synthetic routes are simple;

c. they have a differential selectivity towards the three kinds of active sites.

The invention relates to the use of compounds of the following general formula (I):

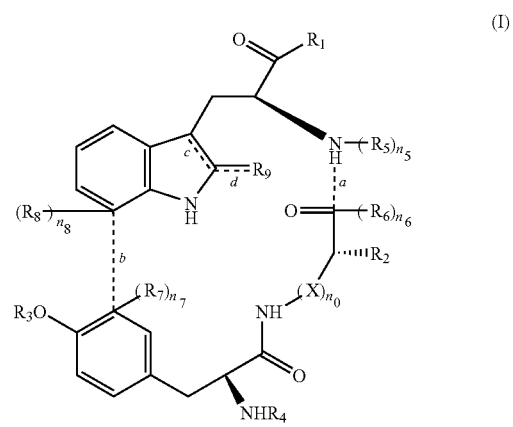

wherein:
at least one of the bonds a and b, and only one of the bonds c or d, are present, provided that:
  when the bonds a and b are present simultaneously, then R$_9$ is H, and n$_5$=n$_6$ n$_7$=n$_8$=0,
  when the bond a is present, but not the bond b, then n$_5$=n$_6$=0, and n$_7$=n$_8$=1,
  when the bond b is present, but not the bond a, then n$_5$=n$_6$=1, and n$_7$=n$_8$=0,
  when the bond c is present, and d is absent, then R$_9$ is H,
  when the bond d is present, and c is absent, then R$_9$ is an oxygen atom O,
n$_0$ is 0 or 1, and when n$_0$ is 1, X=CH$_2$ or X=NCH$_2$C$_6$H$_5$,
R$_1$ is:
  OH, or a OR$_{10}$ group in which R$_{10}$ is a linear or branched alkyl group from 1 to 5 carbon atoms,
  or a group of formula NH—(CH$_2$)$_{n1}$—R$_{11}$ in which:
    n$_1$=0, or an integer from 1 to 5,
    R$_{11}$ is a linear or branched alkyl group from 1 to 5 carbon atoms, an aryl group, possibly substituted, NH$_2$, or NHR$_{12}$ in which R$_{12}$ is a protecting group of amine functions, such as the tertiobutyloxycarbonyl (Boc) group, or the CO—O—CH$_2$—C$_6$H$_5$ (Z) group,
R$_2$ is:
  H, or a linear or branched alkyl group from 1 to 5 carbon atoms,
  or a group of formula (CH$_2$)$_{n2}$—(CO)$_{n3}$—NR$_{13}$R$_{14}$, in which:
    n$_2$ is an integer from 1 to 5,
    n$_3$=0 or 1, $R_{13}$ and $R_{14}$, independently from one another, are:
H,
or a protecting group of amine functions, such as Boc, or Z,
or a group of formula C(=NH)NH$R_{15}$ in which $R_{15}$ is H or a protecting group of amine functions, such as Boc, or Z, mentioned above,
or a side chain from proteogenic aminoacids, $R_3$ is H, or a linear or branched alkyl group from 1 to 5 carbon atoms, optionally substituted with an aryl group, $R_4$ is H, or a protecting group of amine functions, such as Boc, or Z, $R_5$ is H, or a protecting group of amine functions, such as Boc, or Z, $R_6$ is a O$R_{16}$ group in which $R_{16}$ is a linear or branched alkyl group from 1 to 5 carbon atoms, $R_7$ and $R_8$, independently from one another, are H, or a halogen atom, such as Br, I, or Cl, as modulators of the proteasome activity, in the frame of the preparation of a medicament useful for the prevention or treatment of diseases wherein the proteasome is involved, or the preparation of cosmetic compositions, or of phytosanitary compositions.

By the expression "modulators of the proteasome activity", it must be understood that the compounds as defined above according to the present invention are:
either inhibitors of the proteasome activity, i.e. have the following inhibition properties against chymotrypsin-like, or/and trypsin-like, or/and post-acid activities of rabbit 20S proteasome which can be measured using the appropriate fluorogenic substrate, as described below: initial rates determined in control experiments (without test compound) were considered to be 100% of the peptidasic activity, initial rates below 100% were considered to be inhibitions,
or activators of the proteasome activity, i.e. have the following activation properties against chymotrypsin-like, or/and trypsin-like, or/and post-acid activities of rabbit 20S proteasome, which can be measured using the appropriate fluorogenic substrate as described below; initial rates that were above 100% in the presence of a test compound were considered to be activators.

The invention concerns more particularly the use as defined above of compounds of the following formula (II):

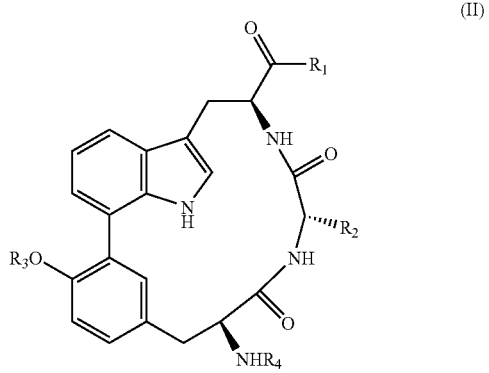

(II)

in which $R_1$, $R_2$, $R_3$, and $R_4$, are such as defined above.

The invention relates more particularly to the use as defined above of compounds of formula (II) in which:
$R_1$ is a group O$R_{10}$ in which $R_{10}$ is a linear or branched alkyl group from 1 to 5 carbon atoms, $R_2$ is a linear or branched alkyl group from 1 to 5 carbon atoms, $R_3$ is a linear or branched alkyl group from 1 to 5 carbon atoms, optionally substituted with an aryl group, $R_4$ is a protecting group of amine functions, such as Boc.

The invention also concerns more particularly the use as defined above of compounds of formula (II) in which:
$R_1$ is OCH$_3$,
$R_2$ is CH$_3$, or CH$_2$—CH—(CH$_3$)$_2$,
$R_3$ is CH$_3$, or CH$_2$—C$_6$H$_5$,
$R_4$ is Boc.

The invention relates more particularly to the use as defined above of compounds of formula (II) in which:
$R_1$ is OCH$_3$, $R_2$ is CH$_2$—CH—(CH$_3$)$_2$, $R_3$ is CH$_3$, and $R_4$ is Boc (compound A374F1),
or $R_1$ is OCH$_3$, $R_2$ is CH$_2$—CH—(CH$_3$)$_2$, $R_3$ is CH$_2$—C$_6$H$_5$, and $R_4$ is Boc (compound A291),
or $R_1$ is OCH$_3$, $R_2$ and $R_3$ are CH$_3$, and $R_4$ is Boc (compound A389F1p12).

The invention also concerns the use as defined above of compounds of the following formula (III):

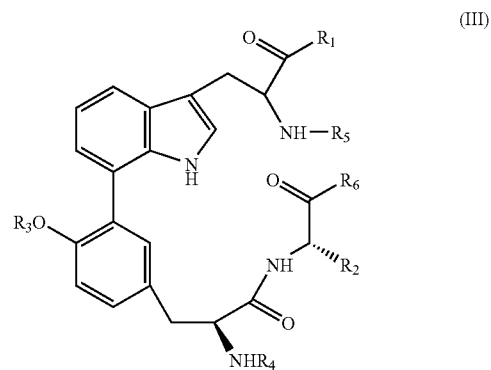

(III)

in which $R_1$, $R_2$, $R_3$, $R_4$, $R_5$, and $R_6$, are such as defined above.

The invention relates more particularly to the use as defined above of compounds of formula (III) in which:
$R_1$ is a group O$R_{10}$ in which $R_{10}$ is a linear or branched alkyl group from 1 to 5 carbon atoms, or a group of formula NH—(CH$_2$)$_{n1}$—$R_{11}$ in which $n_1$=0, and $R_{11}$ is a linear or branched alkyl group from 1 to 5 carbon atoms, $R_2$ is a linear or branched alkyl group from 1 to 5 carbon atoms, $R_3$ is a linear or branched alkyl group from 1 to 5 carbon atoms, optionally substituted with an aryl group, $R_4$ is a protecting group of amine functions, such as Boc, $R_5$ is a protecting group of amine functions, such as Z, $R_6$ is a O$R_{16}$ group in which $R_{16}$ is a linear or branched alkyl group from 1 to 5 carbon atoms.

The invention also relates more particularly to the use as defined above of compounds of formula (III) in which:
$R_1$ is OCH$_2$CH$_3$, or NHCH$_3$,
$R_2$ is CH$_3$, or CH$_2$—CH—(CH$_3$)$_2$,
$R_3$ is CH$_2$—C$_6$H$_5$,
$R_4$ is un groupe Boc,
$R_5$ is un groupe Z,
$R_6$ is OCH$_3$.

The invention concerns more particularly the use as defined above of compounds of formula (III) in which:
$R_1$ is OCH$_2$CH$_3$, $R_2$ is CH$_2$—CH—(CH$_3$)$_2$, $R_3$ is CH$_2$—C$_6$H$_5$, $R_4$ is Boc, $R_5$ is Z, and $R_6$ is OCH$_3$ (compound SP221), or $R_1$ is $NHCH_3$, $R_2$ is $CH_3$, $R_3$ is $CH_2$—$C_6H_5$, $R_4$ is Boc, $R_5$ is Z, and $R_6$ is $OCH_3$ (compound SP225F2), or $R_1$ is $NHCH_3$, $R_2$ is $CH_2$—CH—$(CH_3)_2$, $R_3$ is $CH_2$—$C_6H_5$, $R_4$ is Boc, $R_5$ is Z, and $R_6$ is $OCH_3$ (compound SP226F1).

The invention also concerns the use as defined above of compounds of the following formula (IV):

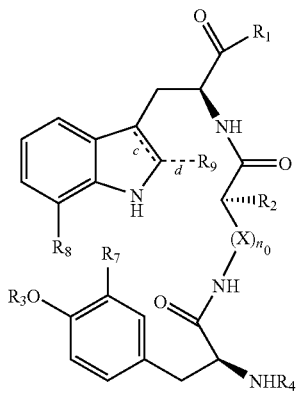

(IV)

in which c, d, $n_0$, X, $R_1$, $R_2$, $R_3$, $R_4$, $R_7$, $R_8$, and $R_9$, are such as defined above.

The invention relates more particularly to the use as defined above of compounds of the following formula (IV-1):

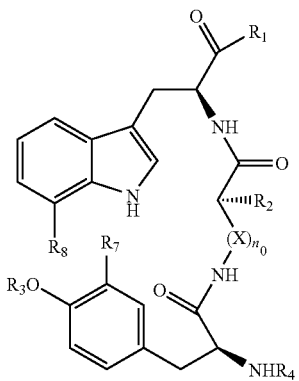

(IV-1)

corresponding to compounds of formula (IV) in which:
the bond c is present, and $R_9$ is H,
$n_0=0$ or 1,
X=$CH_2$ or $NCH_2C_6H_5$,
$R_1$ is OH, or a group $OR_{10}$ in which $R_{10}$ is a linear or branched alkyl group from 1 to 5 carbon atoms, or a group of formula NH—$(CH_2)_{n1}$—$R_{11}$ in which $n_1=0$, and $R_{11}$ is a linear or branched alkyl group from 1 to 5 carbon atoms,
$R_2$ is H, a linear or branched alkyl group from 1 to 5 carbon atoms, or a group of formula $(CH_2)_{n2}$—$(CO)_{n3}$—$NR_{13}R_{14}$, in which $n_2=1$ to 5, $n_3=1$, and $R_{13}=R_{14}=H$,
$R_3$ is a linear or branched alkyl group from 1 to 5 carbon atoms, optionally substituted with an aryl group,
$R_4$ is a protecting group of amine functions, such as Boc,
$R_7$ and $R_8$, independently from one another, are a halogen atom, such as Br, I.

The invention concerns more particularly the use as defined above of compounds of formula (IV-1) in which:
$R_1$ is OH, $OCH_3$, $OCH_2CH_3$, or $NHCH_3$,
$R_2$ is H, $CH_3$, $CH_2$—CH—$(CH_3)_2$, or $CH_2CONH_2$,
$R_3$ is $CH_3$, or $CH_2$—$C_6H_5$,
$R_4$ is un groupe Boc,
$R_7$ is I,
$R_8$ is Br.

The invention also relates more particularly to the use as defined above of compounds of the following formula (IV-1a):

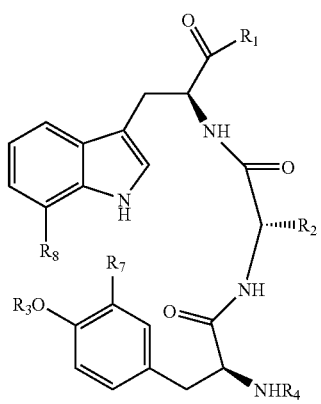

(IV-1a)

The invention concerns more particularly the use as defined above of compounds of formula (IV-1a) in which:
$R_1$ is $OCH_3$, $R_2$ is $CH_3$, $R_3$ is $CH_2$—$C_6H_5$, $R_4$ is Boc, $R_7$ is I, and $R_8$ is Br (compound A248), or $R_1$ is OH, $R_2$ is $CH_3$, $R_3$ is $CH_2$—$C_6H_5$, 4 is Boc, $R_7$ is I, and $R_8$ is Br (compound A215), or $R_1$ is $OCH_3$, $R_2$ is $CH_2CONH_2$, $R_3$ is $CH_2$—$C_6H_5$, $R_4$ is Boc, $R_7$ is I, and $R_8$ is Br (compound SP274), or $R_1$ is $OCH_3$, $R_2$ is $CH_2$—CH—$(CH_3)_2$, $R_3$ is $C_1H_3$, $R_4$ is Boc, $R_7$ is I, and $R_8$ is Br (compound A363), or $R_1$ is $OCH_2CH_3$, $R_2$ is $CH_2$—CH—$(CH_3)_2$, $R_3$ is $CH_3$, $R_4$ is Boc, $R_7$ is I, and $R_8$ is Br (compound A340), or $R_1$ is $OCH_2CH_3$, $R_2$ is $CH_2$—CH—$(CH_3)_2$, $R_3$ is $CH_2$—$C_6H_5$, $R_4$ is Boc, $R_7$ is I, and $R_8$ is Br (compound A174), or $R_1$ is $OCH_3$, $R_2$ is $CH_2$—CH—$(CH_3)_2$, $R_3$ is $CH_2$—$C_6H_5$, $R_4$ is Boc, $R_7$ is I, and $R_8$ is Br (compound A268), or $R_1$ is $OCH_3$, $R_2$ is $CH_3$, $R_3$ is $CH_3$, $R_4$ is Boc, $R_7$ is I, and $R_8$ is Br (compound A385), or $R_1$ is $NHCH_3$, $R_2$ is $CH_3$, $R_3$ is $CH_2$—$C_6H_5$, $R_4$ is Boc, $R_7$ is I, and $R_8$ is Br (compound A254).

Preferred compounds of formula (IV-1a) used in the frame of the present invention are compounds A215, SP274 and A254.

The invention relates more particularly to the use as defined above of compounds of the following formula (IV-1b):

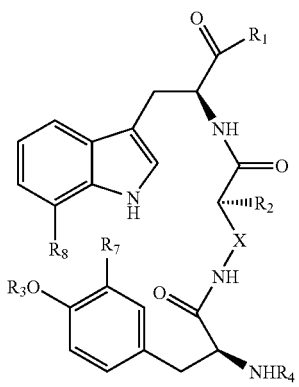

(IV-1b)

The invention also concerns more particularly the use as defined above of compounds of formula (IV-1b) in which:
$R_1$ is $OCH_3$, $R_2$ is H, $R_3$ is $CH_3$, $R_4$ is Boc, $R_7$ is I, $R_8$ is Br, and $X=CH_2$ (compound A493), or
$R_1$ is $OCH_3$, $R_2$ is $CH_3$, $R_3$ is $CH_3$, $R_4$ is Boc, $R_7$ is I, $R_8$ is Br, and $X$ $NCH_2C_6H_5$.

The invention also relates to the use of compounds of formula (IV) as defined above wherein $R_7$ and $R_8$ are H.

The invention also concerns the use as defined above of compounds of the following formula (IV-2):

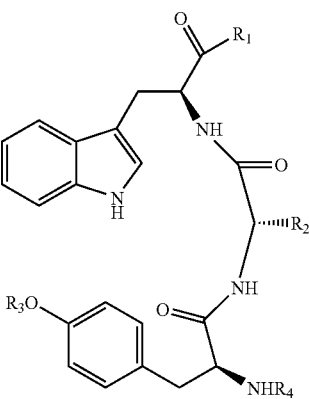

(IV-2)

corresponding to compounds of formula (IV) in which:
the bond c is present, and $R_9$ is H,
$n_0=0$,
$R_1$ is OH, or a group $OR_{10}$ in which $R_{10}$ is a linear or branched alkyl group from 1 to 5 carbon atoms, or a group of formula $NH-(CH_2)_{n1}-R_{11}$ in which $n_1=0$, or an integer from 1 to 5, and $R_{11}$ is a linear or branched alkyl group from 1 to 5 carbon atoms, an aryl group, possibly substituted, $NH_2$, or $NHR_{12}$ in which $R_{12}$ is a protecting group of amine functions, such as Boc or Z,
$R_2$ is H, or a linear or branched alkyl group from 1 to 5 carbon atoms, or a group of formula $(CH_2)_{n2}-(CO)_{n3}-NR_{13}R_{14}$, in which $n_2$ is an integer from 1 to 5, $n_3=0$ or 1, and $R_{13}$ and $R_{14}$, independently from one another, are H, or a protecting group of amine functions, such as Boc, or Z, or a group of formula $C(=NH)NHR_{15}$ in which $R_{15}$ is H or a protecting group of amine functions, such as Boc, or Z, mentioned above,
$R_3$ is H, or a linear or branched alkyl group from 1 to 5 carbon atoms, optionally substituted with an aryl group, $R_4$ is a protecting group of amine functions, such as Boc, $R_7=R_8=H$.

The invention concerns more particularly the use as defined above, of compounds of formula (IV-2) in which:
$n_0=0$,
$R_1$ is OH, $OCH_3$, $NHCH_2C_6H_5$, $NHC_6H_5$, $NHC_6H_4OH$, or $NH(CH_2)_4NHBoc$,
$R_2$ is H, $CH_3$, $CH_2-CH-(CH_3)_2$, $CH_2CONH_2$, $(CH_2)_3NHC(=NH)NH_2$, or $(CH_2)_3NZC(=NH)NHZ$, or $(CH_2)_4NHBoc$,
$R_3$ is H, or $CH_2-C_6H_5$,
$R_4$ is Boc.

The invention relates more particularly to the use as defined above of compounds of formula (IV-2) in which:
$R_1$ is $NHCH_2C_6H_5$, $R_2$ is H, $R_3$ is $CH_2-C_6H_5$, and $R_4$ is Boc (compound PSV11R),
or $R_1$ is OH, $R_2$ is H, $R_3$ is $CH_2-C_6H_5$, and $R_4$ is Boc (compound NR35),
or $R_1$ is $NHC_6H_5$, $R_2$ is $CH_3$, $R_3$ is $CH_2-C_6H_5$, and $R_4$ is Boc (compound SP303r2),
or $R_1$ is $NHCH_2C_6H_5$, $R_2$ is $CH_3$, $R_3$ is $CH_2-C_6H_5$, and $R_4$ is Boc (compound SP304R),
or $R_1$ is $NHC_6H_4OH$, $R_2$ is $CH_3$, $R_3$ is $CH_2-C_6H_5$, and $R_4$ is Boc (compound SP313P),
or $R_1$ is $NH(CH_2)_4NHBoc$, $R_2$ is $CH_3$, $R_3$ is $CH_2-C_6H_5$, and $R_4$ is Boc (compound SP305R),
or $R_1$ is $OCH_3$, $R_2$ is $CH_3$, $R_3$ is $CH_2-C_6H_5$, and $R_4$ is Boc (compound NR36),
or $R_1$ is $OCH_3$, $R_2$ is $CH_3$, $R_3$ is H, and $R_4$ is Boc (compound NR40),
or $R_1$ is $NHC_6H_5$, $R_2$ is $CH_2-CH-(CH_3)_2$, $R_3$ is $CH_2-C_6H_5$, and $R_4$ is Boc (compound A424P),
or $R_1$ is $NHCH_2C_6H_5$, $R_2$ is $CH_2-CH-(CH_3)_2$, $R_3$ is $CH_2-C_6H_5$, and $R_4$ is Boc (compound A414P),
or $R_1$ is $NHC_6H_4OH$, $R_2$ is $CH_2-CH-(CH_3)_2$, $R_3$ is $CH_2-C_6H_5$, and $R_4$ is Boc (compound A418P),
or $R_1$ is $NH(CH_2)_4NHBoc$, $R_2$ is $CH_2-CH-(CH_3)_2$, $R_3$ is $CH_2-C_6H_5$, and $R_4$ is Boc (compound SP296P),
or $R_1$ is $NHC_6H_5$, $R_2$ is $CH_2CONH_2$, $R_3$ is $CH_2-C_6H_5$, and $R_4$ is Boc (compound SP314C2),
or $R_1$ is $NHCH_2C_6H_5$, $R_2$ is $CH_2CONH_2$, $R_3$ is $CH_2-C_6H_5$, and $R_4$ is Boc (compound A416),
or $R_1$ is $NHC_6H_4OH$, $R_2$ is $CH_2CONH_2$, $R_3$ is $CH_2-C_6H_5$, and $R_4$ is Boc (compound SP318C),
or $R_1$ is $NH(CH_2)_4NHBoc$, $R_2$ is $CH_2CONH_2$, $R_3$ is $CH_2-C_6H_5$, and $R_4$ is Boc (compound SP323C2),
or $R_1$ is $NHC_6H_5$, $R_2$ is $(CH_2)_3NHC(=NH)NH_2$, $R_3$ is H, and $R_4$ is Boc (compound SP325),
or $R_1$ is $NHC_6H_4OH$, $R_2$ is $(CH_2)_3NHC(=NH)NH_2$, $R_3$ is H, and $R_4$ is Boc (compound SP324),
or $R_1$ is $NHC_6H_5$, $R_2$ is $(CH_2)_3NZC(=NH)NHZ$, $R_3$ is $CH_2-C_6H_5$, and $R_4$ is Boc (compound SP310C),
or $R_1$ is $NHCH_2C_6H_5$, $R_2$ is $(CH_2)_3NZC(=NH)NHZ$, $R_3$ is $CH_2-C_6H_5$, and $R_4$ is Boc (compound SP315C2),
or $R_1$ is $NHC_6H_4OH$, $R_2$ is $(CH_2)_3NZC(=NH)NHZ$, $R_3$ is $CH_2-C_6H_5$, and $R_4$ is Boc (compound SP320P2),
or $R_1$ is $NH(CH_2)_4NHBoc$, $R_2$ is $(CH_2)_3NZC(=NH)NHZ$, $R_3$ is $CH_2-C_6H_5$, and
$R_4$ is Boc (compound SP311C),
or $R_1$ is $NHC_6H_5$, $R_2$ is $(CH_2)_4NHBoc$, $R_3$ is $CH_2-C_6H_5$, and $R_4$ is Boc (compound SP306P),
or $R_1$ is $NHCH_2C_6H_5$, $R_2$ is $(CH_2)_4NHBoc$, $R_3$ is $CH_2-C_6H_5$, and $R_4$ is Boc (compound SP307P),
or $R_1$ is $NHC_6H_4OH$, $R_2$ is $(CH_2)_4NHBoc$, $R_3$ is $CH_2-C_6H_5$, and $R_4$ is Boc (compound SP319P),
or $R_1$ is $NH(CH_2)_4NHBoc$, $R_2$ is $(CH_2)_4NHBoc$, $R_3$ is $CH_2-C_6H_5$, and $R_4$ is Boc (compound SP308P).

or $R_1$ is OH, $R_2$ is $CH_3$, $R_3$ is $CH_2$—$C_6H_5$, and $R_4$ is Boc (compound NR66).

or $R_1$ is OH, $R_2$ is $CH_3$, $R_3$ is H, and $R_4$ is Boc (compound NR68).

Preferred compounds of formula (IV-2) used in the frame of the present invention are the compounds SP313P, NR40, SP325, and SP324.

The invention also concerns the use as defined of compounds of the following formula (IV-3):

(IV-3)

corresponding to compounds of formula (IV) in which:
the bond d is present, and $R_9$ is an oxygen atom O,
$n_0=0$,
$R_1$ is OH, or a group $OR_{10}$ in which $R_{10}$ is a linear or branched alkyl group from 1 to 5 carbon atoms, or a group of formula NH—$(CH_2)_{n1}$—$R_{11}$ in which $n_1=0$, or an integer from 1 to 5, and $R_{11}$ is an aryl group, possibly substituted,
$R_2$ is H, or a linear or branched alkyl group from 1 to 5 carbon atoms, or a group of formula $(CH_2)_{n2}$—$(CO)_{n3}$—$NR_{13}R_{14}$, in which $n_2$ is an integer from 1 to 5, $n_3=0$ or 1, and $R_{13}$ and $R_{14}$, independently from one another, are H, or a protecting group of amine functions, such as Boc, or Z, or a group of formula C(=NH)$NHR_{15}$ in which $R_{15}$ is H or a protecting group of amine functions, such as Boc, or Z, mentioned above,
$R_3$ is H, or a linear or branched alkyl group from 1 to 5 carbon atoms, optionally substituted with an aryl group,
$R_4$ is a protecting group of amine functions, such as Boc,
$R_7=R_8=H$.

The invention relates more particularly to the use as defined above of compounds of formula (IV-3) in which:
$R_1$ is OH, $OCH_3$, $NHCH_2C_6H_5$, or $NHC_6H_5$,
$R_2$ is H, $CH_3$, $CH_2$—CH—$(CH_3)_2$, $(CH_2)_3$NZC(=NH)NHZ, or $(CH_2)_4$NHBoc,
$R_3$ is H, or $CH_2$—$C_6H_5$,
$R_4$ is Boc.

The invention also relates more particularly to the use as defined above of compounds of formula (IV-3) in which:
$R_1$ is $NHC_6H_5$, $R_2$ is $(CH_2)_3$NZC(=NH)NHZ, $R_3$ is $CH_2$—$C_6H_5$, and $R_4$ is Boc (compound CV11),
$R_1$ is $NHC_6H_5$, $R_2$ is $(CH_2)_4$NHBoc, $R_3$ is $CH_2$—$C_6H_5$, and $R_4$ is Boc (compound CV12),
$R_1$ is $NHC_6H_5$, $R_2$ is $CH_3$, $R_3$ is $CH_2$—$C_6H_5$, and $R_4$ is Boc (compound CV13),
$R_1$ is $NHC_6H_5$, $R_2$ is $CH_2$—CH—$(CH_3)_2$, $R_3$ is $CH_2$—$C_6H_5$, and $R_4$ is Boc (compound JV602),
$R_1$ is $NHCH_2C_6H_5$, $R_2$ is H, $R_3$ is $CH_2$—$C_6H_5$, and $R_4$ is Boc (compound NR15),
$R_1$ is $OCH_3$, $R_2$ is H, $R_3$ is $CH_2$—$C_6H_5$, and $R_4$ is Boc (compound NR38),
$R_1$ is $NHCH_2C_6H_5$, $R_2$ is $(CH_2)_3$NZC(=NH)NHZ, $R_3$ is $CH_2$—$C_6H_5$, and $R_4$ is Boc (compound NR16),
$R_1$ is $OCH_3$, $R_2$ is $CH_3$, $R_3$ is $CH_2$—$C_6H_5$, and $R_4$ is Boc,
$R_1$ is OH, $R_2$ is $CH_3$, $R_3$ is $CH_2$—$C_6H_5$, and $R_4$ is Boc,
$R_1$ is OH, $R_2$ is $CH_3$, $R_3$ is H, and $R_4$ is Boc,
$R_1$ is $OCH_3$, $R_2$ is $CH_3$, $R_3$ is H, and $R_4$ is Boc.

Preferred compounds of formula (IV-3) used in the frame of the present invention are the compounds CV12, CV13, NR15, and NR38.

The invention relates more particularly to the use of a compound as defined above, as modulators of the proteasome activity for the preparation of:
- a drug for prevention or treatment of pathologies involving proteasome, said pathologies being chosen from the group constituted by: cancers involving haematological or solid tumors, immunological diseases, auto-immune diseases, AIDS, inflammatory diseases, cardiac pathologies and consequences of ischemic processes in myocardial, cerebral or pulmonary regions, allograft rejection, myopathies, muscle wasting, cerebrovascular accidents, traumatisms, burns, pathologies associated with aging like Alzheimer's disease and Parkinson's disease, and the appearance of aging signs, or
- a drug for increasing the radiosensitization of a tumor, the sensitivity to chemotherapy and/or immunotherapy, or promoting the circumvention of resistances, or
- a cosmetic composition for the implementation of a method of cosmetic prevention or treatment of the appearance of cutaneous aging and/or photoaging, or
- phytosanitary compositions for the implementation of processes for modulating the defense response of plants, in particular phytosanitary compositions for the stimulation of plants defense response against phytopathogenic agents.

Advantageously pharmaceutical compositions or drugs used in the frame of the present invention comprise compounds as defined above mainly acting as inhibitors of the proteasome activity.

Preferred compounds contained in the pharmaceutical compositions as defined above are those of formula IV-1A, or IV-2, or IV-3, or IV-1B such as compounds A215, SP274, A254, or SP313P, NR40, SP325, SP324, or CV12, CV13, NR15, NR38, or A493.

Advantageously cosmetic compositions used in the frame of the present invention comprise compounds as defined above mainly acting as activators of the proteasome activity.

Preferred compounds contained in the cosmetic compositions as defined above are those of formula II, or III, or IV-1A, or IV-2, or IV-3, or IV-1B such as compounds A374F1, or SP221, or A363, or NR36, SP305R, SP314C2, or NR15, NR38, NR16, or A493.

Advantageously phytosanitary compositions used in the frame of the present invention comprise compounds as defined above mainly acting as inhibitors of the proteasome activity.

Preferred compounds contained in the phytosanitary compositions as defined above are those of formula IV-1A, or IV-2, or IV-3, or IV-1B such as compounds A215, SP274, A254, or SP313P, NR40, SP325, SP324, or CV12, CV13, NR15, NR38, or A493.

The invention also concerns a pharmaceutical composition, characterized in that it comprises a compound as defined above, in association with a pharmaceutically acceptable vehicle.

The invention relates more particularly to the pharmaceutical composition as defined above, characterized in that it contains a compound as defined above, at an appropriate amount for a daily administration of about twice a week for 4 weeks at about 1.5 mg/m$^2$.

The invention also relates more particularly to the pharmaceutical composition as defined above, characterized in that it is in a form suitable for intravenous or per os administration.

The invention also concerns a cosmetic composition characterized in that it comprises a compound as defined above, in association with a pharmacologically acceptable vehicle.

The invention relates more particularly to the cosmetic composition as defined above, characterized in that it is in a form suitable for dermatological administration, in particular as a cream, pomade or gel.

The invention concerns more particularly the cosmetic composition as defined above, characterized in that it contains a compound as defined above, at an appropriate amount for a daily administration of about 1 mg/m$^2$ to 10 mg/m$^2$ of skin.

The invention also concerns a phytosanitary composition, characterized in that it comprises a compound as defined above, if necessary in association with an acceptable vehicle in phytosanitary field.

The invention relates more particularly to the phytosanitary composition as defined above, characterized in that it comprises a compound as defined above, at an appropriate amount for an administration by spraying of about 1 g/m$^2$ to 10 g/m$^2$.

The invention also concerns the compounds of formula (I), and more particularly of formula (II), (III), and (IV) as defined above.

The invention also relates to compounds of the following formula (III)

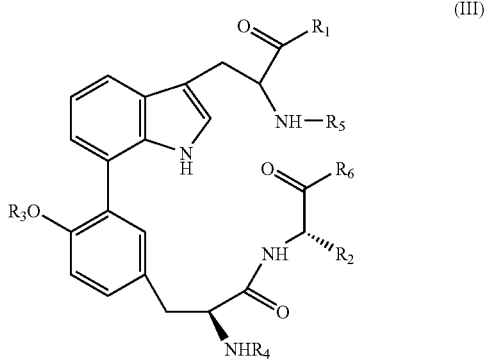

(III)

in which $R_1$, $R_2$, $R_3$, $R_4$, $R_5$, and $R_6$, are such as defined above, the compound of formula (III) in which $R_1$=NH(CH$_2$)$_2$CH$_3$, $R_2$=CH$_2$CONH$_2$, $R_3$=CH$_3$, $R_4$=Z, $R_5$=Boc, $R_6$=OtBu being excluded.

The invention relates more particularly to compounds of formula (III) as defined above in which:

$R_1$ is a group $OR_{10}$ in which $R_{10}$ is a linear or branched alkyl group from 1 to 5 carbon atoms, or a group of formula NH—(CH$_2$)$_{n1}$—R$_{11}$ in which $n_1$=0, and $R_{11}$ is a linear or branched alkyl group from 1 to 5 carbon atoms, $R_2$ is a linear or branched alkyl group from 1 to 5 carbon atoms, $R_3$ is a linear or branched alkyl group from 1 to 5 carbon atoms, optionally substituted with an aryl group, $R_4$ is a protecting group of amine functions, such as Boc, $R_5$ is a protecting group of amine functions, such as Z, $R_6$ is a $OR_{16}$ group in which $R_{16}$ is a linear or branched alkyl group from 1 to 5 carbon atoms.

The invention also relates more particularly to compounds of formula (III) as defined above in which:

$R_1$ is OCH$_2$CH$_3$, or NHCH$_3$, $R_2$ is CH$_3$, or CH$_2$—CH—(CH$_3$)$_2$, $R_3$ is CH$_2$—C$_6$H$_5$, $R_4$ is Boc, $R_5$ is Z, $R_6$ is OCH$_3$.

The invention concerns more particularly the compounds of formula (III) as defined above in which:

$R_1$ is OCH$_2$CH$_3$, $R_2$ is CH$_2$—CH—(CH$_3$)$_2$, $R_3$ is CH$_2$—C$_6$H$_5$, $R_4$ is Boc, $R_5$ is Z, and $R_6$ is OCH$_3$ (compound SP221), or $R_1$ is NHCH$_3$, $R_2$ is CH$_3$, $R_3$ is CH$_2$—C$_6$H$_5$, $R_4$ is Boc, $R_5$ is Z, and $R_6$ is OCH$_3$ (compound SP225F2), or $R_1$ is NHCH$_3$, $R_2$ is CH$_2$—CH—(CH$_3$)$_2$, $R_3$ is CH$_2$—C$_6$H$_5$, $R_4$ is Boc, $R_5$ is Z, and $R_6$ is OCH$_3$ (compound SP226F1).

The invention also relates to compounds as defined above, of the following formula (IV):

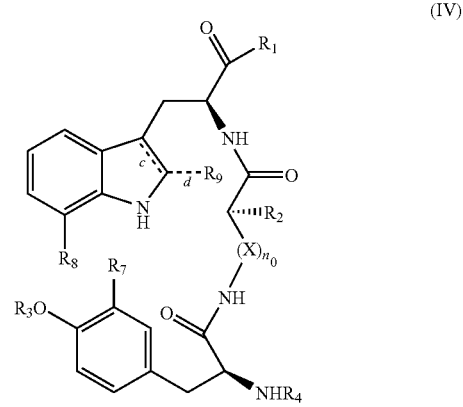

(IV)

in which c, d, $n_0$, X, $R_1$, $R_2$, $R_3$, $R_4$, $R_7$, $R_8$, and $R_9$, are such as defined above, the compounds of formula (IV) in which $n_0$=0, $R_9$=H, $R_1$=OCH$_3$, $R_4$ is Boc, $R_7$ is I, $R_8$ is Br, and $R_2$ is CH$_3$, and $R_3$ is CH$_2$—C$_6$H$_5$ (compound A248), or $R_2$ is CH$_2$CONH$_2$, and $R_3$ is CH$_2$—C$_6$H$_5$ (compound SP274), or $R_2$ is CH$_2$—CH—(CH$_3$)$_2$, and $R_3$ is CH$_3$ (compound A363), or $R_2$ is CH$_2$—CH—(CH$_3$)$_2$, and $R_3$ is CH$_2$—C$_6$H$_5$ (compound A268), being excluded.

The invention relates more particularly to compounds as defined above, of the following formula (IV-1):

(IV-1)

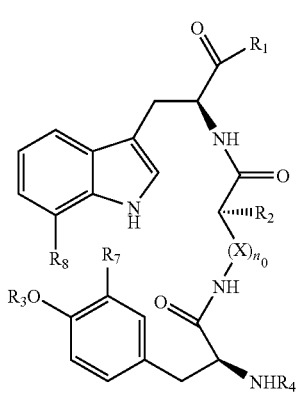

corresponding to compounds of formula (IV) in which:
the bond c is present, and $R_9$ is H,
$n_0=0$ or 1,
$X=CH_2$ or $NCH_2C_6H_5$,
$R_1$ is OH, or a group $OR_{10}$ in which $R_{10}$ is a linear or branched alkyl group from 1 to 5 carbon atoms, or a group of formula $NH-(CH_2)_{n1}-R_{11}$ in which $n_1=0$, and $R_{11}$ is a linear or branched alkyl group from 1 to 5 carbon atoms,
$R_2$ is H, a linear or branched alkyl group from 1 to 5 carbon atoms, or a group of formula $(CH_2)_{n2}-(CO)_{n3}-NR_{13}R_{14}$, in which $n_2=1$ to 5, $n_3=1$, and $R_{13}=R_{14}=H$,
$R_3$ is a linear or branched alkyl group from 1 to 5 carbon atoms, optionally substituted with an aryl group,
$R_4$ is a protecting group of amine functions, such as Boc,
$R_7$ and $R_8$, independently from one another, are a halogen atom, such as Br, I.

The invention concerns more particularly compounds of formula (IV-1) as defined above in which:
$R_1$ is OH, $OCH_3$, $OCH_2CH_3$, or $NHCH_3$,
$R_2$ is H, $CH_3$, $CH_2-CH-(CH_3)_2$, or $CH_2CONH_2$,
$R_3$ is $CH_3$, or $CH_2-C_6H_5$,
$R_4$ is Boc,
$R_7$ is I,
$R_8$ is Br.

The invention relates more particularly to compounds as defined above, of the following formula (IV-1a):

(IV-1a)

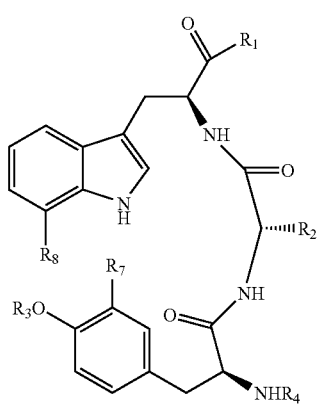

The invention also relates more particularly to compounds of formula (IV-1a) as defined above in which:
$n_0=0$, $R_1$ is OH, $R_2$ is $CH_3$, $R_3$ is $CH_2-C_6H_5$, $R_4$ is Boc, $R_7$ is I, and $R_8$ is Br (compound A215), or $n_0=0$, $R_1$ is $OCH_2CH_3$, $R_2$ is $CH_2-CH-(CH_3)_2$, $R_3$ is $CH_3$, $R_4$ is Boc, $R_7$ is I, and $R_8$ is Br (compound A340),
or $n_0=0$, $R_1$ is $OCH_2CH_3$, $R_2$ is $CH_2-CH-(CH_3)_2$, $R_3$ is $CH_2-C_6H_5$, $R_4$ is Boc, $R_7$ is I, and $R_8$ is Br (compound A174),
or $n_0=0$, $R_1$ is $OCH_3$, $R_2$ is $CH_3$, $R_3$ is $CH_3$, $R_4$ is Boc, $R_7$ is I, and $R_8$ is Br (compound A385),
or $n_0=0$, $R_1$ is $NHCH_3$, $R_2$ is $CH_3$, $R_3$ is $CH_2-C_6H_5$, $R_4$ is Boc, $R_7$ is I, and $R_8$ is Br (compound A254).

The invention relates more particularly to compounds as defined above of the following formula (IV-1b):

(IV-1b)

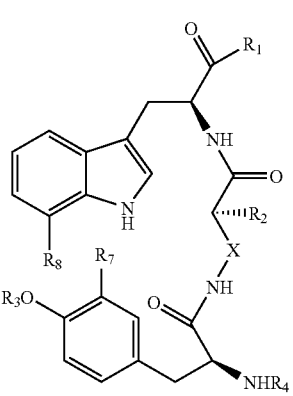

The invention concerns more particularly compounds of formula (IV-1b) as defined above in which
$R_1$ is $OCH_3$, $R_2$ is H, $R_3$ is $CH_3$, $R_4$ is Boc, $R_7$ is I, $R_8$ is Br, and $X=CH_2$ (compound A493), or
$R_1$ is $OCH_3$, $R_2$ is $CH_3$, $R_3$ is $CH_3$, R is Boc, $R_7$ is I, $R_8$ is Br, and $X=NCH_2C_6H_5$.

The invention also relates to compounds of formula (IV) as defined above wherein $R_7$ and $R_8$ are H.

The invention also concerns compounds as defined above of the following formula (IV-2):

(IV-2)

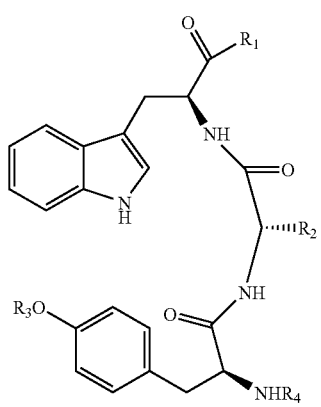

corresponding to compounds of formula (IV) in which:
the bond c is present, and $R_9$ is H,
$n_0=0$,
$R_1$ is OH, or a group $OR_{10}$ in which $R_{10}$ is a linear or branched alkyl group from 1 to 5 carbon atoms, or a group of formula $NH-(CH_2)_{n1}-R_{11}$ in which $n_1=0$, or an integer from 1 to 5, and $R_{11}$ is a linear or branched alkyl group from 1 to 5 carbon atoms, an aryl group, possibly substituted, NH$_2$, or NHR$_{12}$ in which R$_{12}$ is a protecting group of amine functions, such as Boc or Z, R$_2$ is H, or a linear or branched alkyl group from 1 to 5 carbon atoms, or a group of formula (CH$_2$)$_{n2}$—(CO)$_{n3}$—NR$_{13}$R$_{14}$, in which n$_2$ is an integer from 1 to 5, n$_3$=0 or 1, and R$_{13}$ and R$_{14}$, independently from one another, are H, or a protecting group of amine functions, such as Boc, or Z, or a group of formula C(=NH)NHR$_{15}$ in which R$_{15}$ is H or a protecting group of amine functions, such as Boc, or Z, mentioned above, R$_3$ is H, or a linear or branched alkyl group from 1 to 5 carbon atoms, optionally substituted with an aryl group, R$_4$ is a protecting group of amine functions, such as Boc, R$_7$=R$_8$=H.

The invention relates more particularly to compounds of formula (IV-2) as defined above in which:

R$_1$ is OH, OCH$_3$, NHCH$_2$C$_6$H$_5$, NHC$_6$H$_5$, NHC$_6$H$_4$OH, or NH(CH$_2$)$_4$NHBoc,

R$_2$ is H, CH$_3$, CH$_2$—CH—(CH$_3$)$_2$, CH$_2$CONH$_2$, (CH$_2$)$_3$NHC(=NH)NH$_2$, or (CH$_2$)$_3$NZC(=NH)NHZ, or (CH$_2$)$_4$NHBoc,

R$_3$ is H, or CH$_2$—C$_6$H$_5$,

R$_4$ is Boc.

The invention concerns more particularly compounds of formula (IV-2) as defined above in which:

R$_1$ is NHCH$_2$C$_6$H$_5$, R$_2$ is H, R$_3$ is CH$_2$—C$_6$H$_5$, and R$_4$ is Boc (compound PSV11R), or R$_1$ is OH, R$_2$ is H, R$_3$ is CH$_2$—C$_6$H$_5$, and R$_4$ is Boc (compound NR35), or R$_1$ is NHC$_6$H$_5$, R$_2$ is CH$_3$, R$_3$ is CH$_2$—C$_6$H$_5$, and R$_4$ is Boc (compound SP303r2), or R$_1$ is NHCH$_2$C$_6$H$_5$, R$_2$ is CH$_3$, R$_3$ is CH$_2$—C$_6$H$_5$, and R$_4$ is Boc (compound SP304R), or R$_1$ is NHC$_6$H$_4$OH, R$_2$ is CH$_3$, R$_3$ is CH$_2$—C$_6$H$_5$, and R$_4$ is Boc (compound SP313P), or R$_1$ is NH(CH$_2$)$_4$NHBoc, R$_2$ is CH$_3$, R$_3$ is CH$_2$—C$_6$H$_5$, and R$_4$ is Boc (compound SP305R), or R$_1$ is OCH$_3$, R$_2$ is CH$_3$, R$_3$ is CH$_2$—C$_6$H$_5$, and R$_4$ is Boc (compound NR36), or R$_1$ is OCH$_3$, R$_2$ is CH$_3$, R$_3$ is H, and R$_4$ is Boc (compound NR40), or R$_1$ is NHC$_6$H$_5$, R$_2$ is CH$_2$—CH—(CH$_3$)$_2$, R$_3$ is CH$_2$—C$_6$H$_5$, and R$_4$ is Boc (compound A424P), or R$_1$ is NHCH$_2$C$_6$H$_5$, R$_2$ is CH$_2$—CH—(CH$_3$)$_2$, R$_3$ is CH$_2$—C$_6$H$_5$, and R$_4$ is Boc (compound A414P), or R$_1$ is NHC$_6$H$_4$OH, R$_2$ is CH$_2$—CH—(CH$_3$)$_2$, R$_3$ is CH$_2$—C$_6$H$_5$, and R$_4$ is Boc (compound A418P), or R$_1$ is NH(CH$_2$)$_4$NHBoc, R$_2$ is CH$_2$—CH—(CH$_3$)$_2$, R$_3$ is CH$_2$—C$_6$H$_5$, and R$_4$ is Boc (compound SP296P), or R$_1$ is NHC$_6$H$_5$, R$_2$ is CH$_2$CONH$_2$, R$_3$ is CH$_2$—C$_6$H$_5$, and R$_4$ is Boc (compound SP314C2), or R$_1$ is NHCH$_2$C$_6$H$_5$, R$_2$ is CH$_2$CONH$_2$, R$_3$ is CH$_2$—C$_6$H$_5$, and R$_4$ is Boc (compound A416), or R$_1$ is NHC$_6$H$_4$OH, R$_2$ is CH$_2$CONH$_2$, R$_3$ is CH$_2$—C$_6$H$_5$, and R$_4$ is Boc (compound SP318C), or R$_1$ is NH(CH$_2$)$_4$NHBoc, R$_2$ is CH$_2$CONH$_2$, R$_3$ is CH$_2$—C$_6$H$_5$, and R$_4$ is Boc (compound SP323C2), or R$_1$ is NHC$_6$H$_5$, R$_2$ is (CH$_2$)$_3$NHC(=NH)NH$_2$, R$_3$ is H, and R$_4$ is Boc (compound SP325), or R$_1$ is NHC$_6$H$_4$OH, R$_2$ is (CH$_2$)$_3$NHC(=NH)NH$_2$, R$_3$ is H, and R$_4$ is Boc (compound SP324), or R$_1$ is NHC$_6$H$_5$, R$_2$ is (CH$_2$)$_3$NZC(=NH)NHZ, R$_3$ is CH$_2$—C$_6$H$_5$, and R$_4$ is Boc (compound SP310C), or R$_1$ is NHCH$_2$C$_6$H$_5$, R$_2$ is (CH$_2$)$_3$NZC(=NH)NHZ, R$_3$ is CH$_2$—C$_6$H$_5$, and R$_4$ is Boc (compound SP315C2), or R$_1$ is NHC$_6$H$_4$OH, R$_2$ is (CH$_2$)$_3$NZC(=NH)NHZ, R$_3$ is CH$_2$—C$_6$H$_5$, and R$_4$ is Boc (compound SP320P2), or R$_1$ is NH(CH$_2$)$_4$NHBoc, R$_2$ is (CH$_2$)$_3$NZC(=NH)NHZ, R$_3$ is CH$_2$—C$_6$H$_5$, and R$_4$ is Boc (compound SP311C), or R$_1$ is NHC$_6$H$_5$, R$_2$ is (CH$_2$)$_4$NHBoc, R$_3$ is CH$_2$—C$_6$H$_5$, and R$_4$ is Boc (compound SP306P), or R$_1$ is NHCH$_2$C$_6$H$_5$, R$_2$ is (CH$_2$)$_4$NHBoc, R$_3$ is CH$_2$—C$_6$H$_5$, and R$_4$ is Boc (compound SP307P), or R$_1$ is NHC$_6$H$_4$OH, R$_2$ is (CH$_2$)$_4$NHBoc, R$_3$ is CH$_2$—C$_6$H$_5$, and R$_4$ is Boc (compound SP319P), or R$_1$ is NH(CH$_2$)$_4$NHBoc, R$_2$ is (CH$_2$)$_4$NHBoc, R$_3$ is CH$_2$—C$_6$H$_5$, and R$_4$ is Boc (compound SP308P).

or R$_1$ is OH, R$_2$ is CH$_3$, R$_3$ is CH$_2$—C$_6$H$_5$, and R$_4$ is Boc (compound NR66).

or R$_1$ is OH, R$_2$ is CH$_3$, R$_3$ is H, and R$_4$ is Boc (compound NR68).

The invention relates more particularly to compounds SP313P, NR$_{40}$, SP325, and SP324, as preferred compounds of formula (IV-2).

The invention also concerns compounds as defined above, of the following formula (IV-3):

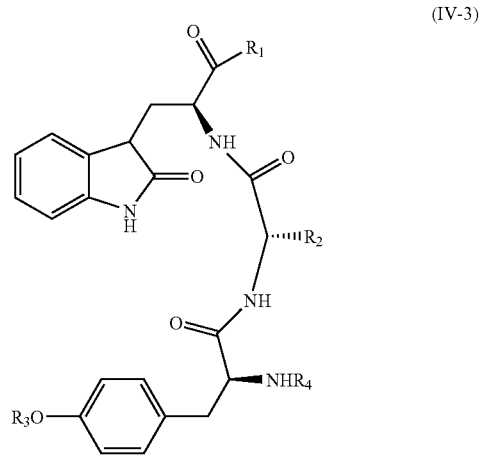

corresponding to compounds of formula (IV) in which:
the bond d is present, and R$_9$ is an oxygen atom O,
n$_0$=0, R$_1$ is OH, or a group OR$_{10}$ in which R$_{10}$ is a linear or branched alkyl group from 1 to 5 carbon atoms, or a group of formula NH—(CH$_2$)$_{n1}$—R$_1$ in which n$_1$=0, or an integer from 1 to 5, and R$_1$ is an aryl group, possibly substituted, R$_2$ is H, or a linear or branched alkyl group from 1 to 5 carbon atoms, or a group of formula (CH$_2$)$_{n2}$—(CO)$_{n3}$—NR$_{13}$R$_{14}$, in which n$_2$ is an integer from 1 to 5, n$_3$=0 or 1, and R$_{13}$ and R$_{14}$, independently from one another, are H, or a protecting group of amine functions, such as Boc, or Z, or a group of formula C(=NH)NHR$_{15}$ in which R$_{15}$ is H or a protecting group of amine functions, such as Boc, or Z, mentioned above, R$_3$ is H, or a linear or branched alkyl group from 1 to 5 carbon atoms, optionally substituted with an aryl group, R$_4$ is a protecting group of amine functions, such as Boc, R$_7$=R$_8$=H.

The invention relates more particularly to compounds of formula (IV-3) as defined above in which:

R$_1$ is OH, OCH$_3$, NHCH$_2$C$_6$H$_5$, or NHC$_6$H$_5$,

R$_2$ is H, CH$_3$, CH$_2$—CH—(CH$_3$)$_2$, (CH$_2$)$_3$NZC(=NH)NHZ, or (CH$_2$)$_4$NHBoc, $R_3$ is H, or $CH_2$—$C_6H_5$,
$R_4$ is Boc.

The invention also relates more particularly to compounds of formula (IV-3) as defined above in which:
  $R_1$ is $NHC_6H_5$, $R_2$ is $(CH_2)_3NZC(\!=\!NH)NHZ$, $R_3$ is $CH_2$—$C_6H_5$, and $R_4$ is Boc (compound CV11),
  $R_1$ is $NHC_6H_5$, $R_2$ is $(CH_2)_4NHBoc$, $R_3$ is $CH_2$—$C_6H_5$, and $R_4$ is Boc (compound CV12),
  $R_1$ is $NHC_6H_5$, $R_2$ is $CH_3$, $R_3$ is $CH_2$—$C_6H_5$, and $R_4$ is Boc (compound CV13),
  $R_1$ is $NHC_6H_5$, $R_2$ is $CH_2$—$CH$—$(CH_3)_2$, $R_3$ is $CH_2$—$C_6H_5$, and $R_4$ is Boc (compound JV602),
  $R_1$ is $NHCH_2C_6H_5$, $R_2$ is H, $R_3$ is $CH_2$—$C_6H_5$, and $R_4$ is Boc (compound NR15),
  $R_1$ is $OCH_3$, $R_2$ is H, $R_3$ is $CH_2$—$C_6H_5$, and $R_4$ is Boc (compound NR38),
  $R_1$ is $NHCH_2C_6H_5$, $R_2$ is $(CH_2)_3NZC(\!=\!NH)NHZ$, $R_3$ is $CH_2$—$C_6H_5$, and $R_4$ is Boc (compound NR16),
  $R_1$ is $OCH_3$, $R_2$ is $CH_3$, $R_3$ is $CH_2$—$C_6H_5$, and $R_4$ is Boc,
  $R_1$ is OH, $R_2$ is $CH_3$, $R_3$ is $CH_2$—$C_6H_5$, and $R_4$ is Boc,
  $R_1$ is OH, $R_2$ is $CH_3$, $R_3$ is H, and $R_4$ is Boc,
  $R_1$ is $OCH_3$, $R_2$ is $CH_3$, $R_3$ is H, and $R_4$ is Boc.

The invention relates more particularly to compounds CV12, CV13, $NR_{15}$, and $NR_{38}$, as preferred compounds of formula (IV-3).

Advantageously compounds of formula (II), (III), (IV-1), (IV-2), and (IV-3) as defined above are obtained according to the following retrosynthetic scheme:

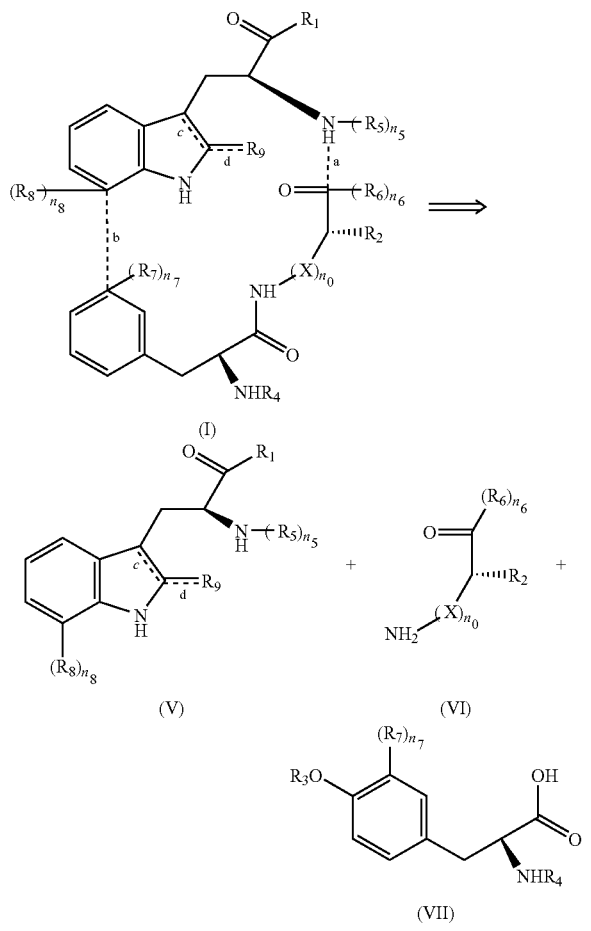

Synthons (V), (VI) and (VII) were assembled according to standard peptide synthesis (Bodansky, M.; Bodansky, A., *The practice of peptide synthesis*. Springer Verlag, 1995) or according to techniques of biaryl synthesis (Hassan, J.; Sevignon, M.; Gozzi, C.; Schulz, E.; Lemaire, M., *Chem. Rev.* 2002, 102, (5), 1359-1469). The following reaction pathways were used:

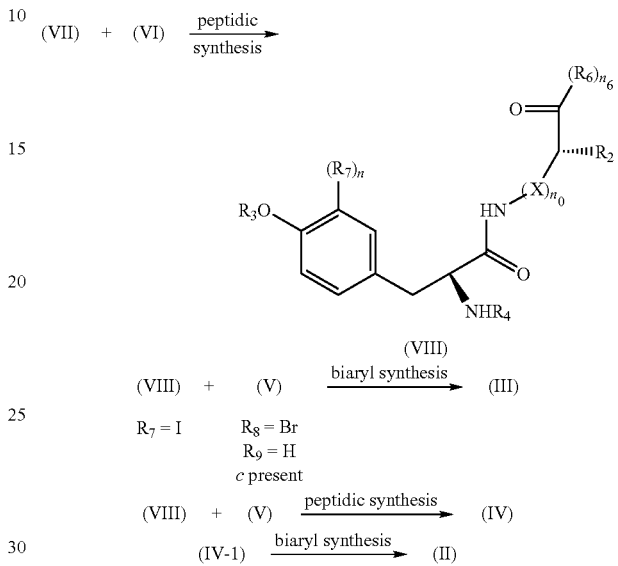

The invention will be further illustrated with the detailed description which follows of the synthesis and the biological properties of compounds of the invention.

I) Preparation of Starting Material

Synthons V and VIII

A) Preparation of 7-bromotryptophane derivatives

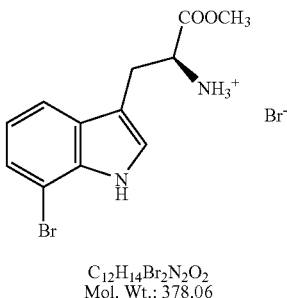

$C_{12}H_{14}Br_2N_2O_2$
Mol. Wt.: 378.06

HCl, (7-bromo)Trp-$OCH_3$ prepared according to Berthelot, A.; Piguel, S.; Le Dour, G.; Vidal, J., Synthesis of macrocyclic peptide analogues of proteasome inhibitor TMC-95A. *J. Org. Chem.* 2003, 68, (25), 9835-9838.

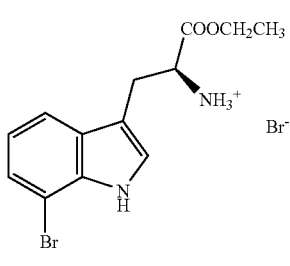

C₁₃H₁₆Br₂N₂O₂
Mol. Wt.: 392.09

HCl, (7-bromo)Trp-OEt (7-bromo)Trp(Boc)-OtBu (55 mg, 0.13 mmol, prepared according to Berthelot, A.; Piguel, S.; Le Dour, G.; Vidal, J., Synthesis of macrocyclic peptide analogues of proteasome inhibitor TMC-95A. J. Org. Chem. 2003, 68, (25), 9835-9838) was dissolved in a 3 M solution of anhydrous HCl in EtOH (0.5 mL). Evaporation of the solvent to dryness gave the crude HCl, (7-bromo)Trp-OEt (45 mg, 100%) as a white solid which was used without further purification. $^1$H NMR (200 MHz, D₂O) δ 1.05 (t, J=7.1 Hz, 3H, CH₃), 3; 36 (d, J=6.4 Hz, 2H, CH₂), 4.21 (q, J=7.1 Hz, 2H, CH₂(Et)), 4.31 (t, J=6.1 Hz, 1H, CH), 6.99 (t, J=7.7 Hz, 1H, H5), 7.26 (s, 1H, H2), 7.36 (d, J=7.7 Hz, 1H, H6) and 7.49 (d, J=7.7 Hz, 1H, H4). $^{13}$C NMR (75 MHz, CD₃OD) δ 14.3 (CH₃), 27.6 (CH₂(Et)), 54.7 (CHα), 63.7 (CH₂), 105.9 (C(7)), 109.1 (C(3)), 118.5 (CH), 121.6 (CH), 125.5 (CH), 126.9 (CH), 129.9 (C), 136.6 (C) and 170.3 (CO).

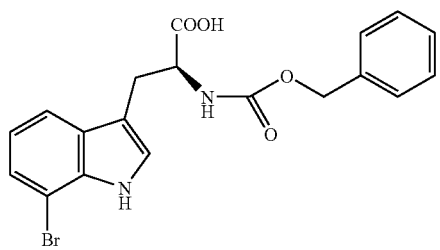

C₁₉H₁₇BrN₂O₄
Mol. Wt.: 417.25

Z-(7-bromo)Trp-OH

To a solution of (7-bromo)Trp(Boc)-OtBu (347 mg, 0.79 mmol, prepared according to Berthelot, A.; Piguel, S.; Le Dour, G.; Vidal, J., Synthesis of macrocyclic peptide analogues of proteasome inhibitor TMC-95A. J. Org. Chem. 2003, 68, (25), 9835-9838.), in DMF (2 mL) cooled at 0° C. was added ZOSu (217 mg, 0.87 mmol). The resulting mixture was stirred 1 h at 0° C. and 1 h 30 at room temperature before concentration of the solvents. The residue was then diluted in CH₂Cl₂ and washed with water. The organic layer was then dried over Na₂SO₄ and the solvent was removed in vacuo. Purification by column chromatography (10% AcOEt/heptane) gave Z-(7-bromo)Trp(Boc)-OtBu as a light yellow oil (435 mg, 96%). Rf 0.44 (20% AcOEt/heptane). $^1$H NMR (300 MHz, CD₃Cl₃) δ 1.39 (s, 9H, tBu), 1.65 (s, 9H, 3CH₃(Boc)), 3.2 (d, J=5.5 Hz, 2H, CH₂), 4.61-4.64 (m, 1H, CH), 5.13 (AB, J=12.2 Hz, 2H, CH₂(Z)), 5.36 (broad d, J=7.8 Hz, 1H, NH(Z)), 7.06 (t, J=7.8 Hz, 1H, H5), 7.32-7.37 (m, 6H, 5 aromatic H (Z) and H2) and 7.49-7.55 (m, 2H, H4 and H6). Then, Z-(7-bromo)Trp(Boc)-OtBu (775 mg, 1.35 mmol) was dissolved in a 3 M solution of anhydrous HCl in AcOEt (3 mL). Evaporation of the solvent to dryness gave the crude Z-(7-bromo)Trp-OH (564 mg, 100%) which was used without further purification. $^1$H NMR (200 MHz, CD₃OD) δ 3.14 (dd, J=14.4 Hz, J=8 Hz, 1H) and 3; 32 (dd, J=14.4 Hz, J=5.6 Hz, 1H) CH₂, 4.54 (dd, J=8 Hz, J=5.6 Hz, 1H, CH), 5.05 (d, J=2.6 Hz, 2H, CH₂(Z)), 6.94 (t, J=7.8 Hz, 1H, H5), 7.17 (s, 1H, H2), 7.27-7.39 (m, 6H, 5 aromatic H(Z) and H6) and 7.53 (d, J=7.8 Hz, 1H, H4). $^{13}$C NMR (50 MHz, CD₃OD) δ 29.2 (CH₂), 56.6 (CHα), 57.9 (CH₂ Z), 105.9 (C), 112.9 (C), 119.2 (CH), 121.5 (CH), 125.4 (CH), 126.1 (CH), 129.1 (CH(Z)), 129.3 (CH(Z)), 129.8 (CH(Z)), 130.8 (C(Z)), 136.8 (C), 138.5 (C), 158.7 (C(Z)) and 175.8 (C).

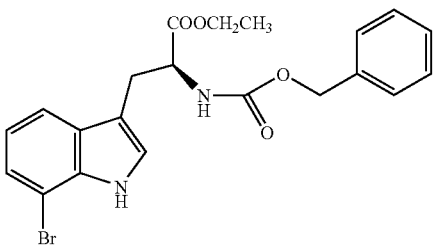

C₂₁H₂₁BrN₂O₄
Mol. Wt.: 445.31

Z-(7-bromo)Trp-OEt

Z-7-bromo-Trp(Boc)-OtBu (2.69 g, 4.69 g, obtained as described for Z-(7-bromo)Trp-OH) was dissolved in a HCl/AcOEt/EtOH mixture and allowed to react for 21 h. Evaporation of the solvent to dryness gave the crude Z-(7-bromo)Trp-OEt which was purified by flash chromatography on silica gel (3% MeOH/CH₂Cl₂) (1.44 g, 70%). $^1$H NMR (300 MHz, CDCl₃) δ 1.21 (t, J=7.1 Hz, 3H, CH₃), 3.31 (m, 2H, CH₂ Trp), 4.11 (m, 2H, CH₂ OEt), 4.71 (m, 1H, CHα), 5.09 and 5.16 (AB system, J=12.2 Hz, 2H), 5.33 (d, J=8.0 Hz, 1H, NHZ), 6.98 (t, J=7.8 Hz, 1H), 7.05 (d, J=2.0 Hz, 1H), 7.34 (m, 6H), 7.49 (d, J=7.8 Hz, 1H), 8.20 (s, 1H, indolic NH). $^{13}$C NMR (75 MHz, CDCl₃) δ 14.5 (CH₃), 28.6 (CH₂ Trp), 54.9 (CHα), 62.0 (CH₂), 67.3 (CH₂), 105.2 (C), 111.8 (C), 118.4 (CH), 121.2 (CH), 123.8 (CH), 124.9 (CH), 128.5 (CH), 128.6 (CH), 128.9 (CH), 129.2 (C), 135.2 (C), 136.7 (C), 156.1 (CO Z), 172.1 (CO ester). Anal. Calcd. for C₂₁H₂, BrN₂O₄: C, 56.64; H, 4.75; N, 6.29. Found: C, 57.29; H, 5.03; N, 5.93.

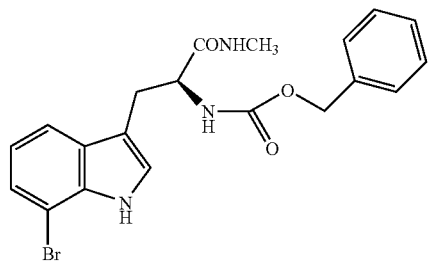

C₂₀H₂₀BrN₃O₃
Mol. Wt.: 430.3

Z-(7-bromo)Trp-NHMe

To a solution of Z-(7-bromo)Trp-OH (784 mg, 1.88 mmol) in THF (10 mL) cooled at 0° C. was added dropwise NEt₃ (315 μL, 2.26 mmol) and ethyl chloroformate (215 μL, 2.26 mmol). The resulting solution was stirred 20 nm before methylamine 2M solution in THF (3 mL, 6 mmol) was added. The mixture was stirred a further 2 h 30 and evaporated to dryness. The residue was suspended in water before being collected by filtration. Z-(7-bromo)Trp-NHMe was obtained as a white solid (683 mg, 85%). mp(dec) 200° C. ¹H NMR (200 MHz, CD₃OD) δ 2.61 (d, J=4.5 Hz, 3H, CH₃), 2.91 (dd, J=15.1 Hz, J=4 Hz, 1H) and 3; 10 (dd, J=15.1 Hz, J=10.1 Hz, 1H)CH₂, 4.14-4.31 (m, 1H, CH), 4.96 (s, 2H, CH₂(Z)), 6.96 (t, J=7.7 Hz, 1H, H5), 7.23-7.41 (m, 6H, 5 aromatic H(Z) and H2), 7.46 (d, J=7.7 Hz, 1H, H6), 7.67 (d, J=7.7 Hz, 1H, H4), 8.0 (broad s, 1H, NH(Me)) and 11.09 (broad s, 1H, NH). ¹³C NMR (50 MHz, DMSO-d⁶) δ 26.0 (CH₃), 28.4 (CH₂), 56.5 (CHα), 65.6 (CH₂ Z), 104.5 (C), 112.2 (C), 118.5 (CH), 120.1 (CH), 123.8 (CH), 125.6 (CH), 127.8 (CH(Z)), 128.0 (CH (Z)), 128.6 (CH(Z)), 129.4 (C(Z)), 134.7 (C), 137.4 (C), 156.2 (C(Z)) and 172.4 (C). HRMS (FAB) calcd for C₂₀H₂₀BrN₃O₃ [M+H⁺] 430.0766. Found 430.0766.

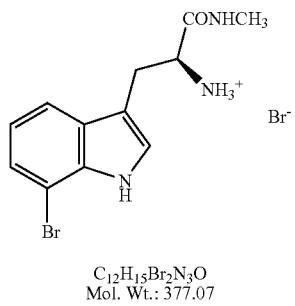

C₁₂H₁₅Br₂N₃O
Mol. Wt.: 377.07

HBr, (7-bromo)Trp-NHMe

Z-(7-bromo)Trp-NHMe (376 mg, 0.87 mmol) was dissolved in an HBr 45% w/v solution in acetic acid (1 mL) and was stirred at room temperature for 8 h and evaporated to dryness. The residue, solubilized in water, was lyophilized and gave HBr, (7-bromo)Trp-NHMe (330 mg, 100%) as a brown solid which was used without purification. ¹H NMR (200 MHz, DMSO-d⁶) δ 2.64 (d, 2H, J=5 Hz, CH₃), 3.12-3.21 (m, 2H, CH₂), 3.92 (m, 1H, CH), 7.0 (t, J=7.7 Hz, 1H, H5), 7.29 (d, J=2.4 Hz, 1H, H2), 7.35 (d, J=7.7 Hz, 1H, H6), 7.67 (d, J=7.7 Hz, 1H, H4), 8.09 (broad s, 3H, NH₃⁺), 8.48 (broad d, J=5 Hz, 1H, NH(Me)) and 11.28 (broad s, 1H, NH).

B) Preparation of Tryptophane Derivatives

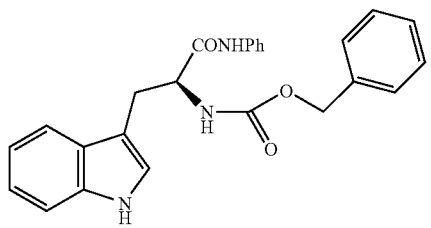

C₂₅H₂₃N₃O₃
Mol. Wt.: 413.47

Z-Trp-NHPh

To a solution of Z-Trp-OH (2 g, 5.9 mmol) in THF (88 mL) at 5° C. were added aniline (540 μL, 5.9 mmol) and DCC (1.6 g, 7.7 mmol). The reaction was allowed to warm up to room temperature overnight. The solvent was evaporated off and the crude was triturated with ethyl acetate (50 mL). After filtration, the organic phase was successively washed with aqueous 5% KHSO₄, aqueous 10% KHCO₃, brine and was dried over Na₂SO₄. The solvent was removed in vacuo. The crude amide was purified by precipitation in methanol/pentane to give a white amorphous solid (1.7 g, 69%). ¹H NMR (300 MHz, CDCl₃) δ 3.25 (dd, J=14.4 Hz, J=8 Hz, 1H, CH₂), 3.46 (dd, J=14.4 Hz, J=5.3 Hz, 1H, CH₂), 4.67 (m, 1H, CHα), 5.12 (m, 2H, CH₂ (Z)), 5.63 (broad s, 1H, NHZ), 7.06-7.72 (m, 16H, 15 aromatic H, NH amide), 8.09 (s, 1H, NH indole). ¹³C NMR (75 MHz, CDCl₃) δ 28.6 (CH₂ Trp), 56.1 (CHα), 67.2 (CH₂ (Z)), 111.4, 118.8, 119.9, 120.1, 122.4, 123.4, 124.5, 127.1, 128.1, 128.3, 128.6, 128.9, 136, 136.2, 137.1 (20 aromatic C), 156 (CO carbamate), 169.7 (CO amide). Anal. Calcd. for C₂₅H₂₃N₃O₃: C, 72.62; H, 5.61; N, 10.16. Found: C, 72.75; H, 5.58; N, 9.95.

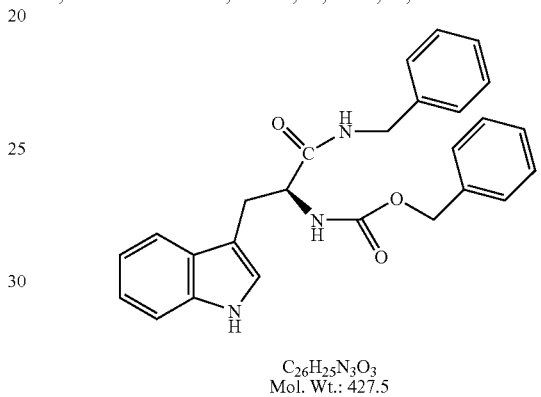

C₂₆H₂₅N₃O₃
Mol. Wt.: 427.5

Z-Trp-NHCH₂Ph

Same procedure as above with Z-Trp-OH (2 g, 5.9 mmol), benzylamine (645 μL, 5.9 mmol), DCC (1.58 g, 7.65 mmol) and THF (88 mL). A white solid was obtained after precipitation in methanol/pentane (777 mg, 31%). ¹H NMR (300 MHz, CDCl₃) δ 3.18 (dd, J=14.3 Hz, J=8.1 Hz, 1H, CH₂), 3.39 (dd, J=14.3 Hz, J=4.9 Hz, 1H, CH₂), 4.3 (m (AB), 2H, CH₂ (Bn)), 4.53 (m, 1H, CHα), 5.11 (s, 2H, CH₂ (Z)), 5.52 (m, 1H, NH), 5.90 (m, 1H, NH), 6.91-7.70 (m, 15 aromatic H), 8.01 (s, 1H, NH indole). ¹³C NMR (75 MHz, CDCl₃) δ 28.7 (CH₂ Trp), 43.4 (CH₂), 56.1 (CHα), 67 (CH₂ (Z)), 111.2, 118.7, 119.7, 122.2, 123.2, 123.4, 127.2, 127.3, 127.6, 128, 128.2, 128.5, 136.1, 136.2, 137.5, 137.6 (20 aromatic C), 156 (CO carbamate), 171.2 (CO amide). Anal. Calcd. for C₂₆H₂₅N₃O₃, 0.75H₂O: C, 70.81; H, 6.06; N, 9.53. Found: C, 70.84; H, 6.80; N, 9.21.

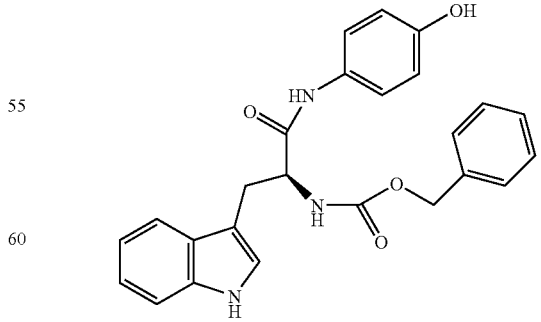

C₂₅H₂₃N₃O₄
Mol. Wt.: 429.47

Z-Trp-NH(4-OH)Ph: Same procedure as above with Z-Trp-OH (0.5 g, 1.48 mmol), 4-aminophenol (162 mg, 1.48 mmol), DCC (396 mg, 1.92 mmol) and THF (20 mL). A white solid was isolated after purification by flash chromatography on silica gel (0-3% MeOH/CH$_2$Cl$_2$) (493 mg, 77%). $^1$H NMR (300 MHz, MeOD) δ 3.25 (dd, J=14.4 Hz, J=8 Hz, 1H, CH$_2$), 3.46 (dd, J=14.4 Hz, J=5.3 Hz, 1H, CH$_2$), 4.53 (m, 1H, CHα), 5.06 (m, 2H, CH$_2$ (Z)), 6.7 (d, J=8.9 Hz, 2 aromatic H), 7 (t, J=7 Hz, 1 aromatic H), 7.07-7.35 (m, 10 aromatic H), 7.6 (d, J=7.8 Hz, 1 aromatic H). $^{13}$C NMR (75 MHz, MeOD) δ 32.3 (CH$_2$ Trp), 60.4 (CHα), 70.2 (CH$_2$ (Z)), 113.3, 114.8, 118.6, 122, 122.4, 125, 126.5, 127.2, 131.3, 131.5, 133.5, 140.5, (20 aromatic C), 158.1 (CO carbamate), 175.2 (CO amide). Anal. Calcd. for C$_{25}$H$_{23}$N$_3$O$_4$, 0.25H$_2$O: C, 69.19; H, 5.46; N, 9.68. Found: C, 69.34; H, 5.32; N, 9.61.

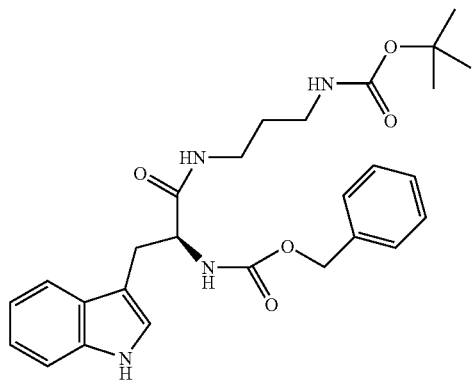

C$_{28}$H$_{36}$N$_4$O$_5$
Mol. Wt.: 508.27

Z-Trp-NH(CH$_2$)$_4$NHBoc: To a solution of Z-Trp-OH (1 g, 3 mmol) in DMF (16 mL) at 0° C. were added HOBt (611 mg, 4.52 mmol), EDC (636 mg, 3.32 mmol) and NEt$_3$ (0.5 mL). The reaction was stirred for 30 min followed by dropwise addition of a solution of amine NH$_2$(CH$_2$)$_4$NHBoc prepared according to: Krapcho, A. P.; Kuell, C. S., Mono-protected diamines. N-tert-butoxycarbonyl-α,ω-alkanediamines from α,ω-alkanediamines. Synthetic Communications 1990, 20, (16), 2559-2564), (630 mg, 3.34 mmol) in DMF (4 mL) and NEt$_3$ (0.5 mL). The reaction mixture was allowed to warm up to room temperature overnight and then concentrated. The resulting residue was diluted with CH$_2$Cl$_2$ and successively washed with water, aqueous NaHCO$_3$ (1 M), aqueous KHSO$_4$ (0.5 M) and brine. The organic phase was dried over Na$_2$SO$_4$ and the solvent was removed in vacuo. The crude was triturated with CH$_2$Cl$_2$ and a white solid was collected by filtration (773 mg). The mother liquor was concentrated down and triturated once more with CH$_2$Cl$_2$/pentane. A second batch was isolated as a white solid (482 mg, 82% overall yield). $^1$H NMR (300 MHz, CDCl$_3$) δ 1.18 (m, 4H, 2 CH$_2$), 1.48 (s, 9H, (CH$_3$)$_3$), 2.93-3.36 (m, 6H, CH$_2$ Trp, 2 CH$_2$N), 4.5 (m, 1H, CHα), 4.65 (m, 1H, NHBoc), 5.12 (m, 2H, CH$_2$ (Z)), 5.68 (m, 2 NH), 7.01 (s, 1 aromatic H), 7.11 (m, 1 aromatic H), 7.19 (t, J=7 Hz, 1 aromatic H), 7.32 (m, 6 aromatic H), 7.7 (m, 1 aromatic H), 9 (broad s, 1H, NH indole). $^{13}$C NMR (75 MHz, CDCl$_3$) δ 26.5, 27.6, 29 (2 CH$_2$, CH$_2$ Trp), 28.5 ((CH$_3$)$_3$), 39.1, 40.2 (CH$_2$NHCO, CH$_2$NHBoc), 55.8 (CHα), 67 (CH$_2$ (Z)), 79.5 (C(CH$_3$)$_3$), 110.2, 111.4, 118.8, 119.7, 122.1, 123.5, 127.2, 128.1, 128.2, 128.5, 136.2, 136.3 (14 aromatic C), 156.4 (CO carbamate), 171.3 (CO amide). Anal. Calcd. for C$_{28}$H$_{36}$N$_4$O$_5$, 0.25H$_2$O: C, 65.54; H, 7.16; N, 10.91. Found: C, 65.78; H, 7.17; N, 10.63.

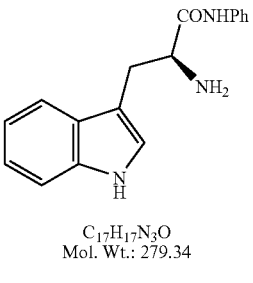

C$_{17}$H$_{17}$N$_3$O
Mol. Wt.: 279.34

Trp-NHPh: A Schlenk flask charged with Z-Trp-NHPh (1.7 g, 4.11 mmol) and 10% Pd/C (437.4 mg) was flushed under H$_2$ before adding MeOH/DMF (41 mL, 1/1). The reaction mixture was stirred under atmosphere of H$_2$ overnight followed by filtration through a pad of celite. The solvent was removed in vacuo and the crude was purified by flash column chromatography on silica gel (2-8% MeOH/CH$_2$Cl$_2$). The amine was isolated as a yellow solid (841 mg, 73%). mp 114-116° C. 1H NMR (300 MHz, CDCl$_3$) δ 1.89 (broad s, 2H, NH$_2$), 3.06 (dd, J=14.5 Hz, J=8.8 Hz, 1H, CH$_2$), 3.55 (dd, J=14.5 Hz, J=3.9 Hz, 1H, CH$_2$), 3.89 (dd, J=8.8 Hz, J=3.8 Hz, 1H, CHα), 7.06-7.41 (m, 7 aromatic H), 7.61 (d, J=7.9 Hz, 2 aromatic H), 7.72 (d, J=7.8 Hz, 1 aromatic H), 8.24 (broad s, 1H, NH amide), 9.48 (s, 1H, NH indole). 13C NMR (75 MHz, CDCl$_3$) δ 30.5 (CH$_2$ Trp), 56 (CHα), 111.4, 118.8, 119.5, 119.7, 122.3, 123.2, 124.1, 127.5, 129, 129.1, 136.5, 137.8 (14 aromatic C), 173.2 (CO amide).

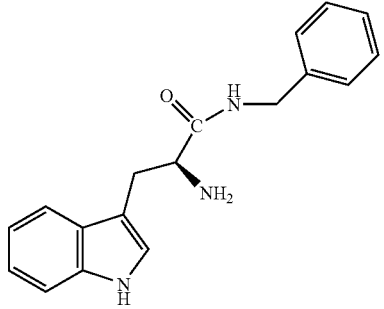

C$_{18}$H$_{19}$N$_3$O
Mol. Wt.: 293.36

Trp-NHCH$_2$Ph: Same procedure as above with Z-Trp-NHCH$_2$Ph (616 mg, 1.44 mmol), 10% Pd/C (153 mg) in MeOH/DMF (14.5 mL, 1/1). After purification by flash chromatography on silica gel (3-12% MeOH/CH$_2$Cl$_2$), Trp-NHCH$_2$Ph was isolated as a pale yellow oil (351 mg, 83%). $^1$H NMR (300 MHz, CDCl$_3$) δ 2.98 (dd, J=14.4 Hz, J=8.7 Hz, 1H, CH$_2$), 3.44 (dd, J=14.4 Hz, J=4.1 Hz, 1H, CH$_2$), 3.80 (dd, J=8.7 Hz, J=4.2 Hz, 1H, CHα), 4.46 (m, 2H, CH$_2$ (Bn)), 7.06 (d, J=2.1 Hz, 1 aromatic H), 7.13-7.36 (m, 7 aromatic H), 7.41 (d, J=8 Hz, 1 aromatic H), 7.61 (m, 1H, NH amide), 7.72 (d, J=7.8 Hz, 1 aromatic H), 8.3 (broad s, 1H, NH indole). $^{13}$C NMR (75 MHz, MeOD) δ 30.5 (CH$_2$ Trp), 42.7 (CH$_2$ Ph), 55.4 (CHα), 109.3, 111, 118.1, 118.5, 121.2, 123.5, 126.8, 127, 127.1, 127.4, 128, 128.1, 136.8, 138 (14 aromatic C), 174.6 (CO amide).

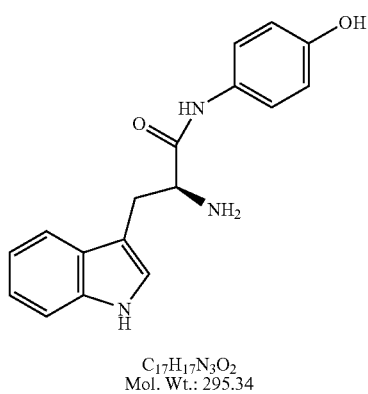

C₁₇H₁₇N₃O₂
Mol. Wt.: 295.34

Trp-NH(4-OH)Ph: Same procedure as above with Z-Trp-NHPhOH (208 mg, 0.48 mmol), 10% Pd/C (52 mg) in MeOH (5 mL). A light brown solid was obtained after precipitation in CH$_2$Cl$_2$/MeOH (85 mg, 59%). $^1$H NMR (300 MHz, MeOD) δ 3.09 (dd, J=14.1 Hz, J=6.9 Hz, 1H, CH$_2$), 3.25 (dd, J=14.1 Hz, J=6.2 Hz, 1H, CH$_2$), 3.73 (t, J=6.6 Hz, 1H, CHα), 6.71 (d, J=8.9 Hz, 2 aromatic H), 7 (t, J=8 Hz, 1 aromatic H), 7.1 (t, J=8 Hz, 1 aromatic H), 7.12 (s, 1 aromatic H), 7.21 (d, J=8.9 Hz, 2 aromatic H), 7.35 (d, J=8 Hz, 1 aromatic H), 7.64 (d, J=8 Hz, 1 aromatic H). $^{13}$C NMR (75 MHz, MeOD) δ 34.4 (CH$_2$ Trp), 59.6 (CHα), 113.3, 114.9, 118.7, 122, 122.4, 125, 126.2, 127.4, 131.3, 133.5, 140.5, 158.1 (14 aromatic C), 177 (CO amide). Anal. Calcd. for C$_{17}$H$_{17}$N$_3$O$_2$, 0.25H$_2$O: C, 67.86; H, 6.19; N, 13.96. Found: C, 67.96; H, 5.97; N, 14.13.

149d:

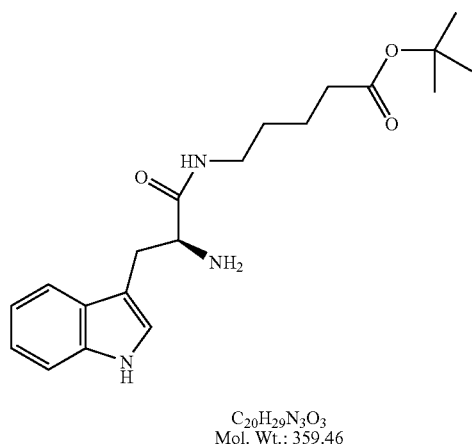

C₂₀H₂₉N₃O₃
Mol. Wt.: 359.46

Trp-NH(CH$_2$)$_4$NHBoc: Same procedure as above with Z-Trp-NH(CH$_2$)$_4$NHBoc (1.16 g, 2.28 mmol), 10% Pd/C (242 mg) in MeOH/DMF (10 mL, 1/1). After purification by flash chromatography on silica gel (4-25% MeOH/CH$_2$Cl$_2$), Trp-NH(CH$_2$)$_4$NHBoc was isolated as a white foam (701 mg, 82%). $^1$H NMR (300 MHz, CDCl$_3$) δ 1.39 (m, 4H, 2 CH$_2$), 1.46 (s, 9H, (CH$_3$)$_3$), 3-3.35 (m, 6H, CH$_2$ Trp, 2 CH$_2$N), 3.7 (m, 1H, CHα), 4.71 (m, 1H, NHBoc), 7.05 (d, J=2 Hz, 1 aromatic H), 7.1 (t, J=7.7 Hz, 1 aromatic H), 7.2 (m, 2H, 1 aromatic H, NH amide), 7.38 (d, J=7.9 Hz, 1 aromatic H), 7.65 (d, J=7.9 Hz, 1 aromatic H), 8.94 (broad s, 1H, NH indole). $^{13}$C NMR (75 MHz, CDCl$_3$) δ 26.9, 27.6, 30.8 (2 CH$_2$, CH$_2$ Trp), 28.5 ((CH$_3$)$_3$), 38.7, 40.3 (CH$_2$NHCO, CH$_2$NHBoc), 55.6 (CHα), 79.3 (C(CH$_3$)$_3$), 111.3, 111.4, 118.9, 119.5, 122, 123.3, 127.6, 136.4 (8 aromatic C), 156.2 (CO carbamate), 174.8 (CO amide).

C) Preparation of Oxotryptophane Derivatives

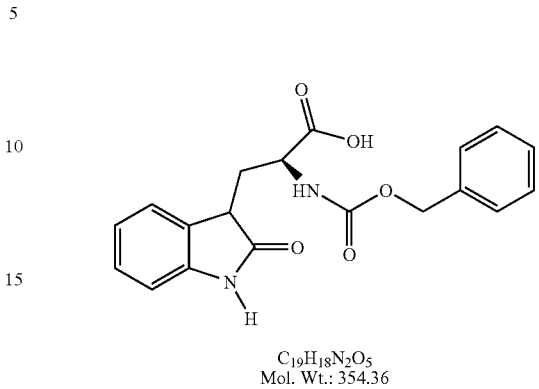

C₁₉H₁₈N₂O₅
Mol. Wt.: 354.36

L-Z-Trp[O]—OH: To a solution of L-H-Trp[O]—OH (2.55 g, 11.57 mmol, prepared according to: Labroo, R. B.; Cohen, L. A., Preparative separation of the diastereoisomers of dioxindolyl-L-alanine and assignment of stereochemistry at C-3. J. Org. Chem. 1990, 55, (16), 4901-4904) in DMF (11.5 mL) was added ZOSu (2.89 g, 11.6 mmol) and then NEt$_3$ (1.63 mL, 11.7 mmol). The solution was stirred for 4 h at room temperature and then was concentrated in vacuo. The resulting residue was triturated in 5% aqueous KHSO$_4$ (20 mL) and the resulting mixture was extracted with CH$_2$Cl$_2$ (3×25 mL). After drying of the organic phases on MgSO$_4$ and concentration in vacuo, L-Z-Trp[O]—OH was obtained as a beige solid (2.28 g, 55%). 1H NMR (300 MHz, DMSO-d6) (50/50 mixture of two diastereomers) δ 1.91-2.27 (m, 2H, CH$_2$ Trp), 3.42 (m, 1H, CH oxindole), 4.38 and 4.52 (two m, 1H, CHα dia 1 or dia 2), 5.05 (s, 2H, CH$_2$(Z)), 6.83 and 6.95 (two t, J=10 Hz and J=7.8 Hz, 1H, aromatic H of dia 1 or dia 2), 7.17 and 7.26 (two t, J=5.2 Hz and J=8.4 Hz, 1H, aromatic H of dia 1 or dia 2), 7.32-7.44 (m, 7H, aromatic H), 7.75 and 7.88 (two d, J=8 Hz and J=8.7 Hz, 1H, NH(Z) dia 1 or dia 2), 10.41 and 10.43 (two s, 1H, NH oxindole dia 1 or dia 2), 12.52 (broad s, 1H, acidic H). $^{13}$C NMR (75 MHz, DMSO-d6) (mixture of two diastereomers) δ 32.3 (CH$_2$), 41.5 and 42.1 (CH), 51.3 and 51.4 (CH), 65.4 and 65.5 (CH$_2$), 109.2 and 109.4 (CH), 121.2 and 121.32 (CH), 123.9 and 124.34 (CH), 127.6, 127.7 127.8, 128.3 (4 CH), 128.8 and 129.3 (C), 136.9 (C), 142.4 and 142.6 (C), 156.1 and 156.2 (C), 173.3 and 173.7 (C), 178.4 and 178.7 (C). Anal. Calcd. for C$_{19}$H$_{18}$N$_2$O$_5$, 1H$_2$O: C, 61.28; H, 5.41; N, 7.52. Found: C, 61.65; H, 4.91; N, 7.50.

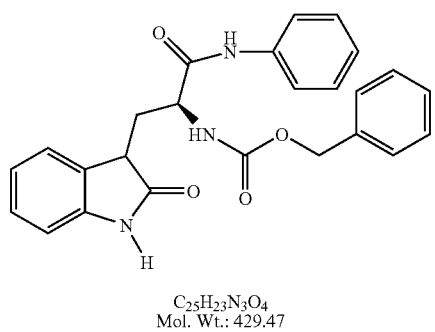

C₂₅H₂₃N₃O₄
Mol. Wt.: 429.47

L-Z-Trp[O]—NHPh: To a solution of crude L-Z-Trp[O]—OH (2.22 g, 6.26 mmol) in DME (12.5 mL) was added at 0° C. N-hydroxysuccinimide (0.757 g, 6.58 mmol) and dicyclohexylcarbodiimide (1.36 g, 6.58 mmol). After 15 min at 0° C., the mixture was stirred at room temperature overnight. The white solid was filtered and washed by DME (3×5 mL). The filtrate was concentrated in vacuo and the residue was dissolved in $CH_2Cl_2$ (50 mL). The resulting solution was washed by water (3×10 mL), dried over $Na_2SO_4$ and concentrated in vacuo to afford L-Z-Trp-OSu as a light yellow solid (2.56 g, 90%) which was used without further purification. To a solution of this crude product in DME (9 mL) was added freshly distilled aniline (0.62 mL, 6.80 mmol). After stirring at room temperature overnight, the solvent was evaporated in vacuo and the solid residue was suspended in 5% aqueous $KHSO_4$ (15 mL). After filtration, washing of the solid with water (2×10 mL), suspension of the solid in boiling 95% EtOH (20 mL) Z-Trp[O]—NHPh was obtained as a very fine white powder (1.29 g, 48% from L-Z-Trp[O]—OH). $^1H$ NMR (300 MHz, DMSO-$d_6$), (one diastereomer, which slowly underwent isomerization to a mixture of two diastereomers): δ 2.17 (m, 2H, $CH_2$ Trp), 3.50 (m, 1H, CH oxindole), 4.67 (m, 1H, CHα), 5.08 (broad s, 2H, $CH_2(Z)$), 6.86 (d, J=7.5 Hz, 1H, NH Z), 6.98 (t, J=7.6 Hz, H), 7.09 (t, J=7.2 Hz, 1H), 7.20 (t, J=7.6 Hz, 1H), 7.35-7.73 (m, 15H, 14 aromatic H and 1 NH(Z)), 10.1 (s, 1H, NH), 10.48 (s, 1H, NH). 13C NMR (75 MHz, DMSO-$d_6$) (mixture of two diastereomers) δ 32.8 ($CH_2$ Trp), 41.7 and 42.0 (CHγ), 53.1 (CHα), 65.4 and 65.5 ($CH_2$ Z), 109.2 and 109.4 (CH), 119.4 and 119.5 (CH), 121.3 (CH), 123.4 (CH), 124.0 and 124.7 (CH), 127.6, 127.7, 127.8, 128.3 and 128.6 (CH), 128.8 and 129.3 (C), 136.8 and 136.9 (C), 138.6 and 138.8 (C), 142.4 and 142.6 (C), 155.8 and 156.2 (C), 170.3 and 170.6 (C), 178.5 and 178.6 (C). Anal. Calcd. for $C_{25}H_{23}N_3O_4$, $0.5H_2O$: C, 68.48; H, 5.52; N, 9.58. Found: C, 68.47; H, 5.20; N, 9.40.

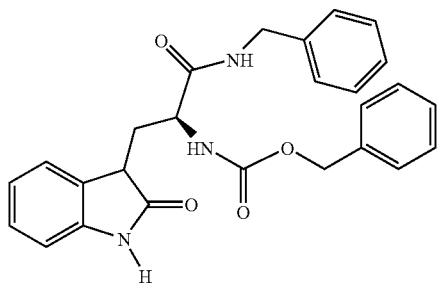

$C_{26}H_{25}N_3O_4$
Mol. Wt.: 443.49

L-Z-Trp[O]—$NHCH_2Ph$: Same procedure as above starting from Z-Trp-OSu (1.54 g, 3.29 mmol) and benzylamine (0.43 mL, 3.95 mmol) afforded L-Z-Trp[O]—$NHCH_2Ph$ after recrystallization in EtOH (0.775 g, 53%) as a white solid. $^1H$ NMR (300 MHz, DMSO-$d_6$), (60/40 mixture of two diastereomers in equilibrium): δ 1.88 and 2.11 (two m, 2H, $CH_2$ Trp), 3.45 (m, 1H, CH oxindole), 4.28 and 4.30 (two s, 2H, $NCH_2Ph$), 4.50 (m, 1H, CHα), 5.06 and 5.08 (two s, 2H, $CH_2(Z)$), 6.85 (t, J=7.6 Hz, 1H, aromatic H), 6.97 (t, J=7.2 Hz, 1H, aromatic H), 7.30 (m, 12H, 12 aromatic H), 7.65 and 7.87 (two d, J=8.9 Hz, 1H, NHZ), 8.53 (m, 1H, NH Bn), 10.46 and 10.48 (two s, 1H, NH oxindole). 13C NMR (75 MHz, DMSO-$d_6$) (mixture of two diastereomers) δ 33.0 and 33.2 ($CH_2$ β Trp), 42.1 (CHγ), 42.2 ($CH_2$ Bn), 52.5 and 52.6 (CHα), 65.5 and 65.6 ($CH_2$ Z), 109.2 and 109.4 (CH), 121.2 and 121.3 (CH), 124.0, 124.6, 126.6, 126.7, 126.9, 127.0, 127.1, 127.3, 127.4, 127.6, 127.7, 127.8, 128.1, 128.2 (aromatic CH), 128.3 and 129.0 (C), 136.9 (C), 139.2 and 139.4 (C), 142.4 and 142.5 (C), 155.8 and 156.2 (C), 171.3 and 171.5 (C), 178.6 and 178.7 (C). Anal. Calcd. for $C_{26}H_{25}N_3O_4$, $0.5H_2O$: C, 69.01; H, 5.79; N, 9.29. Found: C, 69.00; H, 5.76; N, 9.14.

HCl, L-Trp[O]—OMe: was prepared according to: Von Nussbaum, F.; Danishefsky, S. J. A rapid total synthesis of spirotryprostatin B: proof of its relative and absolute stereochemistry. Angew. Chem. Int. Ed. 2000, 39(12), 2175-2178.

D) Preparation of Dipeptides

Dipeptides were prepared using conventional peptide synthesis and were obtained according to Berthelot, A.; Piguel, S.; Le Dour, G.; Vidal, J., Synthesis of macrocyclic peptide analogues of proteasome inhibitor TMC-95A. J. Org. Chem. 2003, 68, (25), 9835-9838.

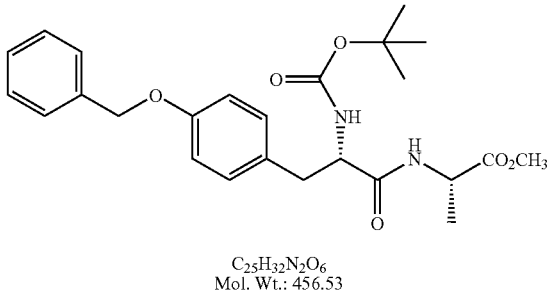

$C_{25}H_{32}N_2O_6$
Mol. Wt.: 456.53

N-Boc-Tyr(Bn)-Ala-OMe: described in the above article

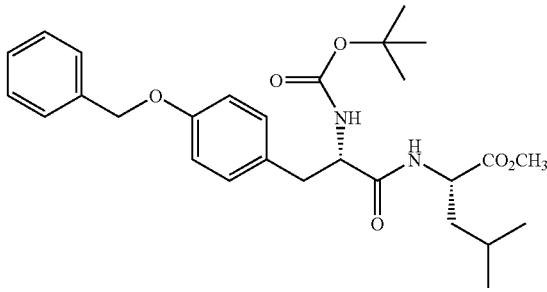

$C_{26}H_{38}N_2O_6$
Mol. Wt.: 498.61

N-Boc-Tyr(Bn)-Leu-OMe: described in the above article

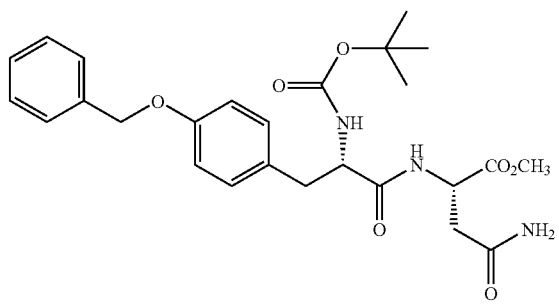

C<sub>26</sub>H<sub>33</sub>N<sub>3</sub>O<sub>7</sub>
Mol. Wt.: 499.56

N-Boc-Tyr(Bn)-Asn-OMe: described in the above article

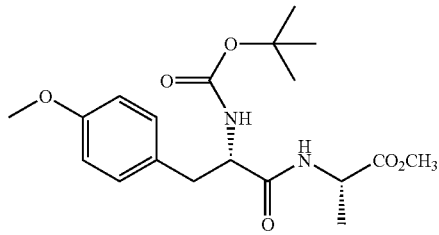

C<sub>19</sub>H<sub>28</sub>N<sub>2</sub>O<sub>6</sub>
Mol. Wt.: 380.44

N-Boc-Tyr(Me)-Ala-OMe: This compound was synthesized as described above from N-Boc-Tyr(Me)-OSu (1 g, 2.55 mmol), HCl, Ala-OMe (320.5 mg, 2.3 mmol) and NEt$_3$ (323 µL, 2.3 mmol). The dipeptide was obtained as a white solid (900 mg, 93%) and was used in the next step without further purification. $[\alpha]_D^{20}$ −9.02 (c 1, MeOH). $^1$H NMR (300 MHz, CDCl$_3$) δ 1.34 (d, J=7.1 Hz, 3H, CH$_3$ (Ala)), 1.46 (s, 9H, 3 CH$_3$ (Boc)), 3.02 (m, 2H, CH$_2$ (Tyr)), 3.73 (s, 3H, OCH$_3$), 3.8 (s, 3H, OCH$_3$), 4.31 (m, 1H, CH (Tyr)), 4.52 (m, 1H, CH (Ala)), 4.97 (broad s, 1H, NH (Boc)), 6.41 (d, J=7.1 Hz, 1H, NH), 6.86 (d, J=8.6 Hz, 2H, H3); 7.14 (d, J=8.7 Hz, 2H, H2). HRMS (ESI) calcd for C$_{19}$H$_{25}$N$_2$O$_6$Na [(M+Na)$^+$] 403.1845. Found 403.1847. These data are in agreement with those of Boger, D. L.; Zhou, J. N-Desmethyl Derivatives of Deoxybouvardin and RA-VII: Synthesis and Evaluation. J. Am. Chem. Soc. 1995, 117(28), 7364-78.

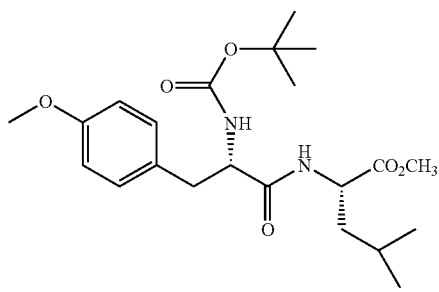

C<sub>22</sub>H<sub>34</sub>N<sub>2</sub>O<sub>6</sub>
Mol. Wt.: 422.52

N-Boc-Tyr(Me)-Leu-OMe. This compound was synthesized as described above from N-Boc-Tyr(Me)-OSu (1 g, 2.55 mmol), Leu-OMe.HCl (418 mg, 2.3 mmol) and NEt$_3$ (323 µL, 2.3 mmol). The dipeptide was obtained as a white solid (952 mg, 98%) and was used in the next step without further purification. $^1$H NMR (300 MHz, CDCl$_3$) δ 0.81 (m, 6H, 2 CH$_3$ (Leu)), 1.31 (s, 9H, 3 CH$_3$ (Boc)), 1.49 (m, 3H, CH and CH$_2$ (Leu)), 2.9 (m, 2H, CH$_2$ (Tyr)); 3.6 (s, 3H, OCH$_3$), 3.66 (s, 3H, OCH$_3$), 4.27 (m, 1H, CH (Tyr)), 4.48 (m, 1H, CHα (Leu)), 5.29 (m, 1H, NH (Boc)), 6.71 (d, J=8.4 Hz, 2H, H3), 6.75 (broad s, 1H, NH), 7.03 (d, J=8.4 Hz, 2H, H2). $^{13}$C NMR (50 MHz, CDCl$_3$) δ 21.8 (CH$_3$ (Leu)), 22.7 (CH$_3$ (Leu)), 24.6 (CH (Leu)), 28.2 (3 CH$_3$ (Boc)), 37.4 (CH$_2$ (Tyr)), 41.2 (CH$_2$ (Leu)), 50.7 (CHα(Leu)), 52 (OCH$_3$), 55 (OCH$_3$), 55.6 (CH (Tyr)), 79.7 (C (Boc)), 113.8 (C3), 128.7 (C1), 130.3 (C2), 155.4 (C4), 158.4 (CO (Boc)), 171.4 (CO amide), 172.9 (CO ester). HRMS (ESI) calcd for C$_{22}$H$_{34}$N$_2$O$_6$Na [(M+Na)$^+$] 445.2315. Found 445.2319.

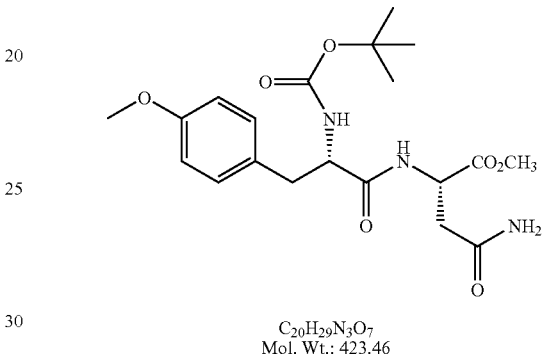

C<sub>20</sub>H<sub>29</sub>N<sub>3</sub>O<sub>7</sub>
Mol. Wt.: 423.46

N-Boc-Tyr(Me)-Asn-OMe: This compound was synthesized as described above from N-Boc-Tyr(Me)-OSu (1 g, 2.55 mmol), HCl, Asn-OMe (417 mg, 2.3 mmol) and NEt$_3$ (323 µL, 2.3 mmol). The dipeptide was obtained as a white solid (653 mg, 67%) which was used in the next step without further purification. $^1$H NMR (300 MHz, CDCl$_3$) δ 1.27 (s, 9H, 3 CH$_3$ (Boc)), 2.72-2.98 (m, 4H, 2 CH$_2$), 3.62 (s, 3H, OCH$_3$), 3.65 (s, 3H, OCH$_3$), 4.4 (m, 1H, CH (Tyr)), 4.7 (m, 1H, CH, (Asn)), 5.46 (broad s, 1H, NH (Boc)), 6.27 (broad s, 1H, NH$_2$), 6.5 (broad s, 1H, NH$_2$), 6.72 (d, J=8.5 Hz, H3), 7.03 (d, J=7.8 Hz, H2), 7.8 (broad s, 1H, NH). $^{13}$C NMR (300 MHz, CDCl$_3$) δ 28.2 (3 CH$_3$ (Boc)), 37 (CH$_2$ (Asn)), 37.6 (CH$_2$ (Tyr)), 49 (CH (Asn)), 57.6 (OCH$_3$), 55.1 (OCH$_3$), 55.5 (CH (Tyr)), 79.8 (C (Boc)), 113.8 (C3), 128.6 (C1), 130.4 (C2), 155.5 (C4), 158.4 (CO (Boc)), 171.6 (CO), 172 (CO), 172.7 (CO). HRMS (ESI) calcd for C$_{20}$H$_{29}$N$_3$O$_7$Na [(M+Na)$^+$] 446.1903. Found 446.1896.

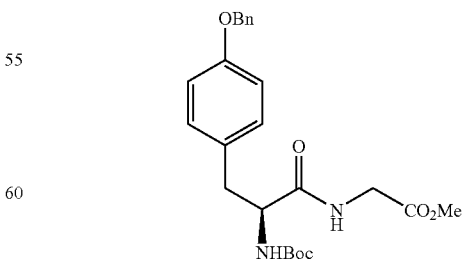

C<sub>24</sub>H<sub>30</sub>N<sub>2</sub>O<sub>6</sub>
Mol. Wt.: 442.5

N-Boc-Tyr(Bn)-Gly-OMe: Same procedure as for N-Boc-Tyr(Bn)-Ala-OMe with N-Boc-Tyr(Bn)-OSu (1 g, 2.13 mmol), Gly-OMe.HCl (268 mg, 2.14 mmol) and NEt₃ (0.3 mL, 2.16 mmol) in DMF (4 mL). The dipeptide was obtained as a white solid (946 mg, 100%) which was used in the next step without further purification. Recrystallization of dipeptide from hot iso-propanol afforded an analytical sample. mp 118-120° C. (lift 118-120° C. Flouret, G. R.; Arnold, W. H.; Cole, J. W.; Morgan, R. L.; White, W. F.; Hedlund, M. T.; Rippel, R. H. J. Med. Chem. 1973, 16(4), 369-73). $^1$H NMR (300 MHz, CDCl₃) δ 1.42 (s, 9H, (CH₃)₃), 3.05 (m, 2H, CH₂ Tyr), 3.75 (s, 3H, CO₂Me), 3.95 (dd, J=18.1 Hz, J=5 Hz, 1H, CH₂ Gly), 4.05 (dd, J=18.2 Hz, J=5.4 Hz, 1H, CH₂ Gly), 4.38 (m, 1H, CHα), 5.05 (broad s, 3H, NHBoc, CH₂ (Bn)), 6.47 (m, 1H, NH amide), 6.93 (d, J=8.5 Hz, 2 aromatic H), 7.15 (d, J=8.5 Hz, 2 aromatic H), 7.32-7.45 (m, 5 aromatic H). $^{13}$C NMR (75 MHz, CDCl₃) δ 28.3 ((CH₃)₃), 37.5 (CH₂ Tyr), 41.2 (CH₂ Gly), 52.3 (OCH₃), 55.7 (CHα), 70 (CH₂ (Bn)), 80.2 (C(CH₃)₃), 114.9, 127.5, 128, 128.3, 128.6, 128.9, 130.4, 137.1 (11 aromatic C), 155.5, 157.8 (Car-O, CO carbamate), 170, 171.9 (CO amide, CO ester).

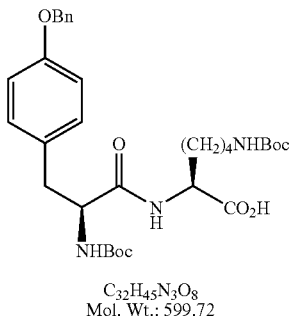

C₃₂H₄₅N₃O₈
Mol. Wt.: 599.72

N-Boc-Tyr(Bn)-Lys(Boc)-OH: Same procedure as above with N-Boc-Tyr(Bn)-OSu (1 g, 2.13 mmol), H-Lys(Boc)-OH (550 mg, 2.23 mmol) and a few drops of NEt₃ in DMF (3.5 mL). The dipeptide was isolated after precipitation in CH₂Cl₂/pentane (946 mg, 74%). mp 168-170° C. $^1$H NMR (300 MHz, DMSO-d₆) δ 1.2-1.35 (m, 4H, 2 CH₂ Lys), 1.29 (s, 9H, (CH₃)₃), 1.35 (s, 9H, (CH₃)₃), 1.6 (m, 2H, CH₂ Lys), 2.55-3.05 (m, 4H, CH₂ Tyr, CH₂ Lys), 3.63 (m, 1H, CHα), 3.94 (m, 1H, CHα), 5.05 (s, 2H, CH₂ (Bn)), 6.70 (m, 1H, NHBoc), 6.88 (d, J=8.2 Hz, 2 aromatic H), 7.14 (d, J=8.2 Hz, 2 aromatic H), 7.31-7.52 (m, 5 aromatic H). $^{13}$C NMR (75 MHz, DMSO-d₆) δ 22.6, 26.8 (2 CH₂ Lys), 28.6, 28.7 (2 (CH₃)₃), 30 (CH₂ Lys), 32.6 (CH₂NHBoc), 36.8 (CH₂ Tyr), 54.4, 56.9 (CHα Tyr, Lys), 69.5 (CH₂ (Bn)), 77.8, 78.6 (2 C(CH₃)₃), 114.7, 128, 128.2, 128.8, 130.6, 131.1, 137.6 (11 aromatic C), 155.7, 156, 157.2 (Car-O, 2 CO carbamate), 170.7, 174.7 (CO amide, CO acid).

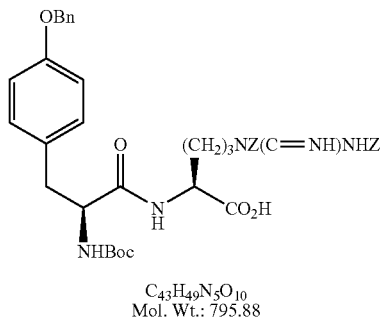

C₄₃H₄₉N₅O₁₀
Mol. Wt.: 795.88

N-Boc-Tyr(Bn)-Arg(Z)₂—OH: Same procedure as above with N-Boc-Tyr(Bn)-Osu (837 mg, 1.78 mmol), H-Arg(Z)₂—OH (791 mg, 1.78 mmol) in DMF (10 mL). The reaction mixture was stirred for 4 days followed by usual work-up. The dipeptide was isolated after precipitation in CH₂Cl₂/pentane (972 mg, 68%). $^1$H NMR (300 MHz, CDCl₃) δ 1.37 (s, 9H, (CH₃)₃), 1.6 (m, 2H, CH₂ Arg), 1.79 (m, 2H, CH₂ Arg), 2.85-3 (m, 2H, CH₂ Tyr), 3.92 (m, 2H, CH₂NZ), 4.29 (m, 1H, CHα), 4.48 (m, 1H, CHα), 4.99-5.23 (m, 8H, 3 CH₂, 2 NH), 6.85 (d, J=8.4 Hz, 2 aromatic H), 7.02 (d, J=8.4 Hz, 2 aromatic H), 7.1 (m, 1 NH), 7.38 (m, 15 aromatic H), 9.43 (m, 1 NH). $^{13}$C NMR (50 MHz, CDCl₃) δ 25.1, 25.8 (2 CH₂ Arg), 28.6 ((CH₃)₃), 37.7 (CH₂ Tyr), 44.5 (CH₂NHZ), 53, 56 (CHα Tyr, Arg), 67.5, 69.4, 70.3 (2 CH₂ (Z), CH₂ (Bn)), 80.6 (C(CH₃)₃), 115.3, 127.8, 128.4, 128.7, 128.9, 129.2, 130.7, 135, 137, 137.4 (23 aromatic C), 156, 156.1, 158.1, 161, 163.9 (Car-O, 3 CO carbamate, CO imine), 172.4, 174.8 (CO amide, CO acid).

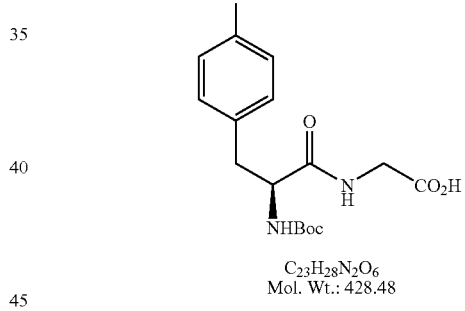

C₂₃H₂₈N₂O₆
Mol. Wt.: 428.48

N-Boc-Tyr(Bn)-Gly-OH: A solution of N-Boc-Tyr(Bn)-Gly-OMe (500 mg, 1.13 mmol) in THF (1.4 mL) was treated with aqueous LiOH (1 M, 1.4 mL, 1.4 mmol) at 0° C. for 1 h 30. The reaction mixture was quenched with aqueous 4 N HCl. The aqueous phase was extracted with CH₂Cl₂. The combined organic phases were dried over Na₂SO₄ and concentrated in vacuo to give crude carboxylic acid (435 mg, 89%) which was taken in the next step without further purification. mp 157-159° C. $^1$H NMR (300 MHz, DMSO-d₆) δ 1.29 (s, 9H, (CH₃)₃), 2.65 (dd, J=13.7 Hz, J=10.5 Hz, 1H, CH₂ Tyr), 2.93 (dd, J=13.7 Hz, J=3.5 Hz, 1H, CH₂ Tyr), 3.77 (m, 2H, CH₂ Gly), 4.13 (m, 1H, CHα Tyr), 5.05 (m, 2H, CH₂ (Bn)), 6.86 (d, J=8.9 Hz, 1H, NHBoc), 6.93 (d, J=8.5 Hz, 2 aromatic H), 7.18 (d, J=8.5 Hz, 2 aromatic H), 7.25-7.45 (m, 5 aromatic H), 8.19 (m, 1H, NH amide). $^{13}$C NMR (75 MHz, DMSO-d₆) δ 26.2 ((CH₃)₃), 34.7 (CH₂ Tyr), 38.8 (CH₂ Gly), 53.9 (CHα Tyr), 67.2 (CH₂ (Bn)), 76 (C(CH₃)₃), 112.4, 125.7, 125.8, 126.5, 128.3, 128.5, 135.4 (11 aromatic C), 153.3, 154.9 (Car-O, CO carbamate), 169.3, 170.2 (CO acid, CO amide).

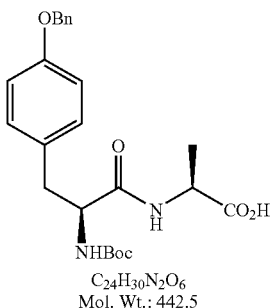

C₂₄H₃₀N₂O₆
Mol. Wt.: 442.5

N-Boc-Tyr(Bn)-Ala-OH: Same procedure as above with N-Boc-Tyr(Bn)-Ala-OMe (1.55 g, 3.39 mmol), aqueous LiOH (1 M, 4 mL, 4 mmol) in THF (4 mL). A white solid was obtained (1.25 g, 83%) which was used in the next step without further purification. $^1$H NMR (200 MHz, CDCl₃) δ 1.41 (s large, 12H, CH₃, (CH₃)₃), 3.01 (m, 2H, CH₂), 4.38 (m, 1H, CHα), 4.53 (m, 1H, CHα), 5.04 (s, 2H, CH₂ (Bn)), 5.16 (broad s, 1H, NHBoc), 6.68 (m, 1H, NH amide), 6.91 (d, J=8.6 Hz, 2 aromatic H), 7.12 (d, J=8.6 Hz, 2 aromatic H), 7.33-7.44 (m, 5 aromatic H). $^{13}$C NMR (75 MHz, CDCl₃) δ 18 (CH₃), 28.2 ((CH₃)₃), 37.5 (CH₂ Tyr), 48.2 (CHα Ala), 55.6 (CHα Tyr), 70 (CH₂ (Bn)), 80.5 (C(CH₃)₃), 115, 127.4, 128, 128.5, 128.6, 130.4, 137 (11 aromatic C), 155.8, 157.8 (Car-O, CO carbamate), 171.6, 175.5 (CO acid, CO amide).

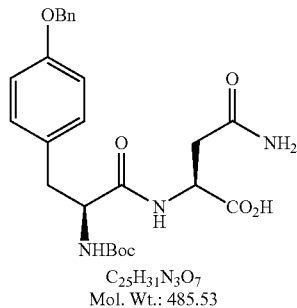

C₂₅H₃₁N₃O₇
Mol. Wt.: 485.53

N-Boc-Tyr(Bn)-Asn-OH: Same procedure as above with N-Boc-Tyr(Bn)-Asn-OMe (1.035 g, 2.072 mmol), aqueous LiOH (1 M, 2.2 mL, 2.2 mmol) in THF (15 mL). A beige solid was obtained (1.03 g, 100%) which was used in the next step without further purification. $^1$H NMR (300 MHz, CD₃OD) δ 1.35 (s, 9H, (CH₃)₃), 2.73-3.13 (m, 4H, CH₂), 4.29 (m, 1H, CHα), 4.72 (m, 1H, CHα), 5.06 (s, 2H, CH₂ (Bn)), 6.92 (d, J=5 Hz, 2 aromatic H), 7.17 (d, J=5 Hz, 2 aromatic H), 7.33-7.44 (m, 5 aromatic H). $^{13}$C NMR (75 MHz, CD₃OD) δ 28.7 ((CH₃)₃), 37.7, 38.3 (CH₂ Tyr and Asn), 50.4 (CHα Asn), 57.5 (CHα Tyr), 71 (CH₂ (Bn)), 80.7 (C(CH₃)₃), 116.0, 128.5, 128.8, 129.5, 130.9, 131.5, 131.8, 138.8 (11 aromatic C), 157.6, 159.2 (Car-O, CO carbamate), 174.2, 174.4, 175.0 (CO acid, CO amide).

II) Preparation of Halogenated Tripeptides

Compounds IV-1a

Bromo, iodo tripeptides were prepared according to Berthelot, A.; Piguel, S.; Le Dour, G.; Vidal, J., Synthesis of macrocyclic peptide analogues of proteasome inhibitor TMC-95A. J. Org. Chem. 2003, 68, (25), 9835-9838.

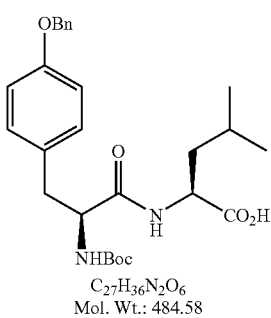

C₂₇H₃₆N₂O₆
Mol. Wt.: 484.58

N-Boc-Tyr(Bn)-Leu-OH: Same procedure as above with N-Boc-Tyr(Bn)-Leu-OMe (1.034 g, 2.073 mmol), aqueous LiOH (1 M, 2.2 mL, 2.2 mmol) in THF (15 mL). A white solid was obtained (1.035 g, 100%) which was used in the next step without further purification. $^1$H NMR (300 MHz, CDCl₃) δ 0.90 (d, J=5 Hz, 1H, Me₂ Leu), 1.40 (s, 9H, (CH₃)₃), 1.60 (m, 3H, CH₂—CH Leu), 3.00 (m, 2H, CH₂), 4.29 (m, 1H, CHα), 4.44 (m, 1H, CHα), 4.88 (s, 2H, CH₂ (Bn)), 5.29 (broad s, 1H, NHBoc), 6.70 (m, 1H, NH amide), 6.91 (d, J=5 Hz, 2 aromatic H), 7.12 (d, J=5 Hz, 2 aromatic H), 7.33-7.44 (m, 5 aromatic H). $^3$C NMR (75 MHz, CDCl₃) δ 21.8, 22.9, 24.7 (CH-Me₂ Leu), 28.2 ((CH₃)₃), 37.0 CH₂ Leu), 41.1 (CH₂ Tyr), 51.6 (CHα Leu), 55.7 (CHα Tyr), 70 (CH₂ (Bn)), 80.4 (C(CH₃)₃), 114.9, 127.5, 127.9, 128.5, 128.9, 130.5, 137.0 (11 aromatic C), 155.8, 157.8 (Car-O, CO carbamate), 172.0, 176.8 (CO acid, CO amide).

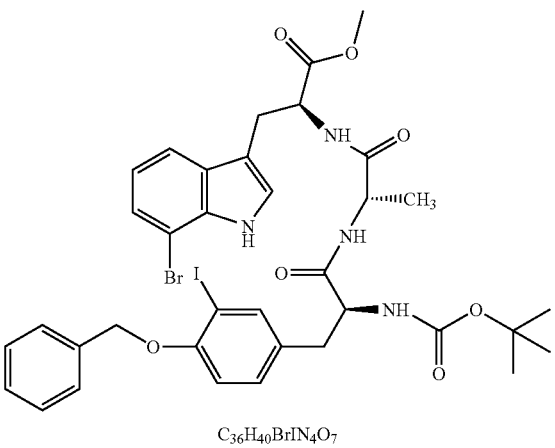

C₃₆H₄₀BrIN₄O₇
Mol. Wt.: 847.53

N-Boc-3-iodo-Tyr(Bn)-Ala-7-bromo-Trp-OMe: compound A248 described in the above article.

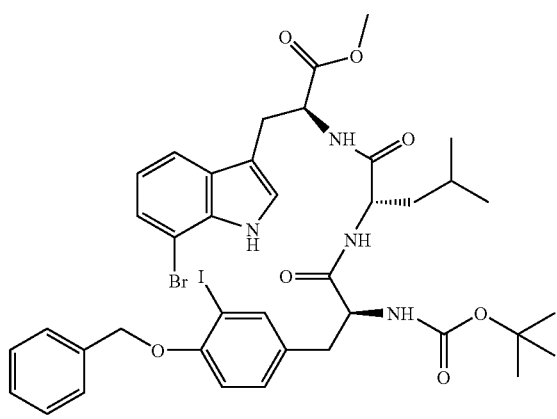

C₃₉H₄₆BrIN₄O₇
Mol. Wt.: 889.61

N-Boc-3-iodo-Tyr(Bn)-Leu-7-bromo-Trp-OMe: compound A268 described in the above article.

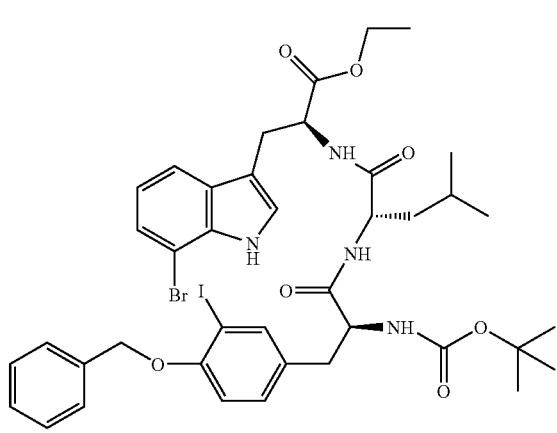

C₄₀H₄₈BrIN₄O₇
Mol. Wt.: 903.64

N-Boc-3-iodo-Tyr(Bn)-Leu-7-bromo-Trp-OEt: compound A174. The peptide coupling was performed in CH₂Cl₂ (0.5 mL) using 7-bromo-Trp-OEt (15 mg, 0.048 mmol), crude N-Boc-3-iodo-Tyr(Bn)-Leu-OH (31 mg, 0.05 mmol), EDC (11 mg, 0.053 mmol), HOBt (8 mg, 0.053 mmol) and NEt₃ (15 µL, 0.1 mmol). The residue was purified by preparative TLC on silica gel (2% MeOH/CH₂Cl₂) and subjected to crystallization with Et₂O/pentane to afford tripeptide N-Boc-3-iodo-Tyr(Bn)-Leu-7-bromo-Trp-OEt (29 mg, 67%) as a white amorphous solid. ¹H NMR (300 MHz, CDCl₃, COSY) δ 0.81 (d, J=6.2 Hz, 3H, CH₃ Leu), 0.87 (d, J=6.2 Hz, 3H, CH₃ Leu), 1.2 (t, J=7.1 Hz, 3H, CH₃ (Et)), 1.41 (s, 9H, (CH₃)₃), 1.52-1.61 (m, 3H, CH, CH₂ Leu), 2.91 (m, 2H, CH₂ Tyr), 3.26 (m, 2H, CH₂ Trp), 4.09 (m, 2H, OCH₂ (Et)), 4.28 (m, 1H, CHα Tyr), 4.47 (m, 1H, CHα Leu), 4.85 (m, 1H, CHα Trp), 4.90 (d, 1H, J=7.9 Hz, NHBoc), 5.04 (s, 2H, CH₂ Bn), 6.51 (m, 1H, NH), 6.71 (d, J=8.4, 1H, H5 Tyr), 6.75 (d, J=8.1 Hz, 1H, NH), 6.95 (t, J=7.7 Hz, 1H, H5 Trp), 7.04 (m, 2H, aromatic H), 7.25-7.46 (m, 7H, aromatic H), 7.59 (d, J=2 Hz, 1H, H2 Tyr), 8.57 (broad s, 1H, NH ind). ¹³C NMR (75 MHz, CDCl₃) 14.1 (CH₃ Et), 22.2 (CH₃ Leu), 22.9 (CH₃ Leu), 24.7 (CH Leu), 27.7 (CH₂ Trp), 28.3 ((CH₃)₃), 36.1 (CH₂ Tyr), 40.9 (CH₂ Leu), 51.7 (CHα Leu), 52.8 (CHα Trp), 55.8 (CHα Tyr), 61.7 (CH₂ Et), 70.9 (CH₂Bn), 80.8 (C(CH₃)₃), 87 (C3 Tyr), 104.9 (C7 Trp), 111 (C), 112.7 (CH), 117.9 (CH), 120.7 (CH), 124.1 (CH), 124.5 (CH), 127 (CH), 128 (CH), 128.6 (CH), 128.8 (C), 130.3 (CH), 130.9 (C), 134.8 (C), 136.5 (C), 140.2 (CH), 155.8 (C4 Tyr), 156.4 (CO Boc), 177.1, 171.2, 171.5 (2 CO amide, CO ester). Anal. Calcd. for C₄₀H₄₈N₄O₇BrI: C, 53.17; H, 5.36; N, 6.20. Found: C, 53.06; H, 5.34; N, 6.10.

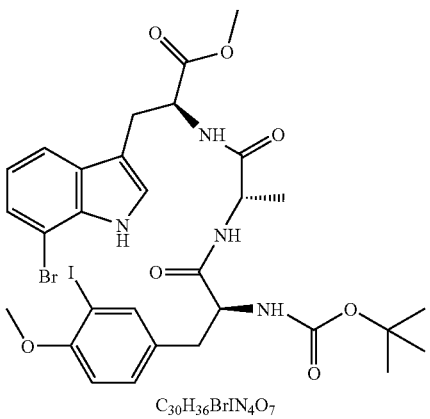

C₃₀H₃₆BrIN₄O₇
Mol. Wt.: 771.44

N-Boc-3-iodo-Tyr(Me)-Ala-7-bromo-Trp-OMe: compound A385: The peptide coupling was performed in CH₂Cl₂ (1.5 mL) using 7-bromo-Trp-OMe (100 mg, 0.3 mmol), crude N-Boc-3-iodo-Tyr(Me)-Ala-OH (148 mg, 0.3 mmol), EDC (63 mg, 0.33 mmol), HOBt (45 mg, 0.33 mmol) and NEt₃ (93 µL, 0.66 mmol). The residue was subjected to flash chromatography on silica gel (2% MeOH/CH₂Cl₂) to afford tripeptide N-Boc-3-iodo-Tyr(Me)-Ala-7-bromo-Trp-OMe (204 mg, 88%) as a white amorphous solid. Rf 0.3. ¹H NMR (300 MHz, CDCl₃) δ 1.31 (d, J=7 Hz, 3H, CH₃), 1.4 (s, 9H, (CH₃)₃), 2.83 (m, CH₂ Tyr), 3.3 (m, 2H, CH₂ Trp), 3.68 (s, 3H, OCH₃), 3.8 (s, 3H, OCH₃), 4.35 (m, 1H, CH Tyr), 4.62 (q, J=7.2 Hz, 1H, CH Ala), 4.92 (m, 1H, CH Trp), 5.22 (broad d, J=7.6 Hz, 1H, NHBoc), 6.67 (d, J=8.4 Hz, 1H, H5 Tyr), 6.96 (t, J=7.7 Hz, 1H, H5 Trp), 7.03-7.08 (m, 2 aromatic H), 7.27 (d, J=7.7 Hz, 1 aromatic H Trp), 7.46 (d, J≈7.7 Hz, 1 aromatic H Trp), 7.52 (d, J=1.3 Hz, 1H, H2 Tyr), 8.83 (s, 1H, NHind). ¹³C NMR (75 MHz, CDCl₃) δ 18.5 (CH₃ Ala), 26.4 (CH₂ Trp), 28.3 ((CH₃)₃), 35.4 (CH₂ Tyr), 48.9 (CH Ala), 52.5 (OCH₃), 52.9 (CH Trp), 55.5 (CH Tyr), 56.3 (OCH₃), 80.6 (C(CH₃)₃), 86 (C3 Tyr), 104.9 (C7 Trp), 110.8 (C3 Trp), 110.9 (CH), 117.7 (CH), 120.7 (CH), 124.2 (CH), 124.4 (CH), 128.7 (C), 130.3 (CH), 130.6 (CH), 134.8 (C), 140.1 (CH(2) Tyr), 155.6 (C4 Tyr), 157.1 (CO Boc), 171.3, 171.8, 171.9 (2 CO amide, CO ester). HRMS (ESI) calcd for C₃₀H₃₆N₄O₇⁷⁹BrINa [M+Na]⁺ 793.0710. Found 793.0709.

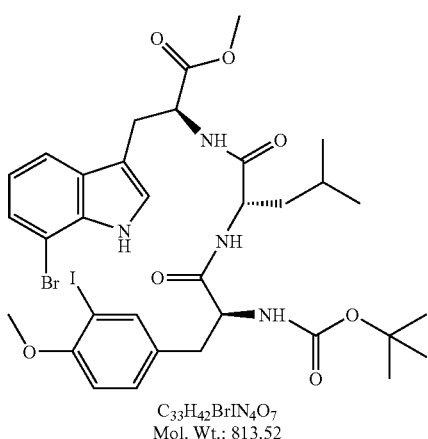

C₃₃H₄₂BrIN₄O₇
Mol. Wt.: 813.52

N-Boc-3-iodo-Tyr(Me)-Leu-7-bromo-Trp-OMe: compound A363 described in the above article.

Ome (85.5 mg, 0.100 mmol) in THF (0.4 mL) was treated at 0° C. by 1 M aqueous NaOH (0.12 mL, 0.12 mmol). After 5 hours at room temperature, 1 M aqueous HCl was added (0.36 mL, 0.36 mmol). The resulting mixture was diluted by water and extracted by CH$_2$Cl$_2$ (3×10 mL). After drying of the organic phase over Na$_2$SO$_4$ and evaporation of the solvent, the residue was subjected to flash chromatography on silica gel (2% MeOH/CH$_2$Cl$_2$) to afford remaining N-Boc-3-iodo-Tyr(Me)-Ala-7-bromo-Trp-OCH$_3$ (10.13 mg, 12%) and N-Boc-3-iodo-Tyr(Me)-Ala-7-bromo-Trp-OH (58.3 mg, 70%, corrected yield 82%) as a white amorphous solid. $^1$H NMR (200 MHz, CDCl$_3$) δ 0.9 (d, J=6.4 Hz, 3H, CH$_3$), 1.42 (s, 9H, (CH$_3$)$_3$), 2.87 (m, CH$_2$ Tyr), 3.32 (m, 2H, CH$_2$ Trp), 4.40 (m, 1H, CH Tyr), 4.52 (m, 1H CH Ala), 4.85 (m, 1H, CH Trp), 5.06 (s, 2H, CH$_2$O), 5.16 (broad d, J=7.6 Hz, 1H, NHBoc), 6.71 (d, J=8 Hz, 1H, H5 Tyr), 6.91-7.58 (m, 14H, aromatic H and NH), 8.68 (s, 1H, NHind). HRMS (ESI) calcd for C$_{35}$H$_{38}$$^{79}$BrIN$_4$O$_7$Na [(M+Na)$^+$] 855.0866. Found 855.0896.

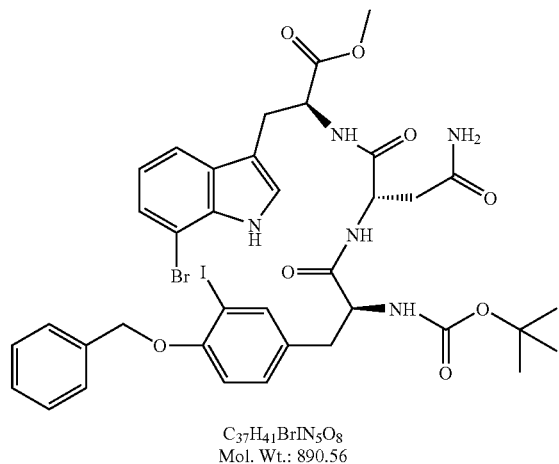

C₃₇H₄₁BrIN₅O₈
Mol. Wt.: 890.56

N-Boc-3-iodo-Tyr(Bn)-Asn-7-bromo-Trp-OMe: compound SP274 described in the above article

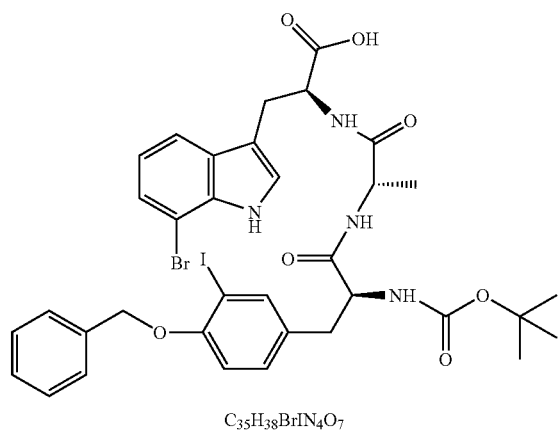

C₃₅H₃₈BrIN₄O₇
Mol. Wt.: 833.51

N-Boc-3-iodo-Tyr(Bn)-Ala-7-bromo-Trp-OH: compound A215. A solution of N-3-iodo-Tyr(Bn)-Ala-7-bromo-Trp-

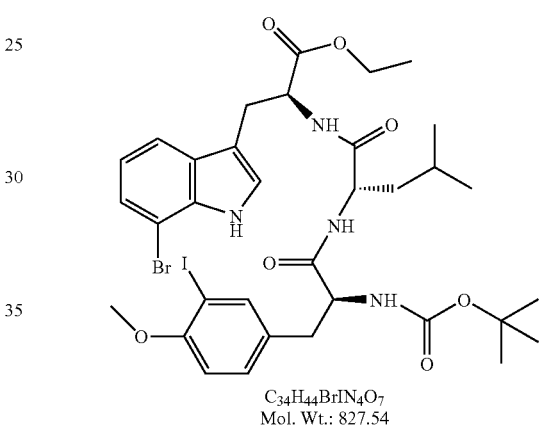

C₃₄H₄₄BrIN₄O₇
Mol. Wt.: 827.54

N-Boc-3-iodo-Tyr(Me)-Leu-7-bromo-Trp-OEt: compound A340. The peptide coupling was performed in CH$_2$Cl$_2$ (3.7 mL) using 7-bromo-Trp-OEt (294 mg, 0.75 mmol), crude N-Boc-3-iodo-Tyr(Me)-Leu-OH (400 mg, 0.75 mmol), EDC (172 mg, 0.9 mmol), HOBt (121 mg, 0.9 mmol) and NEt$_3$ (230 μL, 1.65 mmol). The residue was subjected to flash chromatography on silica gel (5% MeOH/CH$_2$Cl$_2$) to afford tripeptide N-Boc-3-iodo-Tyr(Me)-Leu-7-bromo-Trp-OEt (334 mg, 54%) as a white amorphous solid. Rf 0.6 (5% MeOH/CH$_2$Cl$_2$), $^1$H NMR (300 MHz, CDCl$_3$) δ 0.89 (d, J=6.0 Hz, 3H, CH$_3$ Leu), 0.90 (d, J=6.0 Hz, 3H, CH$_3$ Leu), 1.24 (t, J=7.1 Hz, 3H, CH$_3$ (Et)), 1.44 (s, 9H, (CH$_3$)$_3$), 1.61 (m, 3H, CH, CH$_2$ Leu), 2.96 (m, 2H, CH$_2$ Tyr), 3.31 (m, 2H, CH$_2$ Trp), 3.86 (s, 3H, OCH$_3$), 4.14 (m, 2H, CH$_2$ (Et)), 4.30 (m, 1H, CHα Tyr), 4.41 (m, 1H, CHα Leu), 4.85 (m, 2H, CHα Trp and NHBoc), 6.40 (m, 1H, NH), 6.60 (m, 1H), 6.73 (d, J=8.4 Hz, 1H), 7.00 (t, J=7.7 Hz, 1H, H5 Trp), 7.11 (m, 2H, aromatic H), 7.34 (d, J=7.7 Hz, 1H), 7.49 (d, J=7.7 Hz, 1H), 7.61 (d, J=1.9 Hz, 1H), 8.62 (broad s, 1H, NH ind). $^{13}$C NMR (75 MHz, CDCl$_3$) δ 14.1 (CH$_3$ Et), 22.2 (CH$_3$ Leu), 22.9 (CH$_3$ Leu), 25.6 (CH Leu), 27.7 (CH$_2$ Trp), 28.3 ((CH$_3$)$_3$), 36.4 (CH$_2$ Tyr), 41.4 (CH$_2$ Leu), 51.7 (CHα Leu), 52.8 (CHα Trp), 55.5 (CHα Tyr), 56.3 (OCH$_3$), 61.7 (OCH$_2$ Et), 80.4 (C(CH$_3$)$_3$), 86.0 (C), 104.9 (C7 Trp), 110.8 (CH), 110.9 (C), 117.8 (CH), 120.5 (CH), 124.3 (CH), 128.7 (C), 130.3 (CH), 130.8 (C), 134.7 (C), 140.1 (CH), 155.6 (C4 Tyr), 157.0 (CO Boc), 171.5, 171.6, 171.9 (2 CO amide, CO ester). Anal. Calcd. for $C_{35}H_{44}N_4O_7BrI$: C, 49.77; H, 5.47; N, 6.41. Found: C, 49.35; H, 5.36; N, 6.77.

IV) Preparation of Biaryl Compounds

Compounds III

General procedure for the preparation of biaryls as illustrated by the synthesis of:

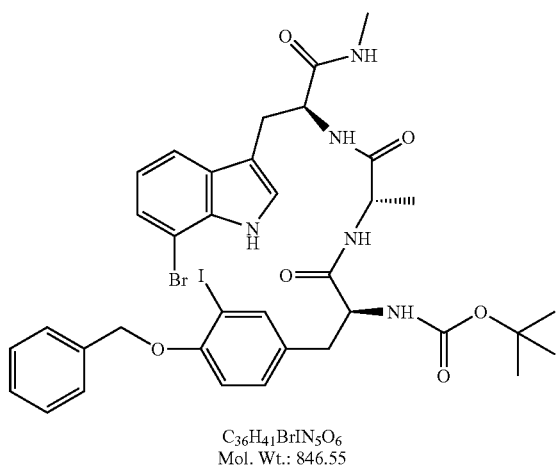

$C_{36}H_{41}BrIN_5O_6$
Mol. Wt.: 846.55

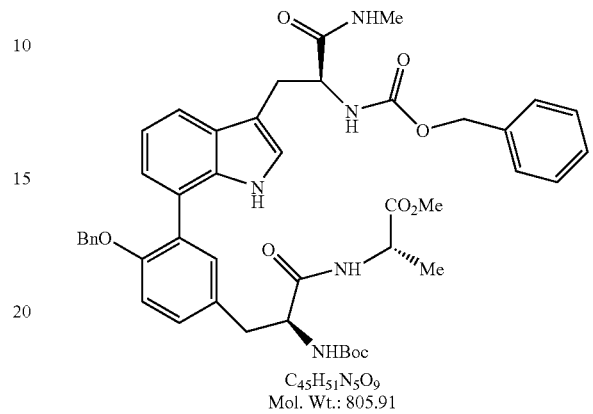

$C_{45}H_{51}N_5O_9$
Mol. Wt.: 805.91

N-Boc-3-iodo-Tyr(Bn)-Ala-7-bromo-Trp-NHMe: compound A254. The peptide coupling was performed in $CH_2Cl_2$ (4.4 mL) using HBr, 7-bromo-Trp-NHMe (330 mg, 0.874 mmol), crude N-Boc-3-iodo-Tyr(Bn)-Ala-OH (521 mg, 0.918 mmol), EDC (124 mg, 0.96 mmol), HOBt (130 mg, 0.96 mmol) and $NEt_3$ (370 µL, 2.62 mmol). The residue was subjected to flash chromatography on silica gel (5% MeOH/$CH_2Cl_2$) to afford tripeptide N-Boc-3-iodo-Tyr(Bn)-Ala-7-bromo-Trp-NHMe (322 mg, 43%) as a white amorphous solid. $^1$H NMR (300 MHz, DMSO-$d_6$) δ 1.18 (d, J=7 Hz, 3H), 1.29 (s, 9H), 2.57 (d, J=4 Hz, 3H), 2.81 (m, 2H), 3.11 (m, 2H), 4.07 (m, 1H), 4.28 (m, 1H), 4.43 (m, 1H), 5.14 (s, 2H), 6.96 (m, 2H), 7.17-8.21 (m, 15H), 11.04 (s, 1H). $^{13}$C NMR (75 MHz, DMSO-$d_6$) δ 25.6 ($CH_3$ Ala), 27.7 ($CH_2$ Trp), 28.0 ($CH_3$ Boc and $CH_3$N), 35.7 ($CH_2$ Tyr), 47.9 (CHα Ala), 53.2 (CHα Trp), 55.6 (CHα Tyr), 69.9 ($CH_2$ Bn), 78.0 (C Boc), 86.3 (CI), 104.0 (CBr), 111.6 (Cγ Trp), 112.5, 117.9, 119.6, 123.3, 124.9, 127.0, 127.6, 128.3, 128.9 (C), 130.4, 132.6 (C), 134.2 (C), 136.7 (C), 139.3 (C), 139.4, 155.1 (CO Boc), 171.2 (CONH), 171.4 (CONH), 171.6 (CONH). HRMS (ESI) calcd for $C_{36}H_{41}BrIN_5O_6Na$ [(M+Na)$^+$] 868.1183. Found 869.1175.

III) Preparation of Macrocyclic Peptides

Compounds II

Macrocyclic peptides were prepared according to Berthelot, A.; Piguel, S.; Le Dour, G.; Vidal, J., Synthesis of macrocyclic peptide analogues of proteasome inhibitor TMC-95A. J. Org. Chem. 2003, 68, (25), 9835-9838.

A374F1: described in the above article

A291 described in the above article

A389F1p12 described in the above article

Biaryl SP225F2:
N-(tert-butoxycarbonyl)-3-[(4,4,5,5-tetramethyl-1,3,2-dioxaborolane-2-yl)]-Tyr(Bn)-Ala-OMe: A flame-dried Schlenk tube charged with Boc-4iodoTyr(Bn)-Ala-OMe (1.47 g, 2.53 mmol), KOAc (946 mg, 9.64 mmol), bis(pinacolato)diboron (773 mg, 3.04 mmol) and Pd(dppf)$Cl_2.CH_2Cl_2$ (166 mg, 8 mol %) was flushed with argon. Degassed DMSO (17 mL) was added and the reaction mixture was stirred at 80° C. for 16 h. The mixture was diluted with cold water, extracted with $CH_2Cl_2$ and the combined organic extracts were washed with brine, dried over $Na_2SO_4$ and the solvent was concentrated in vacuo. The brown oil was purified by flash chromatography on silica gel (20-40% AcOEt/Heptane) to give an inseparable mixture of the aryl boronate N-(tert-butoxycarbonyl)-3-[(4,4,5,5-tetramethyl-1, 3,2-dioxaborolane-2-yl)]-Tyr(Bn)-Ala-OMe (57.5% yield estimated by $^1$H NMN) and the dipeptide Boc-Tyr(Bn)-Ala-OMe (939 mg, ca 7.8:1 ratio). Aryl boronate: $^1$H NMR (300 MHz, CDCl$_3$) δ 1.37 (d, J=7.5 Hz, 3H, $CH_3$ Ala), 1.38 (s, 12H, 4 $CH_3$ boronic ester), 1.44 (s, 9H, $(CH_3)_3$), 2.99 (dd, J=14 Hz, J=6.7 Hz, 1H, $CH_2$ Tyr), 3.1 (dd, J=14 Hz, J=6.2 Hz, 1H, $CH_2$ Tyr), 3.72 (s, 3H, $OCH_3$), 4.33 (m, 1H, CHα Tyr), 4.53 (m, 1H, CHα Ala), 4.97 (broad s, 1H, NHBoc), 5.11 (s, 2H, $CH_2$ (Bn)), 6.44 (m, 1H, NH amide), 6.89 (d, J=8.5 Hz, 1H, H-2), 7.26 (dd, J=8.7 Hz, J=2.2 Hz, 1H, H-3), 7.28-7.46 (m, 3 aromatic H), 7.53 (d, J=2.2 Hz, 1H, H5), 7.62 (m, 2 aromatic H). $^3$C NMR (50 MHz, CDCl$_3$) δ 18.4 ($CH_3$ Ala), 24.9 (4 $CH_3$ boronic ester), 28.3 (($CH_3$)$_3$), 37.3 ($CH_2$ Tyr), 48.2 (CHα Ala), 52.4 ($OCH_3$), 55.7 (CHα Tyr), 70 ($CH_2$ (Bn)), 80.2 (C (Boc)), 83.5 (2 C($CH_3$)$_2$), 112.3 (CH(2)), 126.7-128.9 (8 aromatic C), 133.4 (C3), 137.5 (CH(5)), 155.3 (C(4)), 162.4 (CO (Boc)), 170.9, 172.8 (CO amide, CO ester). HRMS (LSIMS with Cs$^+$) calcd for $C_{31}H_{44}N_2O_8B$ [(M+H)$^+$] 583.3191. Found 583.3184. A flask adapted with a condenser and charged with the unseparable mixture of aryl boronate and dipeptide Boc-Tyr(Bn)-Ala-OMe (909 mg, 1.42 mmol based on the ratio 7.8:1 in favor of the aryl boronate), Z-7-bromoTrp-NHMe (488 mg, 1.13 mmol), P(o-tolyl)$_3$ (86.4 mg, 20 mol %) and Pd(OAc)$_2$ (32.2 mg, 10 mol %) was flushed with argon. Degassed dioxane (11 mL) and 1.4 mL of an aqueous solution of $Na_2CO_3$ (2.8 mmol, 2 M) were added. The resulting mixture was stirred at 85° C. for 3-4 h. The reaction mixture was passed through a pad of celite and the solvent was concentrated in vacuo. The greenish residue was purified by flash chromatography on silica gel (60-80% AcOEt/Heptane) and the biaryl compound was isolated as an amorphous pale yellow solid (547.5 mg, 60%). Only one atropoisomer was obtained. $R_f$ 0.3 (80% AcOEt/Heptane). $^1$H NMR (500 MHz, CDCl$_3$) δ 1.37 (s, 9H, (CH$_3$)$_3$), 1.38 (d, J=7.5 Hz, 3H, CH$_3$ Ala), 2.6 (d, J=4.7 Hz, 3H, NHMe), 2.93 (dd, J=13.9 Hz, J=7.2 Hz, 1H, CH$_2$ Tyr), 3.15 (m, 2H, CH$_2$ Tyr, CH$_2$ Trp), 3.4 (dd, J=13.9 Hz, J=4.2 Hz, 1H, CH$_2$ Trp), 3.55 (s, 3H, OCH$_3$), 4.35 (m, 3H, CHα Tyr, CHα Ala, CHα Trp), 4.99 (m, 2H, CH$_2$ (Z)), 5.12 (s, 2H, CH$_2$ (Bn)), 5.18 (broad s, 1H, NHBoc), 5.65 (broad s, 1H, NHZ), 5.74 (broad s, 1H, NHMe), 6.65 (m, 1H, NH amide), 7.01-7.35 (m, 16 aromatic H), 7.65 (broad s, 1 aromatic H), 9.01 (broad s, 1H, NH indole). $^{13}$C NMR (75 MHz, CDCl$_3$) δ 18.1 (CH$_3$ Ala), 26.1 (NHCH$_3$), 28.2 ((CH$_3$)$_3$), 28.8 (CH$_2$ Trp), 38.3 (CH$_2$ Tyr), 48 (CHα Ala), 52.4 (OCH$_3$), 55.1, 55.8 (CHα Tyr, CHα Trp), 67, 70.8 (CH$_2$ (Bn), CH$_2$ (Z)), 80.2 ((CH$_3$)$_3$C), 109-137 (25 aromatic C), 154.8, 155.5, 156 (C—OBn, 2 CO carbamate), 171.2, 172.1, 173.1 (2 CO amide, CO ester). HRMS (LSIMS with Cs$^+$) calcd for C$_{45}$H$_{51}$N$_5$O$_9$ [M$^+$] 805.3687. Found 805.3688.

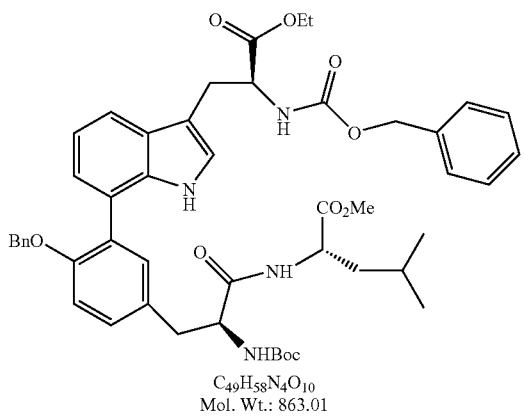

C$_{49}$H$_{58}$N$_4$O$_{10}$
Mol. Wt.: 863.01

Biaryl SP221:

N-(tert-butoxycarbonyl)-3-[(4,4,5,5-tetramethyl-1,3,2-dioxaborolane-2-yl)]-Tyr(Bn)-Leu-OMe: Same procedure as described above with Boc-4-iodo-Tyr(Bn)-Leu-OMe (2 g, 3.2 mmol), KOAc (1.09 g, 11.1 mmol), bis(pinacolato)diboron (986 mg, 3.88 mmol) and Pd(dppf)Cl$_2$.CH$_2$Cl$_2$ (212 mg, 8 mol %) in DMSO (20 mL). The reaction mixture was stirred at 80° C. for 18 h followed by work-up. After purification by flash chromatography on silica gel (20-40% AcOEt/Heptane), an inseparable mixture of the aryl boronate (62% yield estimated by $^1$H RMN) and the dipeptide Boc-Tyr(Bn)-Leu-OMe was isolated as a white foam (ca 4.2:1 ratio). Aryl boronate: $^1$H NMR (300 MHz, CDCl$_3$) δ 0.9 (d, J=5.6 Hz, 3H, CH$_3$ Leu), 0.92 (d, J=5.6 Hz, 3H, CH$_3$ Leu), 1.38 (s, 12H, 4 CH$_3$ boronic ester), 1.43 (s, 9H, (CH$_3$)$_3$), 1.44-1.6 (m, 3H, CH$_2$, CH Leu), 3.02 (m, 2H, CH$_2$ Tyr), 3.7 (s, 3H, OCH$_3$), 4.3 (m, 1H, CHα Tyr), 4.56 (m, 1H, CHα Leu), 4.9 (broad s, 1H, NHBoc), 5.11 (s, 2H, CH$_2$ (Bn)), 6.29 (m, 1H, NH amide), 6.88 (d, J=8.5 Hz, 1H, H-2), 7.27-7.42 (m, 4 aromatic H), 7.54 (d, J=2.3 Hz, 1H, H-5), 7.62 (m, 2 aromatic H). $^{13}$C NMR (50 MHz, CDCl$_3$) δ 21.9, 22.7 (CH$_3$ Leu), 24.6 (CH Leu), 24.9 (4 CH$_3$ boronic ester), 28.2 ((CH$_3$)$_3$), 37 (CH$_2$ Tyr), 41.5 (CH$_2$ Leu), 50.7 (CHα Leu), 52.2 (OCH$_3$), 55.8 (CHα Tyr), 70 (CH$_2$ (Bn)), 80.1 ((CH$_3$)$_3$C), 83.5 (2 C(CH$_3$)$_2$), 112.3 (C-2), 126.7-136.9 (8 aromatic C), 133.3 (C-3), 137.5 (C-5), 155.4 (C—OBn), 162.4 (CO carbamate), 171.1, 172.7 (CO amide, CO ester). HRMS (ESI) calcd for C$_{34}$H$_{49}$N$_2$O$_8$BNa [(M+Na)$^+$] 647.3480. Found 647.3489.

Same procedure as described above with a mixture of N-(tert-butoxycarbonyl)-3-[(4,4,5,5-tetramethyl-1,3,2-dioxaborolane-2-yl)]-Tyr(Bn)-Leu-OMe and dipeptide Boc-Tyr(Bn)-Leu-OMe (100 mg, 0.135 mmol), Z-7-bromoTrp-OEt (48.1 mg, 0.11 mmol), P(o-tolyl)$_3$ (8.3 mg, 20 mol %), Pd(OAc)$_2$ (3 mg, 10 mol %) and 140 μL of an aqueous solution of Na$_2$CO$_3$ (0.28 mmol, 2 M) in degassed dioxane (1.1 mL). The reaction was stirred at 85° C. for 2 h. After purification by flash chromatography on silica gel (20-30% AcOEt/Heptane), the biaryl was isolated as a pale yellow solid (87.8 mg, 94%). $^1$H NMR (300 MHz, CDCl$_3$) δ 0.9 (m, 6H, 2 CH$_3$ Leu), 1.2 (t, J=7 Hz, 3H, CH$_3$ ester), 1.36 (s, 9H, (CH$_3$)$_3$), 1.4-1.62 (m, 3H, CH$_2$CH Leu), 2.95 (dd, J=13.5 Hz, J=6.9 Hz, 1H, CH$_2$ Tyr), 3.15 (dd, J=13.8 Hz, J=6.4 Hz, 1H, CH$_2$ Tyr), 3.37 (m, 2H, CH$_2$ Trp), 3.55 (s, 3H, OCH$_3$), 4.13 (m, 2H, CH$_2$ ester), 4.49 (m, 2H, CHα Tyr), 4.6 (m, 1H, CHα Leu), 4.74 (m, 1H, CHα Trp), 4.99 (m, 2H, CH$_2$ (Z)), 5.13 (m, 3H, CH$_2$ (Bn), NHBoc), 5.4 (broad d, J=8.1 Hz, 1H, NHZ), 6.24 (broad d, J=8.2 Hz, 1H, NH amide), 6.99-7.36 (m, 16 aromatic H), 7.54 (d, J=7.8 Hz, 1 aromatic H), 9.09 (broad s, 1H, NH indole). $^{13}$C NMR (50 MHz, CDCl$_3$) δ 12.9 (CH$_3$ ester), 20.7, 21.6, 23.6 (2 CH$_3$, CH Leu), 26.9 (CH$_2$ Trp), 27.1 ((CH$_3$)$_3$), 37.1, 40.4 (CH$_2$ Tyr, CH$_2$ Leu), 49.6, 51.1, 53.5, 54 (CHα Leu, OCH$_3$, CHα Tyr, CHα Trp), 60.3 (CH$_2$ ester), 65.7, 69.8 (CH$_2$ (Bn), CH$_2$ (Z)), 79.2 ((CH$_3$)$_3$C), 108.3-135.8 (25 aromatic C), 153.7, 154.3, 154.7 (C—OBn, 2 CO carbamate), 170, 170.9, 171.9 (2 CO amide, CO ester). Anal. Calcd. for C$_{49}$H$_{58}$N$_4$O$_{10}$: C, 68.2; H, 6.77; N, 6.49. Found: C, 68.14; H, 6.82; N, 6.03.

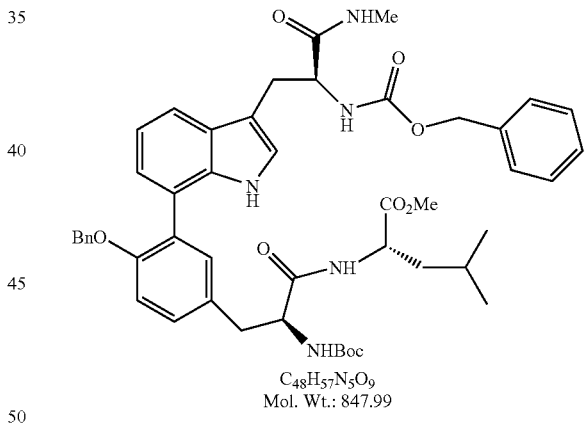

C$_{48}$H$_{57}$N$_5$O$_9$
Mol. Wt.: 847.99

Biaryl SP226F1: Same procedure as described above with a mixture of aryl boronate N-(tert-butoxycarbonyl)-3-[(4,4,5,5-tetramethyl-1,3,2-dioxaborolane-2-yl)]-Tyr(Bn)-Leu-OMe and dipeptide Boc-Tyr(Bn)-Leu-OMe (4.2:1 ratio) (361 mg, 0.463 mmol), Z-7-bromoTrp-NHMe (191 mg, 0.44 mmol), P(o-tolyl)$_3$ (15.1 mg, 10 mol %), Pd(OAc)$_2$ (6.8 mg, 5 mol %) and 0.5 mL of an aqueous solution of Na$_2$CO$_3$ (1 mmol, 2 M) in degassed dioxane (3 mL). After purification by flash chromatography on silica gel (40-60% AcOEt/Heptane), the biaryl was isolated as a pale yellow solid (269 mg, 72%). $^1$H NMR (300 MHz, CDCl$_3$) δ 0.91 (m, 6H, 2 CH$_3$ Leu), 1.38 (s, 9H, (CH$_3$)$_3$), 1.46-1.64 (m, 3H, CH$_2$CH Leu), 2.61 (d, J=4.7 Hz, 3H, NHMe), 2.96 (dd, J=14 Hz, J=6.4 Hz, 1H, CH$_2$ Tyr or Trp), 3.15 (dd, J=14 Hz, J=7.5 Hz, 2H, CH$_2$ Tyr, Trp), 3.43 (dd, J=14 Hz, J=3.6 Hz, 1H, CH$_2$ Trp or Tyr), 3.51 (s, 3H, OCH$_3$), 4.48 (m, 2H, CHα Tyr, CHα Trp), 4.6 (m, 3H, CHα Leu), 4.99 (s, 2H, CH$_2$ (Z)), 5.13 (s, 3H, CH$_2$ (Bn), NHBoc), 5.64 (m, 2H, NHZ, NHMe), 6.29 (broad d, J=8.4 Hz, 1H, NH amide), 7.01-7.35 (m, 16 aromatic H), 7.65 (m, 1 aromatic H), 9.07 (broad s, 1H, NH indole). $^{13}$C NMR (50 MHz, CDCl$_3$) δ 22.1, 23.1 (CH$_3$ Leu), 25.1 (CH Leu), 26.6 (NHCH$_3$), 28.6 ((CH$_3$)$_3$), 29.3 (CH$_2$ Trp), 38.6 (CH$_2$ Tyr), 41.7 (CH$_2$ Leu), 51.1 (CHα Leu), 52.6 (OCH$_3$), 55.9, 56.2 (CHα Tyr, CHα Trp), 67.4, 71.2 (CH$_2$ (Bn), CH$_2$ (Z)), 80.2 ((CH$_3$)$_3$C), 110.1-137.8 (25 aromatic C), 155.2, 155.9, 156.1 (C—OBn, 2 CO carbamate), 171.8, 172.5, 173.5 (2 CO amide, CO ester). HRMS (ESI) calcd for C$_{48}$H$_{57}$N$_5$O$_9$Na [(M+Na)$^+$] 870.4054. Found 870.4068.

V) Preparation of Non Halogenated Tripeptides

Compounds IV-2

General Procedure for the Preparation of Tripeptides as Illustrated by the Synthesis of

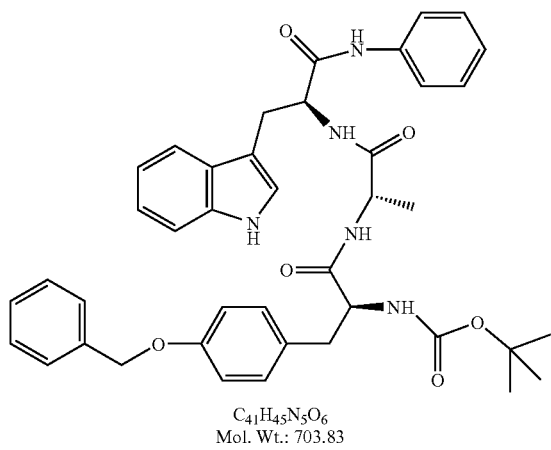

C$_{41}$H$_{45}$N$_5$O$_6$
Mol. Wt.: 703.83

N-Boc-Tyr(Bn)-Ala-Trp-NHPh: compound SP303r2. To a solution of Trp-NHPh (202 mg, 0.723 mmol) in CH$_2$Cl2/DMF (3 mL, 1/1) at 0° C. were successively added N-Boc-Tyr(Bn)-Ala-OH (320 mg, 0.723 mmol), EDC (153.6 mg, 0.8 mmol) and HOBt (108 mg, 0.8 mmol). The resulting mixture was allowed to warm up to room temperature overnight. The solvent was evaporated and the crude was triturated with water. After filtration, the solid was collected and purified by precipitation in CH$_2$Cl$_2$/MeOH to give a white amorphous solid (160.3 mg, 31%). $^1$H NMR (300 MHz, DMSO-d$_6$) δ 1.22 (d, J=7 Hz, 3H, CH$_3$), 1.28 (s, 9H, (CH$_3$)$_3$), 2.63 (m, 1H, CH$_2$), 2.89 (m, 1H, CH$_2$), 3.06 (dd, J=14.5 Hz, 7.5 Hz, 1H, CH$_2$), 3.2 (dd, J=14.5 Hz, 6.1 Hz, 1H, CH$_2$), 4.1 (m, 1H, CHα), 4.34 (m, 1H, CHα), 4.69 (m, 1H, CHα), 5.02 (s, 2H, CH$_2$ (Bn)), 6.88 (d, J=8.5 Hz, 2 aromatic H Tyr), 6.94 (m, 2 aromatic H Trp), 7.03 (t, J=7.4 Hz, 2 aromatic H Trp), 7.16 (m, 3 aromatic H), 7.25-7.42 (m, 8H), 7.58 (m, 3H), 8.02 (d, J=7.2 Hz, 1H), 8.18 (d, J=7.6 Hz, 1H), 10 (s, 1H, NH), 10.8 (s, 1H, NH). $^{13}$C NMR (75 MHz, DMSO-d$_6$) δ 18.2 (CH$_3$), 27.7 (CH$_2$ Trp), 28.1 ((CH$_3$)$_3$), 36.3 (CH$_2$ Tyr), 48.1, 54.2, 55.7 (CHα Ala, Tyr, Trp), 69 (CH$_2$ (Bn)), 78 (C(CH$_3$)$_3$), 109.5, 111.2, 114.2, 118.2, 118.4, 119.4, 120.8, 123.3, 123.5, 127.3, 127.5, 127.7, 128.3, 128.6, 130.1, 130.3, 135.9, 137.2, 138.8 (25 aromatic C), 155.2, 156.8 (Car-O, CO carbamate), 170, 171.5, 172.1 (3 CO amide). Anal. Calcd. for C$_{41}$H$_{45}$N$_5$O$_6$, 0.5H$_2$O: C, 69.08; H, 6.5; N, 9.82. Found: C, 68.82; H, 6.34; N, 9.79.

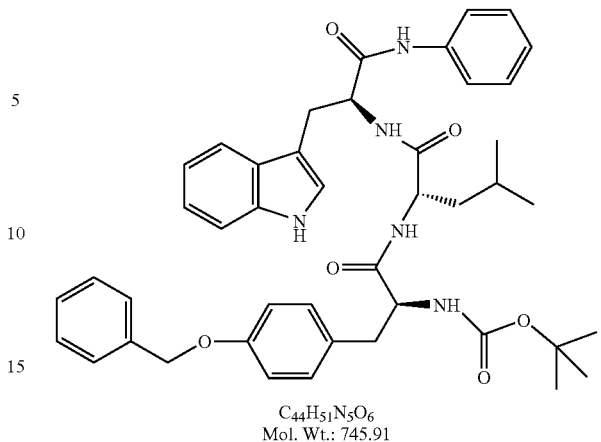

C$_{44}$H$_{51}$N$_5$O$_6$
Mol. Wt.: 745.91

N-Boc-Tyr(Bn)-Leu-Trp-NHPh: compound A424P. Same procedure as above with Trp-NHPh (67.6 mg, 0.242 mmol), N-Boc-Tyr(Bn)-Leu-OH (117 mg, 0.242 mmol), EDC (49 mg, 0.25 mmol) and HOBt (35 mg, 0.25 mmol) in CH$_2$Cl$_2$/DMF (3.6 mL, 1/1). The crude residue was dissolved in ether and precipitated with heptane to give a beige solid (135.6 mg, 75%). $^1$H NMR (300 MHz, DMSO-d$_6$) δ 0.83 (d, 3H, J=6.4 Hz, CH$_3$), 0.87 (d, 3H, J=6.4 Hz, CH$_3$), 1.22-1.44 (m, 2H, CH$_2$ Leu), 1.30 (s, 9H, (CH$_3$)$_3$), 1.44 (m, 1H, CH Leu), 2.46-2.89 (m, 2H, CH$_2$), 3.13 (m, 2H, CH$_2$), 4.12 (m, 1H, CHα), 4.38 (m, 1H, CHα), 4.70 (m, 1H, CHα), 5.02 (s, 2H, CH$_2$ (Bn)), 6.87-7.58 (m, 20H, 19 aromatic H and NH Boc), 7.94 (d, J=8.2 Hz, 1H), 8.17 (d, J=7.5 Hz, 1H), 10.0 (s, 1H, NH), 10.83 (s, 1H, NH). $^{13}$C NMR (75 MHz, DMSO-d$_6$) δ 21.5, 23.1, 23.9 (CH—(CH$_3$)$_2$), 27.7 (CH$_2$ Trp), 28.1 ((CH$_3$)$_3$), 36.2, 40.9 (CH$_2$ Tyr, CH$_2$ Leu), 50.9, 54.1, 55.7 (CHα Tyr, Leu, Tip), 69.0 (CH$_2$ (Bn)), 78.0 (C(CH$_3$)$_3$), 109.6, 111.2, 114.2, 118.2, 118.4, 119.3, 120.8, 123.3, 123.4, 127.3, 127.6, 127.7, 128.3, 128.6, 130.1, 130.3, 135.9, 137.2, 138.8 (25 aromatic C), 155.2, 156.8 (Car-O, CO carbamate), 170, 171.6, 171.9 (3 CO amide). Anal. Calcd. for C$_{44}$H$_{51}$N$_5$O$_6$: C, 70.85; H, 6.89; N, 9.39. Found: C, 70.52; H, 7.10; N, 9.33.

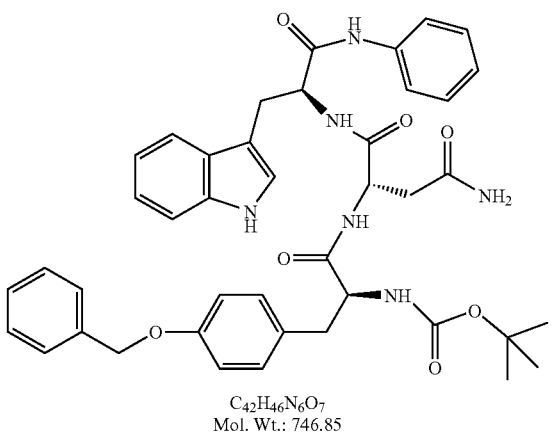

C$_{42}$H$_{46}$N$_6$O$_7$
Mol. Wt.: 746.85

N-Boc-Tyr(Bn)-Asn-Trp-NHPh: compound SP314C2. Same procedure as above with Trp-NHPh (102.9 mg, 0.368 mmol), N-Boc-Tyr(Bn)-Asn-OH (178.9 mg, 0.368 mmol), EDC (78.2 mg, 0.41 mmol) and HOBt (55 mg, 0.41 mmol) in CH$_2$Cl$_2$/DMF (1.5 mL, 1/1). The crude residue was purified by flash column chromatography on silica gel (0-5% MeOH/CH$_2$Cl$_2$) to give an off-white solid (82.8 mg, 30%). $^1$H NMR (300 MHz, DMSO-d$_6$) δ 1.28 (s, 9H, (CH$_3$)$_3$), 2.57-3.26 (m, 6H, CH$_2$ Tyr, CH$_2$ Trp, CH$_2$ Asn), 4.11 (m, 1H, CHα), 4.58

(m, 2H, 2 CHα), 5.03 (broad s, 2H, CH$_2$ (Bn)), 6.86-7.65 (m, 22H), 8.2 (m, 2H), 9.82 (s, 1H), 10.78 (s, 1H). $^{13}$C NMR (75 MHz, DMSO-d$_6$) δ 27.3 (CH$_2$ Trp), 28.1 ((CH$_3$)$_3$), 36.4, 37 (CH$_2$ Tyr, CH$_2$ Asn), 49.5, 54.5, 55.7 (CHα Tyr, Asn, Trp), 69 (CH$_2$ (Bn)), 78.1 (C(CH$_3$)$_3$), 109.7, 110, 111.2, 114.2, 118.2, 119.6, 120.8, 123.4, 123.6, 127.2, 127.5, 127.7, 128.3, 128.5, 130.1, 136, 137.2, 138.7 (25 aromatic C), 155.2, 156.8 (Car-O, CO carbamate), 170, 171, 171.7, 171.9 (4 CO amide). Anal. Calcd. for C$_{42}$H$_{46}$N$_6$O$_7$: C, 67.54; H, 6.21; N, 11.25. Found: C, 67.14; H, 6.27; N, 11.27.

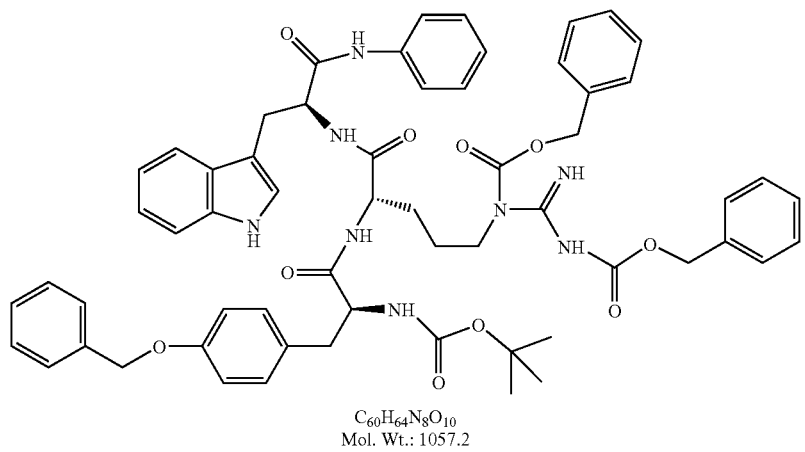

C$_{60}$H$_{64}$N$_8$O$_{10}$
Mol. Wt.: 1057.2

N-Boc-Tyr(Bn)-Arg(Z)-2-Trp-NHPh: compound SP310C. Same procedure as above with Trp-NHPh (100 mg, 0.358 mmol), N-Boc-Tyr(Bn)-Arg(Z)$_2$—OH (286 mg, 0.359 mmol), EDC (75.8 mg, 0.395 mmol) and HOBt (53.4 mg, 0.395 mmol) in CH$_2$Cl$_2$/DMF (1.8 mL, 1/1). The crude residue was purified by flash column chromatography on silica gel (0-1% MeOH/CH$_2$Cl$_2$) to give a yellow solid (157.4 mg, 41%). $^1$H NMR (300 MHz, DMSO-d$_6$) δ 1.25 (s, 9H, (CH$_3$)$_3$), 1.63 (m, 4H, 2 CH$_2$ Arg), 2.63 (m, 1H, CH$_2$ Tyr), 2.86 (m, 1H, CH$_2$ Tyr), 3.04 (dd, J=14.6 Hz, J=7.5 Hz, 1H, CH$_2$ Trp), 3.18 (dd, J=14.5 Hz, J=6.2 Hz, 1H, CH$_2$ Trp), 3.85 (m, 2H, CH$_2$ Arg), 4.11 (m, 1H, CHα), 4.36 (m, 1H, CHα), 4.7 (m, 1H, CHα), 5.01 (s, 4H, CH$_2$ (Bn), CH$_2$ (Z)), 5.17 (m, 2H, CH$_2$ (Z)), 6.85-7.54 (m, 30H), 7.94 (d, J=8 Hz, 1H), 8.24 (d, J=7.5 Hz, 1H), 9.15 (broad s, 2H), 10 (s, 1H), 10.8 (s, 1H) $^{13}$C NMR (75 MHz, DMSO-d$_6$) δ 24.9, 29.7 (2 CH$_2$ Arg), 27.8 (CH$_2$ Trp), 28 ((CH$_3$)$_3$), 36.3 (CH$_2$ Tyr), 44.3 (CH$_2$ Arg), 52.2, 54.2, 55.8 (CHα Tyr, Arg, Trp), 66.1, 68.1, 69.1 (CH$_2$ (Bn); 2 CH$_2$ (Z)), 78 (C(CH$_3$)$_3$), 109.5, 111.2, 114.2, 118.2, 118.4, 119.4, 120.8, 123.2, 123.5, 127.3, 127.5, 127.6, 127.7, 127.8, 128.1, 128.2, 128.3, 128.4, 128.6, 130.1, 130.2, 135.2, 136, 137, 137.2, 138.8 (37 aromatic C), 155, 155.2, 156.8, 159.6, 162.9 (Car-O, 3 CO carbamate, imine), 170, 171.3, 171.6 (3 CO amide). Anal. Calcd. for C$_{60}$H$_{64}$N$_8$O$_{10}$, 1H$_2$O: C, 67.02; H, 6.18; N, 10.42. Found: C, 67.34; H, 6.05; N, 10.27.

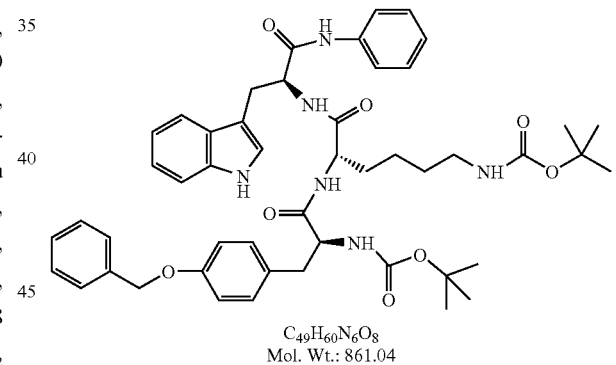

C$_{49}$H$_{60}$N$_6$O$_8$
Mol. Wt.: 861.04

N-Boc-Tyr(Bn)-Lys(Boc)-Trp-NHPh: compound SP306P. Same procedure as above with Trp-NHPh (99.6 mg, 0.356 mmol), N-Boc-Tyr(Bn)-Lys(Boc)-OH (214 mg, 0.356 mmol), EDC (75.3 mg, 0.392 mmol) and HOBt (53.7 mg, 0.397 mmol) in CH$_2$Cl$_2$/DMF (1.5 mL, 1/1). The crude residue was triturated with MeOH/pentane to afford a white solid (193.5 mg, 63%). $^1$H NMR (300 MHz, DMSO-d$_6$) δ 1.21-1.62 (m, 6H, 3 CH$_2$ Lys), 1.3 (s, 9H, (CH$_3$)$_3$), 1.36 (s, 9H, (CH$_3$)$_3$), 2.64 (m, 1H, CH$_2$ Tyr), 2.87 (m, 3H, CH$_2$ Lys, CH$_2$ Tyr), 3.05 (dd, J=14.7 Hz, J=7.7 Hz, 1H, CH$_2$ Trp), 3.19 (dd, J=14.7 Hz, J=6.2 Hz, 1H, CH$_2$ Trp), 4.11 (m, 1H, CHα), 4.31 (m, 1H, CHU), 4.71 (m, 1H, CHU), 5.02 (s, 2H, CH$_2$ (Bn)), 6.71 (m, 1H), 6.87-7.42 (m, 17H), 7.58 (m, 3H), 7.9 (d, J=7.3 Hz, 1H), 8.18 (d, J=7.2 Hz, 1H), 10 (s, 1H), 10.8 (s, 1H). $^{13}$C NMR (75 MHz, DMSO-d$_6$) δ 22.5, 29.2, 32 (3 CH$_2$ Lys), 27.8 (CH$_2$ Trp), 28.1, 28.2 (2 (CH$_3$)$_3$), 36.3 (CH$_2$ Tyr), 39.8 (CH$_2$ Lys), 52.4, 54.2, 55.8 (CHα Tyr, Lys, Trp), 69.1 (CH$_2$ (Bn)), 77.3, 78.1 (2 C(CH$_3$)$_3$), 109.6, 111.2, 114.3, 118.2, 118.4, 119.4, 120.8, 123.3, 123.4, 127.3, 127.5, 127.7, 128.3, 128.6, 130.1, 130.2, 136, 137.2, 138.8 (25 aromatic C), 155.2, 155.5, 156.8 (Car-O, 2 CO carbamate), 170.1, 171.5, 171.6 (3 CO amide). Anal. Calcd. for $C_{49}H_{60}N_6O_8$, $1.5H_2O$: C, 66.27; H, 7.15; N, 9.46. Found: C, 66.42; H, 6.96; N, 9.34.

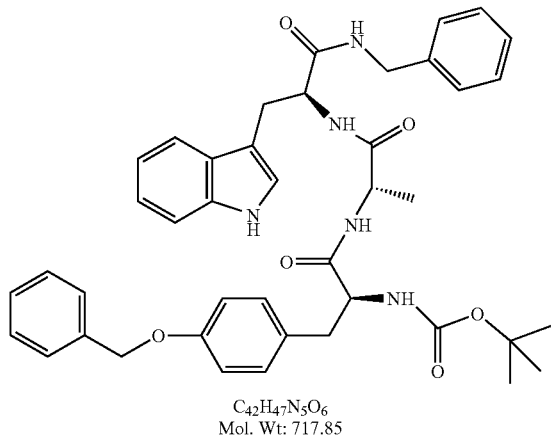

$C_{42}H_{47}N_5O_6$
Mol. Wt: 717.85

N-Boc-Tyr(Bn)-Ala-Trp-NHCCH$_2$Ph: compound SP304R. Same procedure as above with Trp-NHCH$_2$Ph (194.5 mg, 0.663 mmol), N-Boc-Tyr(Bn)-Ala-OH (293.5 mg, 0.663 mmol), EDC (141.5 mg, 0.73 mmol) and HOBt (99 mg, 0.73 mmol) in CH$_2$Cl$_2$/DMF (2.8 mL, 1/1). The crude residue was triturated with Et$_2$O/pentane to afford a white solid (215.5 mg, 45%). $^1$H NMR (300 MHz, DMSO-d$_6$) δ 1.22 (d, J=6.5 Hz, 3H, CH$_3$), 1.3 (s, 9H, (CH$_3$)$_3$), 2.61 (m, H, CH$_2$), 2.87 (m, 1H, CH$_2$), 3.02 (dd, J=14.1 Hz, 7 Hz, 1H, CH$_2$), 3.17 (dd, J=14.1 Hz, 6.1 Hz, 1H, CH$_2$), 4.24 (m, 4H, CH$_2$ (Bn) Trp, 2 CHα), 4.58 (m, 1H, CHα), 5.04 (s, 2H, CH$_2$ (Bn)), 6.89-7.44 (m, 19 aromatic H), 7.61 (d, J=7.7 Hz, 1H), 8.04 (d, J=7.1 Hz, 1H), 8.1 (d, J=7.6 Hz, 1H), 8.42 (m, 1H), 10.8 (s, 1NH). $^{13}$C NMR (75 MHz, DMSO-d$_6$) δ 18.2 (CH$_3$), 27.8 (CH$_2$ Trp), 28.1 ((CH$_3$)$_3$), 36.3 (CH$_2$ Tyr), 42 (CH$_2$ Bn (Trp)), 48.1, 53.5, 55.7 (CHα Ala, Tyr, Trp), 69 (CH$_2$ (Bn)), 78 (C(CH$_3$)$_3$), 109.7, 111.2, 114.2, 118.2, 118.4, 120.8, 123.6, 126.5, 126.9, 127.3, 127.5, 127.7, 128.1, 128.3, 130.2, 130.3, 136, 137.2, 139 (25 aromatic C), 155.2, 156.8 (Car-O, CO carbamate), 171, 171.4, 171.8 (3 CO amide). Anal. Calcd. for $C_{42}H_{47}N_5O_6$: C, 70.27; H, 6.6; N, 9.76. Found: C, 69.97; H, 6.73; N, 9.65.

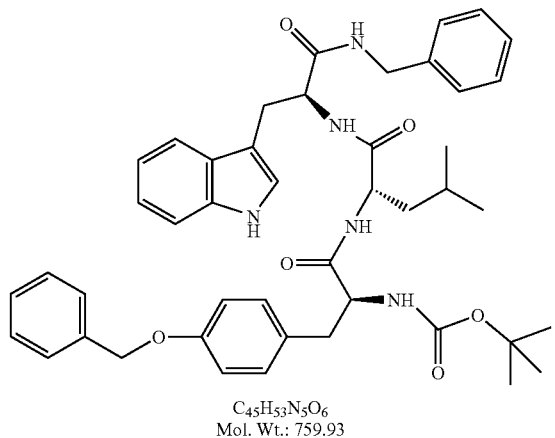

$C_{45}H_{53}N_5O_6$
Mol. Wt.: 759.93

N-Boc-Tyr(Bn)-Leu-Trp-NHCH$_2$Ph: compound A414P. Same procedure as above with Trp-NHCH$_2$Ph (136.8 mg, 0.467 mmol), N-Boc-Tyr(Bn)-Leu-OH (227 mg, 0.467 mmol), EDC (94 mg, 0.49 mmol) and HOBt (66 mg, 0.49 mmol) in CH$_2$Cl$_2$ (5 mL). The reaction mixture was diluted by CH$_2$Cl$_2$, washed with 2M aqueous Na$_2$CO$_3$, then 5% aqueous KHSO$_4$ and water. After drying of the organic phase over Na$_2$SO$_4$ and concentration in vacuo, the product was afforded as a white solid (232.9 mg, 66%). $^1$H NMR (300 MHz, DMSO-d$_6$) δ 0.82 (d, 3H, J=6.4 Hz, CH$_3$), 0.86 (d, 3H, J=6.4 Hz, CH$_3$), 1.30 (s, 9H, (CH$_3$)$_3$), 1.45 (m, 2H, CH$_2$ Leu), 1.59 (m, 1H, CH Leu), 2.59-2.88 (m, 2H, CH$_2$), 3.07 (m, 2H, CH$_2$), 4.08 (m, 1H, CHα), 4.20 (d, 2H, J=6 Hz, NCH$_2$Ph), 4.36 (m, 1H, CHα), 4.57 (m, 1H, CHα), 5.02 (s, 2H, OCH$_2$ (Bn)), 6.87-7.4 (m, 19H, 18 aromatic H and NH Boc), 7.58 (d, J=7.7 Hz, 1H), 7.95 (d, J=8 Hz, 1H), 8.11 (d, J=7.9 Hz, 1H), 8.4 (t, 1H, J=6 Hz, NH Bn), 10.84 (s, 1H, NH). $^{13}$C NMR (75 MHz, DMSO-d$_6$) δ 21.5, 23.1 (CH$_3$ Lou), 23.9 (CH$_2$ Leu), 27.8 (CH$_2$ Trp), 28.1 ((CH$_3$)$_3$), 41 (CH$_2$ Tyr), 42 (CH$_2$ (Bn Trp)), 51, 53.5, 55.8 (CHα Leu, Tyr, Trp), 69 (CH$_2$ (Bn)), 78 (C(CH$_3$)$_3$), 109.7, 111.2, 114.2, 118.2, 118.4, 120.8, 123.5, 126.5, 126.9, 127.3, 127.5, 127.7, 128.0, 128.3, 130.2, 130.3, 136, 137.2, 139 (25 aromatic C), 155.2, 156.8 (Car-O, CO carbamate), 171, 171.6, 171.7 (3 CO amide). Anal. Calcd. for $C_{45}H_{53}N_5O_6$: C, 71.12; H, 7.03; N, 9.22. Found: C, 70.85; H, 9.96; N, 9.07.

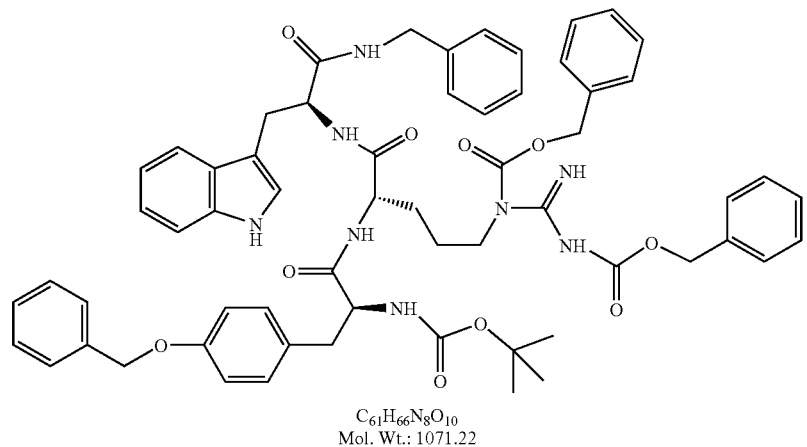

$C_{61}H_{66}N_8O_{10}$
Mol. Wt.: 1071.22

N-Boc-Tyr(Bn)-Arg(Z)-2-Trp-NHCH$_2$Ph: compound SP315C2. Same procedure as above with Trp-NHCH$_2$Ph (139 mg, 0.474 mmol), N-Boc-Tyr(Bn)-Arg(Z)$_2$—OH (378 mg, 0.474 mmol), EDC (100.2 mg, 0.523 mmol) and HOBt (70.8 mg, 0.523 mmol) in CH$_2$Cl$_2$/DMF (3 mL, 1/1). The crude residue was triturated with MeOH/pentane and the resulting white solid was purified by flash column chromatography on silica gel (0-1% MeOH/CH$_2$Cl$_2$) to give a white solid (249 mg, 49%). $^1$H NMR (300 MHz, DMSO-d$_6$) δ 1.25 (s, 9H, (CH$_3$)$_3$), 1.54 (m, 4H, 2 CH$_2$ Arg), 2.62-3.1 (m, 4H, CH$_2$ Tyr, CH$_2$ Trp), 3.85 (m, 2H, CH$_2$ Arg), 4.17 (m, 3H, CH$_2$ Bn (Trp), CHα), 4.33 (m, 1H, CHα), 4.58 (m, 1H, CHα), 5.02 (s, 4H, CH$_2$ (Bn), CH$_2$ (Z)), 5.21 (m, 2H, CH$_2$ (Z)), 6.81-7.39 (m, 29H), 7.58 (d, J=7.2 Hz, 1H), 7.97 (m, 1H), 8.12 (m, 1H), 8.37 (m, 1H), 9.16 (broad s, 2H), 10.8 (s, 1H). $^{13}$C NMR (75 MHz, DMSO-d$_6$) δ 24.8, 29.6 (2 CH$_2$ Arg), 27.8 (CH$_2$ Trp), 28 ((CH$_3$)$_3$), 36.3 (CH$_2$ Tyr), 42 (CH$_2$ (Bn) Trp), 44.3 (CH$_2$ Arg), 52.2, 53.7, 55.9 (CHα Tyr, Arg, Trp), 66.1, 68.1, 69 (CH$_2$ (Bn), 2 CH$_2$ (Z)), 78 (C(CH$_3$)$_3$), 109.6, 111.2, 114.2, 118.2, 118.4, 120.8, 123.6, 126.5, 126.9, 127.3, 127.5, 127.7, 127.8, 127.9, 128, 128.2, 128.3, 128.4, 128.5, 130.1, 135.2, 136, 137, 137.1, 138.9 (37 aromatic C), 155, 155.2, 156.8, 159.6, 162.9 (Car-O, 3 CO carbamate, imine), 171, 171.1, 171.6 (3 CO amide). Anal. Calcd. for C$_{61}$H$_{66}$N$_8$O$_{10}$, 0.5H$_2$O: C, 67.82; H, 6.25; N, 10.37. Found: C, 67.69; H, 6.13; N, 10.29.

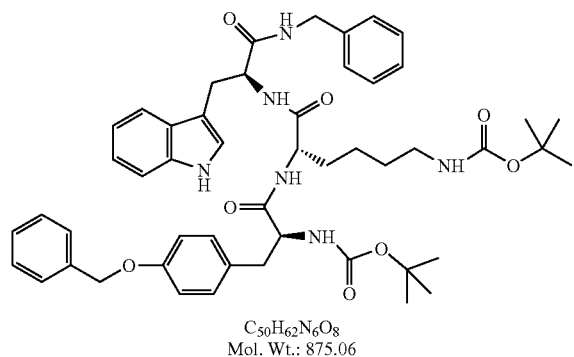

C$_{50}$H$_{62}$N$_6$O$_8$
Mol. Wt.: 875.06

N-Boc-Tyr(Bn)-Lys(Boc)-Trp-NHCH$_2$Ph: compound SP307P. Same procedure as above with Trp-NHCH$_2$Ph (120.7 mg, 0.411 mmol), N-Boc-Tyr(Bn)-Lys(Boc)-OH (246.9 mg, 0.411 mmol), EDC (87.1 mg, 0.45 mmol) and HOBt (62.1 mg, 0.46 mmol) in CH$_2$Cl$_2$/DMF (1.8 mL, 1/1). The crude residue was triturated with MeOH/pentane to afford a white solid (243 mg, 67%). $^1$H NMR (300 MHz, DMSO-d$_6$) δ 1.2-1.61 (m, 6H, 3 CH$_2$ Lys), 1.29 (s, 9H, (CH$_3$)$_3$), 1.36 (s, 9H, (CH$_3$)$_3$), 2.64 (m, 1H, CH$_2$ Tyr), 2.86 (m, 3H, CH$_2$ Lys, CH$_2$ Tyr), 3 (dd, J=14.1 Hz, J=7 Hz, 1H, CH$_2$ Trp), 3.14 (dd, J=14.1 Hz, J=6 Hz, 1H, CH$_2$ Trp), 4.11 (m, 1H, CHα), 4.26 (m, 3H, CH$_2$ (Bn Trp), CHα), 4.59 (m, 1H, CHα), 5.02 (broad s, 2H, CH$_2$ (Bn)), 6.72 (m, 1H), 6.85-7.4 (m, 19H), 7.59 (d, J=7.6 Hz, 1H), 7.89 (d, J=7.4 Hz, 1H), 8.1 (d, J=7.4 Hz, 1H), 8.38 (m, 1H), 10.8 (s, 1H). $^{13}$C NMR (75 MHz, DMSO-d$_6$) δ 22.4, 29.2, 32 (3 CH$_2$ Lys), 27.8 (CH$_2$ Trp), 28.1, 28.2 (2 (CH$_3$)$_3$), 36.3 (CH$_2$ Tyr), 39.8 (CH$_2$ Lys), 42 (CH$_2$ (Bn Trp), 52.4, 53.5, 55.8 (CHα Tyr, Lys, Trp), 69.1 (CH$_2$ (Bn)), 77.3, 78 (2 C(CH$_3$)$_3$), 109.7, 111.2, 114.3, 118.2, 118.4, 120.8, 123.5, 126.5, 126.9, 127.3, 127.5, 127.7, 128, 128.3, 130.1, 130.2, 136, 137.2, 139 (25 aromatic C), 155.2, 155.5, 156.8 (Car-O, 2 CO carbamate), 171, 171.3, 171.6 (3 CO amide). Anal. Calcd. for C$_{50}$H$_{62}$N$_6$O, 2H$_2$O: C, 65.91; H, 7.30; N, 9.22. Found: C, 65.59; H, 7.06; N, 9.09.

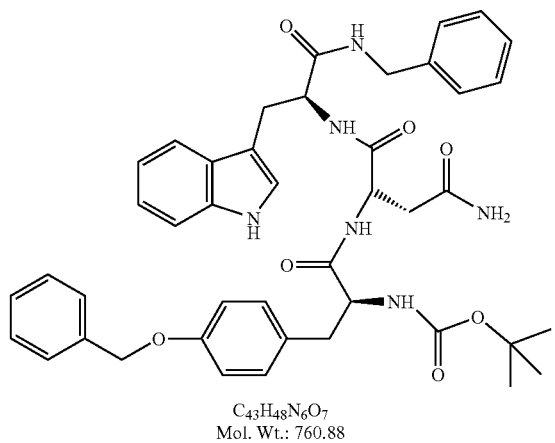

C$_{43}$H$_{48}$N$_6$O$_7$
Mol. Wt.: 760.88

N-Boc-Tyr(Bn)-Asn-Trp-NHCH$_2$Ph: compound A416. Same procedure as above with Trp-NHCH$_2$Ph (63.03 mg, 0.215 mmol), N-Boc-Tyr(Bn)-Asn-OH (105.0 mg, 0.216 mmol), EDC (44 mg, 0.226 mmol) and HOBt (31 mg, 0.226 mmol) in CH$_2$Cl$_2$/DMF (1.5 mL/1.5 mL). After treatment, the crude residue was triturated with CH$_2$Cl$_2$/pentane to afford a white solid (78 mg, 48%). $^1$H NMR (300 MHz, DMSO-d$_6$) δ $^1$H NMR (300 MHz, DMSO-d$_6$) δ 1.29 (s, 9H, (CH$_3$)$_3$), 2.30-3.26 (m, 6H, CH$_2$ Tyr, CH$_2$ Trp, CH$_2$ Asn), 4.08 (m, 1H, CHα), 4.24 (s, 2H, NCH$_2$Ph), 4.49 (m, 1H, CHα), 4.56 (m, 1H, CHα), 5.03 (broad s, 2H, OCH$_2$Ph), 6.88-7.56 (m, 17H), 8.17 (d, J=8 Hz, 1H, NH), 8.23 (d, J=8 Hz, 1H, NH), 8.51 (t, J=6 Hz, 1H, NH), 10.84 (s, 1H, NH). $^{13}$C NMR (75 MHz, CD$_3$OD) δ 28.5 (CH$_2$ Trp), 28.6 ((CH$_3$)$_3$), 37.3, 38.1 (CH$_2$ Tyr, CH$_2$ Asn), 44.1 (NCH$_2$Ph), 51.7, 55.9, 57.6 (CHα Tyr, Asn, Trp), 71.0 (OCH$_2$Ph), 80.9 (C Boc), 110.9 (C), 112.4, 115.9, 116.0, 119.4, 119.9, 122.5, 124.8, 128.0, 128.5, 128.6, 128.8, 129.4, 129.5, 130.6 (C), 131.4 (CH), 138.0, 138.8, 139.5 (aromatic C), 157.9, 159.1 (aromatic C and CO Boc), 172.7, 173.6, 174.4, 174.9 (CO amide).

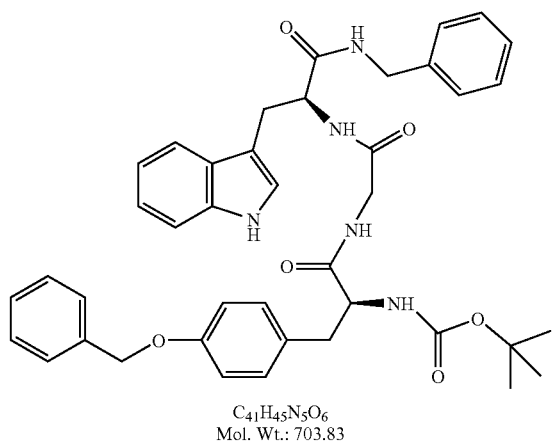

C$_{41}$H$_{45}$N$_5$O$_6$
Mol. Wt.: 703.83

N-Boc-Tyr(Bn)-Gly-Trp-NHCH$_2$Ph: compound PSV11R. Same procedure as above with Trp-NHCH$_2$Ph (82.43 mg, 0.281 mmol), N-Boc-Tyr(Bn)-Gly-OH (109.26 mg, 0.255 mmol), EDC (53.87 mg, 0.281 mmol) and HOBt (37.97 mg, 0.281 mmol) in CH$_2$Cl$_2$/DMF (2 mL/0.8 mL). The crude residue was triturated with CH$_2$Cl$_2$/pentane to afford a white solid (113.76, 63%). mp 183° C. $^1$H NMR (300 MHz, CDCl$_3$) δ 1.38 (s, 9H, (CH$_3$)$_3$), 2.81 (m, 2H, CH$_2$ Tyr), 3.26 (m, 2H), 3.72 (m, 2H, CH$_2$ Gly), 4.30 (m, 3H, CHα and CH$_2$Bn), 4.80 (m, 1H, CHα), 5.0 (broad s, 3H, NHBoc and CH$_2$O), 6.72 (m, 1H, NH Gly), 6.90-7.40 (m, 20H, aromatic H and NH), 7.63 (d, 1H, J=7 Hz), 8.35 (s, 1H, NH indole). $^{13}$C NMR (75 MHz, CDCl$_3$) δ 28.3 (CH$_2$ Trp and (CH$_3$)$_3$), 37.5 (CH$_2$ Tyr), 43.1, 43.5 (CH$_2$ (Bn), CH$_2$ Gly), 54.0, 55.8 (CHα Tyr, Trp), 70.0 (CH$_2$ (Bn)), 80.4 (C(CH$_3$)$_3$), 110.2, 111.3, 114.9, 118.7, 119.5, 122.0, 123.4, 127.2, 127.4, 127.5, 127.7, 128.0, 128.5, 128.6, 128.7, 130.3, 136.1, 137.0, 137.9 (20 aromatic C), 155.7, 157.7 (Car-O, CO carbamate), 168.9, 171.4, 172.5 (3 CO amide). Anal. Calcd. for C$_{41}$H$_{45}$N$_5$O$_6$, 1H$_2$O: C, 68.22; H, 6.56; N, 9.71. Found: C, 68.50; H, 6.48; N, 9.98.

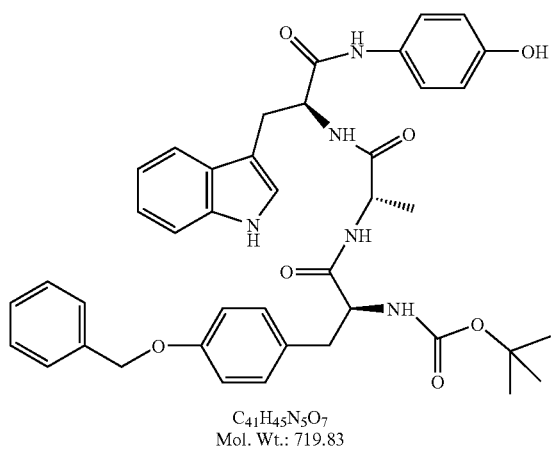

C$_{41}$H$_{45}$N$_5$O$_7$
Mol. Wt.: 719.83

N-Boc-Tyr(Bn)-Ala-Trp-NH(4-OH)Ph: compound SP313P. Same procedure as above with Trp-NHPhOH (75 mg, 0.254 mmol), N-Boc-Tyr(Bn)-Ala-OH (106.4 mg, 0.24 mmol), EDC (53.8 mg, 0.28 mmol) and HOBt (37.9 mg, 0.28 mmol) in CH$_2$Cl2/DMF (1.5 mL, 1/1). The crude residue was triturated with Et$_2$O to afford a pale brown solid (72.8 mg, 42%). $^1$H NMR (300 MHz, DMSO-d$_6$) δ 1.21 (d, J=6.7 Hz, 3H, CH$_3$), 1.28 (s, 9H, (CH$_3$)$_3$), 2.62-3.21 (m, 4H, CH$_2$ Tyr, CH$_2$ Trp), 4.1 (m, 1H, CHα), 4.32 (m, 1H, CHα), 4.64 (m, 1H, CHα), 5.02 (s, 2H, CH$_2$ (Bn)), 6.66 (d, J=8.4 Hz, 1H), 6.87-7.39 (m, 17H), 7.6 (d, J=7 Hz, 1H), 8 (d, J=6.9 Hz, 1H), 8.1 (d, J=7.1 Hz, 1H), 9.18 (s, 1 NH), 9.74 (s, 1 NH), 10.8 (s, 1H, NH). $^{13}$C NMR (75 MHz, DMSO-d$_6$) δ 18.2 (CH$_3$), 27.8 (CH$_2$ Trp), 28 ((CH$_3$)$_3$), 36.2 (CH$_2$ Tyr), 48.1, 53.9, 55.7 (CHα Ala, Tyr, Trp), 69 (CH$_2$ (Bn)), 78 (C(CH$_3$)$_3$), 109.6, 111.1, 114.2, 114.9, 118.1, 118.4, 120.7, 121, 123.4, 127.2, 127.5, 127.6, 128.3, 130.1, 130.2, 130.3, 135.9, 137.1 (24 aromatic C), 153.3, 155.2, 156.7 (2 Car-O, CO carbamate), 169.2, 171.4, 171.9 (3 CO amide). Anal. Calcd. for C$_{41}$H$_{45}$N$_5$O$_7$, 2H$_2$O: C, 65.14; H, 6.53; N, 9.26. Found: C, 65.08; H, 6.29; N, 9.92. HRMS (ESI) calcd for C$_{41}$H$_{45}$N$_5$O$_7$Na [(M+Na)$^+$] 742.3217. Found 742.3223.

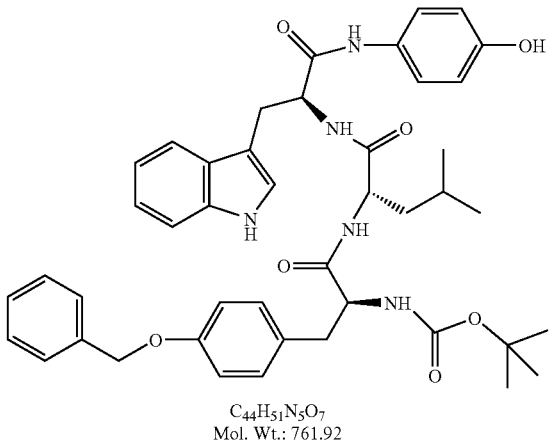

C$_{44}$H$_{51}$N$_5$O$_7$
Mol. Wt.: 761.92

N-Boc-Tyr(Bn)-Leu-Trp-NH(4-OH)Ph: compound A418P. Same procedure as above with Trp-NH(4-OH)Ph (58.99 mg, 0.2 mmol), N-Boc-Tyr(Bn)-Leu-OH (97 mg, 0.2 mmol), EDC (41 mg, 0.21 mmol) and HOBt (29 mg, 0.21 mmol) in CH$_2$Cl2/DMF (3 mL 1/1). The reaction mixture was diluted by CH$_2$Cl$_2$, washed with 2M aqueous Na$_2$CO$_3$, then 5% aqueous KHSO$_4$ and water. After drying of the organic phase over Na$_2$SO$_4$ and concentration in vacuo, the crude residue was triturated with Et$_2$O to afford a beige solid (118.36 mg, 78%). $^1$H NMR (300 MHz, DMSO-d$_6$) δ 0.83 (d, 3H, J=6.4 Hz, CH$_3$), 0.87 (d, 3H, J=6.5 Hz, CH$_3$), 1.30 (s, 9H, (CH$_3$)$_3$), 1.43 (m, 2H, CH$_2$ Leu), 1.6 (m, 1H, CH Leu), 2.64-2.89 (m, 2H, CH$_2$), 3.10 (m, 2H, CH$_2$), 4.12 (m, 1H, CHα), 4.37 (m, 1H, CHα), 4.65 (m, 1H, CHα), 5.02 (s, 2H, OCH$_2$ (Bn)), 6.65-7.43 (m, 18H, 17 aromatic H and NH Boc), 7.59 (d, J=7.7 Hz, 1H), 7.94 (d, J=8.9 Hz, 1H), 8.10 (d, J=7.6 Hz, 1H), 9.18 (s, 1H, OH), 9.72 (s, 1H, NHAr), 10.81 (s, 1H, NH). $^{13}$C NMR (75 MHz, DMSO-d$_6$) δ 22.0, 23.4 (CH$_3$ Leu), 25.7 (CH Leu), 28.7 ((CH$_3$)$_3$), 29 (CH$_2$ Trp), 38.1, 41.7 (CH$_2$ Leu, Tyr), 53.5, 56.1, 57.2 (CHα Leu, Tyr, Trp), 71 (CH$_2$ (OBn)), 80.7 (C(CH$_3$)$_3$), 110.8, 112.3, 115.9, 116.1, 119.5, 119.9, 122.5, 123.8, 124.6, 128.5, 128.8, 128.9, 129.5, 130.7, 131.0, 131.4, 138.0, 138.8 (24 aromatic C), 155.6, 157.7, 159.1 (2 Car-O, CO carbamate), 171.7, 174.3, 174.7 (3 CO amide). Anal. Calcd. for C$_{44}$H$_{51}$N$_5$O$_7$, 0.5H$_2$O: C, 68.55; H, 6.80; N, 9.08. Found: C, 68.21; H, 6.68; N, 9.09.

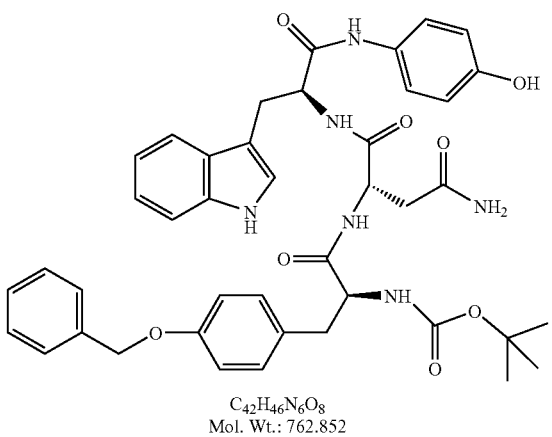

C$_{42}$H$_{46}$N$_6$O$_8$
Mol. Wt.: 762.852

N-Boc-Tyr(Bn)-Asn-Trp-NH(4-OH)Ph: compound SP318C. Same procedure as above with Trp-NHPh-OH 149c (104.4 mg, 0.353 mmol), N-Boc-Tyr(Bn)-Asn-OH 147c (171.3 mg, 0.353 mmol), EDC (74.9 mg, 0.39 mmol) and HOBt (52.6 mg, 0.39 mmol) in CH$_2$Cl$_2$/DMF (2.2 mL, 1/1). The crude residue was triturated with CH$_2$Cl$_2$/pentane and the resulting solid was purified by flash column chromatography on silica gel (5-8% MeOH/CH$_2$Cl$_2$) to give an off-white solid (118.9 mg, 44%). $^1$H NMR (300 MHz, DMSO-d$_6$) δ 1.28 (s, 9H, (CH$_3$)$_3$), 2.57-3.24 (m, 6H, CH$_2$ Tyr, CH$_2$ Trp, CH$_2$ Asn), 4.11 (m, 1H, CHα), 4.55 (m, 2H, 2 CHα), 5.03 (s, 2H, CH$_2$ (Bn)), 6.65-7.57 (m, 21H), 8.16 (m, 2H), 9.16 (s, 1H), 9.56 (s, 1H), 10.76 (s, 1H). $^{13}$C NMR (75 MHz, DMSO-d$_6$) δ 27.4 (CH$_2$ Trp), 28.1 ((CH$_3$)$_3$), 36.4, 37 (CH$_2$ Tyr, CH$_2$ Asn), 49.5, 54.3, 55.7 (CHα Tyr, Asn, Trp), 69.1 (CH$_2$ (Bn)), 78.1 (C(CH$_3$)$_3$), 109.9, 111.2, 114.2, 114.8, 118.2, 120.8, 121.3, $\overline{1}$23.5, 127.2, 127.5, 127.7, 128.3, 130.1, 130.2, 130.3, 130.4, 136, 137.2 (24 aromatic C), 153.4, 155.2, 156.8 (2 Car-O, CO carbamate), 169.1, 170.8, 171.6, 171.9 (4 CO amide). Anal. Calcd. for C$_{42}$H$_{46}$N$_6$O$_8$, 1 H$_2$O: C, 64.60; H, 6.19; N, 10.76. Found: C, 64.84; H, 6.00; N, 11.68.

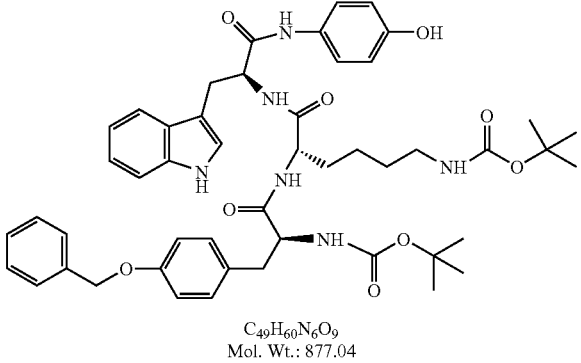

C$_{49}$H$_{60}$N$_6$O$_9$
Mol. Wt.: 877.04

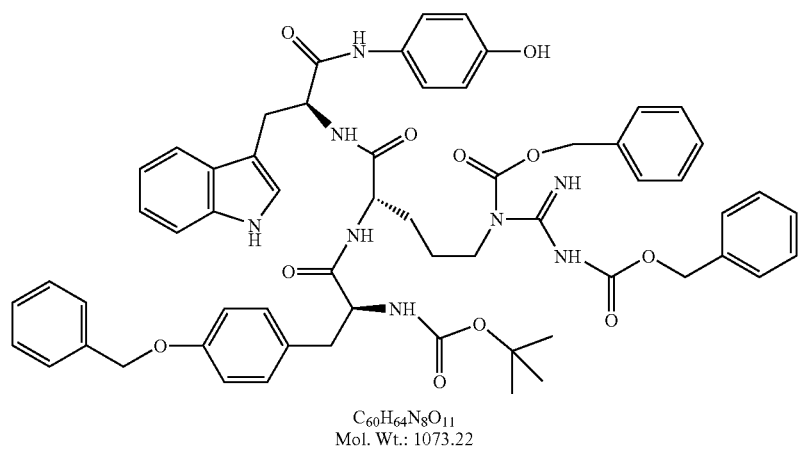

C$_{60}$H$_{64}$N$_8$O$_{11}$
Mol. Wt.: 1073.22

N-Boc-Tyr(Bn)-Arg(Z)-2-Trp-NH(4-OH)Ph: compound SP320P2. Same procedure as above with Trp-NHPhOH (112 mg, 0.357 mmol), N-Boc-Tyr(Bn)-Arg(Z)$_2$—OH (282 mg, 0.355 mmol), EDC (74.8 mg, 0.389 mmol) and HOBt (53.3 mg, 0.394 mmol) in CH$_2$Cl$_2$/DMF (2.2 mL, 1/1). The crude residue (235.8 mg) was purified by flash column chromatography on silica gel (1-2% MeOH/CH$_2$Cl$_2$) to give a yellowish solid (76.2 mg, 20%). $^1$H NMR (300 MHz, DMSO-d$_6$) δ 1.25 (s, 9H, (CH$_3$)$_3$), 1.62 (m, 4H, 2 CH$_2$ Arg), 2.6-3.2 (m, 4H, CH$_2$ Tyr, CH$_2$ Trp), 3.83 (m, 2H, CH$_2$ Arg), 4.11 (m, 1H, CHα), 4.35 (m, 1H, CHα), 4.65 (m, 1H, CHα), 5.01 (s, 4H, CH$_2$ (Bn), CH$_2$ (Z)), 5.17 (m, 2H, CH$_2$ (Z)), 6.63 (d, J=8.8 Hz, 2H), 6.85 (m, 2H), 6.93 (t, J=7.4 Hz, 1H), 7.02 (t, J=7.4 Hz, 1H), 7.12 (m, 2H), 7.28-7.42 (m, 20H), 7.59 (d, J=7.7 Hz, 1H), 7.95 (d, J=8 Hz, 1H), 8.18 (d, J=7.8 Hz, 1H), 9.15 (broad s, 3H), 9.74 (s, 1H), 10.8 (s, 1H). $^{13}$C NMR (75 MHz, DMSO-d$_6$) δ 24.9, 29.7 (2 CH$_2$ Arg), 27.8 (CH$_2$ Trp), 28 ((CH$_3$)$_3$), 36.3 (CH$_2$ Tyr), 44.3 (CH$_2$ Arg), 52.3, 54, 55.8 (CHα Tyr, Arg, Trp), 66.1, 68.1, 69 (CH$_2$ (Bn), 2 CH$_2$ (Z)), 78 (C(CH$_3$)$_3$), 109.6, 111.2, 114.2, 114.9, 118.1, 118.4, 120.8, $\overline{1}$21.1, 123.5, 127.3, 127.5, 127.6, 127.7, 127.8, 128.2, 128.3, 128.4, 128.5, 130.1, 130.3, 135.2, 136, 137, 137 (36 aromatic C), 153.3, 155 155.2, 156.8, 159.6, 162.9 (2 Car-O, 3 CO carbamate, imine), 169.2, 171.1, 171.6 (3 CO amide). Anal. Calcd. for C$_{60}$H$_{64}$N$_8$O$_{11}$, 4.5H$_2$O: C, 62.43; H, 6.37; N, 9.7. Found: C, 62.38; H, 5.82; N, 9.85.

N-Boc-Tyr(Bn)-Lys(Boc)-Trp-NH(4-OH)Ph: compound SP319P. Same procedure as above with Trp-NHPhOH (75 mg, 0.239 mmol), N-Boc-Tyr(Bn)-Lys(Boc)-OH (143 mg, 0.238 mmol), EDC (50.6 mg, 0.264 mmol) and HOBt (35.3 mg, 0.261 mmol) in CH$_2$Cl$_2$/DMF (1.6 mL, 1/1). The crude residue was triturated with MeOH/pentane to afford a white solid (142.5 mg, 68%). $^1$H NMR (300 MHz, DMSO-d$_6$) δ 1.21-1.61 (m, 6H, 3 CH$_2$ Lys), 1.29 (s, 9H, (CH$_3$)$_3$), 1.36 (s, 9H, (CH$_3$)$_3$), 2.64 (m, 1H, CH$_2$ Tyr), 2.86 (m, 3H, CH$_2$ Lys, CH$_2$ Tyr), 3.03 (dd, J=14.7 Hz, J=7.4 Hz, 1H, CH$_2$ Trp), 3.17 (dd, J=14.7 Hz, J=6 Hz, 1H, CH$_2$ Trp), 4.10 (m, 1H, CHα), 4.28 (m, 1H, CHα), 4.64 (m, 1H, CHα), 5.02 (s, 2H, CH$_2$ (Bn)), 6.65 (d, J=8.7 Hz, 2H), 6.72 (m, 1H), 6.88 (d, J=8.2 Hz, 2H), 6.94 (t, J=7.5 Hz, 1H), 7.03 (t, J=7.5 Hz, 1H), 7.13-7.42 (m, 12H), 7.6 (d, J=7.8 Hz, 1H), 7.9 (d, J=8 Hz, 1H), 8.12 (d, J=7.3 Hz, 1H), 9.17 (s, 1H), 9.73 (s, 1H), 10.8 (s, 1H). $^{13}$C NMR (75 MHz, DMSO-d$_6$) δ 22.5, 29.2, 32 (3 CH$_2$ Lys), 27.8 (CH$_2$ Trp), 28.1, 28.2 (2 (CH$_3$)$_3$), 36.3 (CH$_2$ Tyr), 39.7 (CH$_2$ Lys), 52.4, 54, 55.8 (CHα Tyr, Lys, Trp), 69 (CH$_2$ (Bn)), 77.3, 78.1 (2 C(CH$_3$)$_3$), 109.6, 111.2, 114.2, 115, 118.2, 118.4, 120.8, 12$\overline{1}$.1, 123.4, 127.3, 127.5, 127.7, 128.3, 130.1, 130.2, 130.4, 136, 137.2 (24 aromatic C), 153.3, 155.2, 155.5, 156.8 (2 Car-O, 2 CO carbamate), 169.3, 171.4, 171.6 (3 CO amide). Anal. Calcd. for C$_{49}$H$_{60}$N$_6$O$_9$, 3H$_2$O: C, 63.20; H, 7.14; N, 9.02. Found: C, 63.02; H, 6.75; N, 9.21.

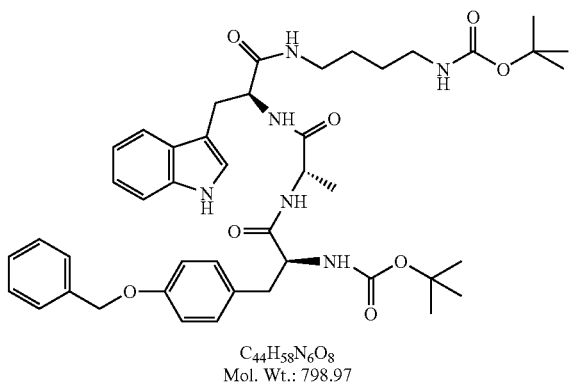

C₄₄H₅₈N₆O₈
Mol. Wt.: 798.97

N-Boc-Tyr(Bn)-Ala-Trp-NH(CH₂)₄NHBoc: compound SP305R. Same procedure as above with Trp-NH(CH₂)₄NH-Boc (204.6 mg, 0.546 mmol), N-Boc-Tyr(Bn)-Ala-OH (242 mg, 0.546 mmol), EDC (116 mg, 0.61 mmol) and HOBt (82.2 mg, 0.61 mmol) in CH₂Cl₂/DMF (2.2 mL, 1/1). The crude tripeptide (282 mg) can be recrystallized from hot THF to give a white solid as an analytical sample (89.1 mg, 31.5%). ¹H NMR (300 MHz, DMSO-d₆) δ 1.18-1.4 (m, 7H, 2 CH₂ putrescine, CH₃), 1.28 (s, 9H, (CH₃)₃), 1.37 (s, 9H, (CH₃)₃), 2.61 (m, 1H, CH₂ Tyr or Trp), 2.85-3.1 (m, 7H, CH₂ Tyr, CH₂ Trp, 2 CH₂ putrescine), 4.08 (m, 1H, CHα), 4.29 (m, 1H, CHα), 4.45 (m, 1H, CHα), 5.03 (s, 2H, CH₂ (Bn)), 6.73 (m, 1H), 6.87-7.43 (m, 14 aromatic H), 7.56 (d, J=7.7 Hz, 1H), 7.83 (m, 1H), 7.99 (m, 2H), 10.8 (s, 1NH). ¹³C NMR (75 MHz, DMSO-d₆) δ 18.2 (CH₃), 26.2, 26.8 (2 CH₂ putrescine), 28.1 (CH₂ Trp), 28.2 ((CH₃)₃), 36.3 (CH₂ Tyr), 38.2, 39.2 (2 CH₂ putrescine), 48.2, 53.4, 55.8 (CHα Ala, Tyr, Trp), 69 (CH₂ (Bn)), 77.3, 78 (2 C(CH₃)₃), 109.8, 111.1, 114.2, 118.1, 118.4, 120.7, 123.4, 127.3, 127.5, 127.7, 128.3, 130.1, 130.3, 136, 137.2 (19 aromatic C), 155.2, 155.5, 156.8 (Car-O, 2 CO carbamate), 170.7, 171.4, 171.8 (3 CO amide). Anal. Calcd. for C₄₄H₅₈N₆O₈: C, 66.14; H, 7.32; N, 10.52. Found: C, 65.89; H, 7.34; N, 10.77.

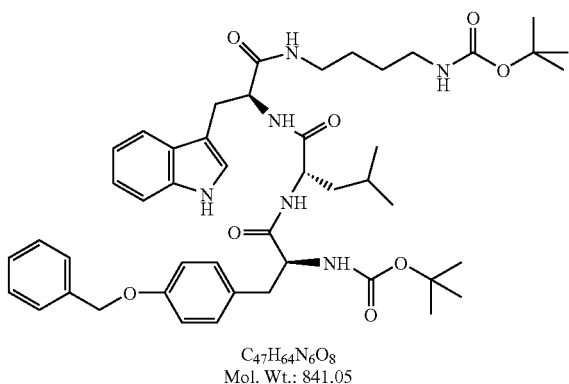

C₄₇H₆₄N₆O₈
Mol. Wt.: 841.05

N-Boc-Tyr(Bn)-Leu-Trp-NH(CH₂)₄NHBoc: compound SP296P. Same procedure as above with Trp-NH(CH₂)₄NH-Boc (264.7 mg, 0.706 mmol), N-Boc-Tyr(Bn)-Leu-OH (342.6 mg, 0.707 mmol), EDC (150.3 mg, 0.784 mmol), HOBt (105.3 mg, 0.78 mmol) and NEt₃ (0.39 mL, 2.8 mmol) in CH₂Cl₂/DMF (3 mL, 1/1). The crude residue was triturated with Et₂O/pentane to give a white solid (196.7 mg, 33%). ¹H NMR (300 MHz, DMSO-d₆) δ 0.82 (d, J=6.2 Hz, 3H, CH₃ Leu), 0.86 (d, S=6.2 Hz, 3H, CH₃ Leu), 1.25-1.41 (m, 4H, 2 CH₂ putrescine), 1.29 (s, 9H, (CH₃)₃), 1.36 (s, 9H, (CH₃)₃), 2.59-3.1 (m, 8H, CH₂ Tyr, CH₂ Trp, 2 CH₂ putrescine), 4.09 (m, 1H, CHα), 4.32 (m, 1H, CHα), 4.44 (m, 1H, CHα), 5.02 (s, 2H, CH₂ (Bn)), 6.71 (m, 1H), 6.87-7.4 (m, 14 aromatic H), 7.54 (d, J=7.7 Hz, 1H), 7.79 (m, 1H), 7.94 (m, 2H), 10.8 (s, 1NH). ¹³C NMR (75 MHz, DMSO-d₆) δ 20.3, 21.8, 22.7 (2 CH₃, CH Leu), 24.9, 25.5 (2 CH₂ putrescine), 26.7 (CH₂ Trp), 26.9, 27 (2 (CH₃)₃), 34.9 (CH₂ Tyr), 37, 39.2, 39.7 (2 CH₂ putrescine, CH₂ Leu), 49.8, 52.2, 54.6 (CHα Ala, Tyr, Trp), 67.8 (CH₂ (Bn)), 76, 76.8 (2 C(CH₃)₃), 108.6, 109.9, 113, 116.9, 117.1, 119.5, 122.1, 126.1, 126.3, 126.5, 127.1, 128.9, 129.1, 134.7, 136 (19 aromatic C), 154, 154.3, 155.6 (Car-O, 2 CO carbamate), 169.5, 170.3, 170.4 (3 CO amide). Anal. Calcd. for C₄₇H₆₄N₆O₈, 0.5H₂O: C, 66.40; H, 7.70; N, 9.88. Found: C, 66.34; H, 7.67; N, 10.07.

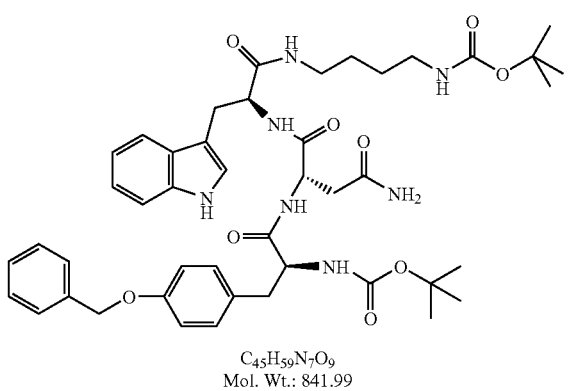

C₄₅H₅₉N₇O₉
Mol. Wt.: 841.99

N-Boc-Tyr(Bn)-Asn-Trp-NH(CH₂)₄NHBoc: compound SP323C2. Same procedure as above with Trp-NH(CH₂)₄NH-Boc (108.7 mg, 0.29 mmol), N-Boc-Tyr(Bn)-Asn-OH (140.9 mg, 0.29 mmol), EDC (61.8 mg, 0.32 mmol) and HOBt (43.6 mg, 0.32 mmol) in CH₂Cl₂/DMF (2 mL, 1/1). The crude residue was purified by flash column chromatography on silica gel (2-6% MeOH/CH₂Cl₂) to give an white solid (69.3 mg, 28%). ¹H NMR (300 MHz, DMSO-d₆) δ 1.18-1.37 (m, 4H, 2 CH₂ putrescine), 1.28 (s, 9H, (CH₃)₃), 1.37 (s, 9H, (CH₃)₃), 2.42-3.2 (m, 10H, CH₂ Tyr, CH₂ Trp, CH₂ Asn, 2 CH₂ putrescine), 4.1 (m, 1H, CHα), 4.36 (m, 1H, CHα), 4.53 (m, 1H, CHα), 5.03 (s, 2H, CH₂ (Bn)), 6.71 (m, 1H), 6.8-7.53 (m, 17H), 7.84 (m, 1H), 8.01 (d, J=9 Hz, 1H), 8.13 (d, J=7.6 Hz, 1H), 10.73 (s, 1H). ¹³C NMR (75 MHz, DMSO-d₆) δ 26.4, 27 (2 CH₂ putrescine), 27.4 (CH₂ Trp), 28.4 ((CH₃)₃), 36.6, 37.2 (CH₂ Tyr, CH₂ Asn), 38.4, 39.4 (2 CH₂ putrescine), 49.8, 54, 55.9 (CHα Tyr, Asn, Trp), 69.2 (CH₂ (Bn)), 77.5, 78.2 (C(CH₃)₃), 110.2, 111.3, 114.4, 118.3, 120.9, 123.6, 127.4, 127.7, 127.9, 128.5, 130.3, 130.4, 136.1, 137.4 (19 aromatic C), 155.4, 155.7, 157 (Car-O, 2 CO carbamate), 170.7, 170.9, 171.8, 172.1 (4 CO amide). Anal. Calcd. for C₄₅H₅₉N₇O₉: C, 64.19; H, 7.06; N, 11.64. Found: C, 63.97; H, 7.05; N, 11.76.

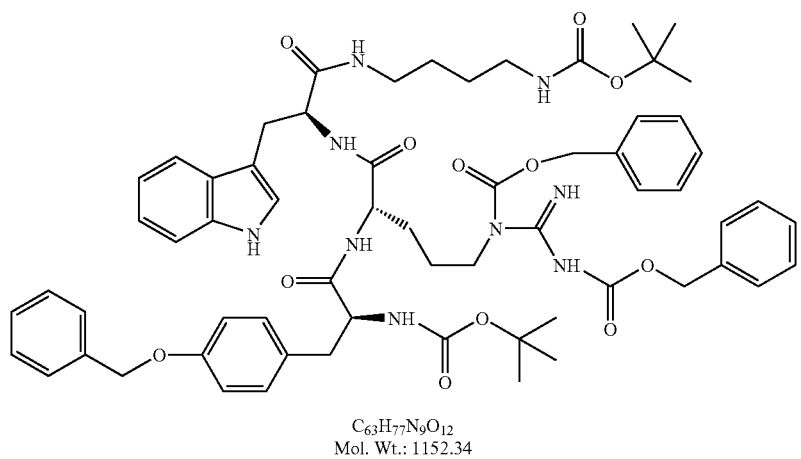

C$_{63}$H$_{77}$N$_9$O$_{12}$
Mol. Wt.: 1152.34

N-Boc-Tyr(Bn)-Arg(Z)-2-Trp-NH(CH$_2$)$_4$NHBoc: compound SP311C. Same procedure as above with Trp-NH(CH$_2$)$_4$NHBoc (105.7 mg, 0.282 mmol), N-Boc-Tyr(Bn)-Arg(Z)$_2$—OH (224.5 mg, 0.282 mmol), EDC (59.5 mg, 0.31 mmol) and HOBt (42.5 mg, 0.31 mmol) in CH$_2$Cl$_2$/DMF (1.8 mL, 1/1). The crude residue was purified by flash column chromatography on silica gel (0-2% MeOH/CH$_2$Cl$_2$) to give a white solid (191 mg, 58.7%). $^1$H NMR (300 MHz, DMSO-d$_6$) δ 1.11-1.35 (m, 4H, 2 CH$_2$ putrescine), 1.26 (s, 9H, (CH$_3$)$_3$), 1.35 (s, 9H, (CH$_3$)$_3$), 1.6 (m, 4H, 2 CH$_2$ Arg), 2.62 (m, 1H, CH$_2$ Tyr), 2.82-3.06 (m, 7H, CH$_2$ Tyr, CH$_2$ Trp, 2 CH$_2$ putrescine), 3.84 (m, 2H, CH$_2$ Arg), 4.09 (m, 1H, CHα), 4.31 (m, 1H, CHα), 4.46 (m, 1H, CHα), 5.02 (broad s, 4H, CH$_2$ (Bn), CH$_2$ (Z)), 5.23 (s, 2H, CH$_2$ (Z)), 6.69 (m, 1H), 6.85-7.55 (m, 26H), 7.8 (m, 1H), 7.97 (m, 2H), 9.16 (broad s, 2H), 10.76 (s, 1H). $^{13}$C NMR (75 MHz, DMSO-d$_6$) δ 24.8, 29.6 (2 CH$_2$ Arg), 26.1, 26.7 (2 CH$_2$ putrescine), 27.6 (CH$_2$ Trp), 28, 28.2 ((CH$_3$)$_3$), 36.3 (CH$_2$ Tyr), 38.2, 39.4 (2 CH$_2$ putrescine), 44.3 (CH$_2$ Arg), 52.3, 53.5, 55.9 (CHα Tyr, Arg, Trp), 66.1, 68.2, 69 (CH$_2$ (Bn), 2 CH$_2$ (Z)), 77.3, 78 (C(CH$_3$)$_3$), 109.7, 111.1, 114.2, 118.1, 118.4, 120.8, 123.4, 127.3, 127.4, 127.5, 127.7, 127.8, 127.9, 128.2, 128.3, 128.4, 128.5, 130.1, 130.2, 135.2, 135.9, 136, 137, 137.1 (31 aromatic C), 155, 155.1, 155.3, 159.6, 162.9 (Car-O, 3 CO carbamate, CO imine), 170.7, 171, 171.6 (3 CO amide). Anal. Calcd. for C$_{63}$H$_{77}$N$_9$O$_{12}$, 1H$_2$O: C, 64.65; H, 6.80; N, 10.77. Found: C, 64.81; H, 6.63; N, 10.54.

NH(CH$_2$)$_4$NHBoc (152.4 mg, 0.407 mmol), N-Boc-Tyr(Bn)-Lys(Boc)-OH (247.3 mg, 0.407 mmol), EDC (85.8 mg, 0.45 mmol) and HOBt (60.7 mg, 0.45 mmol) in CH$_2$Cl$_2$/DMF (1.8 mL, 1/1). The crude residue was triturated with MeOH/pentane to afford a white solid (255.9 mg, 65%). $^1$H NMR (300 MHz, DMSO-d$_6$) δ 1.29-1.57 (m, 10H, 3 CH$_2$ Lys, 2 CH$_2$ putrescine), 1.29 (s, 9H, (CH$_3$)$_3$), 1.36 (s, 9H, (CH$_3$)$_3$), 2.64 (m, 1H, CH$_2$ Tyr), 2.86-3.11 (m, 9H, CH$_2$ Lys, CH$_2$ Tyr, CH$_2$ Trp, 2 CH$_2$ putrescine), 4.10 (m, 1H, CHα), 4.26 (m, 1H, CHα), 4.46 (m, 1H, CHα), 5.03 (s, 2H, CH$_2$ (Bn)), 6.70 (broad s, 1H), 6.87-7.4 (m, 15H), 7.56 (d, J=7.6 Hz, 1H), 7.81-7.97 (m, 3H), 10.8 (s, 1H). $^{13}$C NMR (75 MHz, DMSO-d$_6$) δ 22.4, 29.2, 32 (3 CH$_2$ Lys), 26.2, 26.7 (2 CH$_2$ putrescine), 27.8 (CH$_2$ Trp), 28, 28.1, 28.2 (3 (CH$_3$)$_3$), 36.3 (CH$_2$ Tyr), 38.2, 39.5, 39.8 (2 CH$_2$ putrescine, CH$_2$ Lys), 52.4, 53.4, 55.8 (CHα Tyr, Lys, Trp), 69 (CH$_2$ (Bn)), 77.2, 78 (2 C(CH$_3$)$_3$), 109.8, 111.1, 114.2, 118.1, 118.4, 120.7, 123.4, 127.3, 127.5, 127.6, 128.3, 130.1, 135.9, 137.1 (19 aromatic C), 154.7, 155.5, 156.7 (Car-O, 2 CO carbamate), 170.7, 171.1, 171.5 (3 CO amide). Anal. Calcd. for C$_{52}$H$_{73}$N$_7$O$_{10}$: C, 65.32; H, 7.70; N, 10.25. Found: C, 65.30; H, 7.64; N, 10.04.

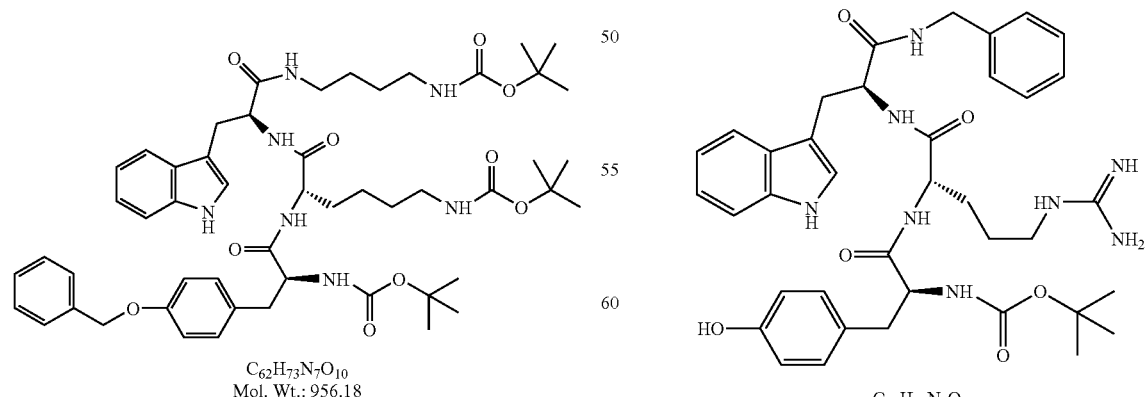

C$_{62}$H$_{73}$N$_7$O$_{10}$
Mol. Wt.: 956.18

C$_{38}$H$_{48}$N$_8$O$_6$
Mol. Wt.: 712.84

N-Boc-Tyr(Bn)-Lys(Boc)-Trp-NH(CH$_2$)$_4$NHBoc: compound SP308P. Same procedure as above with Trp- N-Boc-Tyr-Arg-Trp-NHCH$_2$Ph: compound SP325. A solution of N-Boc-Tyr(Bn)-Arg(Z$_2$)-Trp-NHCH$_2$Ph (86.15 mg, 0.0804 mmol) in MeOH/DMF (1.4 mL, 1/0.4) was hydrogenated at atmospheric pressure over 10% Pd on charcoal (9.14 mg) for 18 h. The mixture was filtered over a pad of celite and concentrated. The resulting residue was triturated in Et$_2$O and filtered to afford the product as a white solid (46.55 mg, 81%). $^1$H NMR (300 MHz, DMSO-d$_6$) δ 1.09-1.63 (m, 4H, (CH$_2$)$_2$ Arg), 1.30 (s, 9H, (CH$_3$)$_3$), 2.62-3.14 (m, 6H), 4.05 (m, 1H, CHα), 4.23 (m, 3H, CH$_2$ Ph and CHα), 4.56 (m, 1H, CHα), 6.60 (m, 2H, aromatic CH), 6.96-7.58 (m, 11H, aromatic H), 7.96 (m, 1H, aromatic H). $^{13}$C NMR (75 MHz, CD$_3$OD) δ 25.9 (CH$_2$ γ Lys), 28.7 (CH$_3$ Boc), 28.9, 29.9 (CH$_2$ Trp or CH$_2$ β Lys), 38.1 (CH$_2$ Tyr), 41.9 (CH$_2$N Lys), 44.2 (CH$_2$NPh), 54.3, 55.9, 57.9 (CH α Lys or Trp or Tyr), 80.9 (C Boc), 110.7 (Car), 112.4, 118.0, 119.4, 119.9, 122.5, 124.6 (CH ar), 126.0 (Car), 128.1, 128.4 (CH ar), 128.8 (Car), 129.4, 131.3 (CH ar), 138.0, 139.4 (Car), 157.9, 158.6, 161.5 (C=N or CarO or NCOO), 173.3, 173.8, 175.0 (CONH). HRMS (ESI) calcd for C$_{38}$H$_{49}$N$_8$O$_6$ [(M+H)$^+$] 713.3775. Found 713.3778.

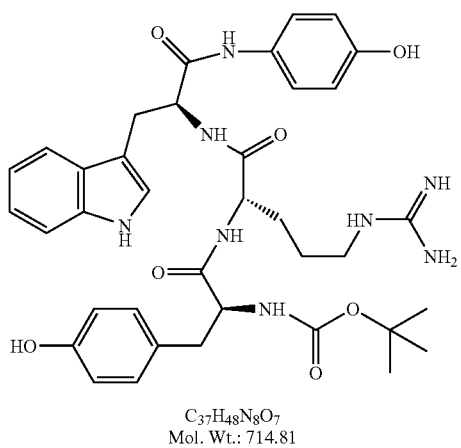

C$_{37}$H$_{48}$N$_8$O$_7$
Mol. Wt.: 714.81

N-Boc-Tyr-Arg-Trp-NH(4-OH)Ph: compound SP324. Same procedure as above using N-Boc-Tyr(Bn)-Arg(Z$_2$)-Trp-NH(4-OH)Ph (60.81 mg, 0.0567 mmol), 10% Pd on charcoal (6.43 mg) in MeOH/DMF (0.8 mL, 7/1) and affording N-Boc-Tyr-Arg-Trp-NH(4-OH)Ph as a beige solid (34.89 mg, 86%). $^1$H NMR (300 MHz, DMSO-d$_6$) δ 1.23-1.65 (m, 4H, (CH$_2$)$_2$ Arg), 1.31 (s, 9H, (CH$_3$)$_3$), 2.73-3.17 (m, 6H), 4.09 (m, 1H, CHα), 4.28 (m, 1H, CHα), 4.63 (m, 1H, CHα), 6.59 (m, 3H, aromatic CH), 6.92-7.31 (m, 7H, aromatic H), 7.57 (d, J=7.6 Hz, 1H, aromatic H). $^{13}$C NMR (75 MHz, CD$_3$OD) δ 26.1 (CH$_2$ γ Lys), 28.7 (CH$_3$ Boc), 26.7, 28.9 (CH$_2$ Trp or CH$_2$, Lys), 34.8 (CH$_2$ β Tyr), 41.9 (CH$_2$N Lys), 53.7, 56.4, 57.6 (CH α Lys or Trp or Tyr), 80.8 (C Boc), 110.6 (Car), 112.3, 116.9 (CH ar), 117.2 (C ar), 119.4, 119.9, 122.4, 124.1, 124.6 (CH ar), 128.7 (Car), 131.3 (CH ar), 138.0 (Car), 157.8, 158.4 (C=N or CarO or NCOO), 172.2, 173.3, 174.7 (CONH). HRMS (ESI) calcd for C$_{37}$H$_{47}$N$_8$O$_7$ [(M+H)$^+$] 715.3568. Found 715.3572.

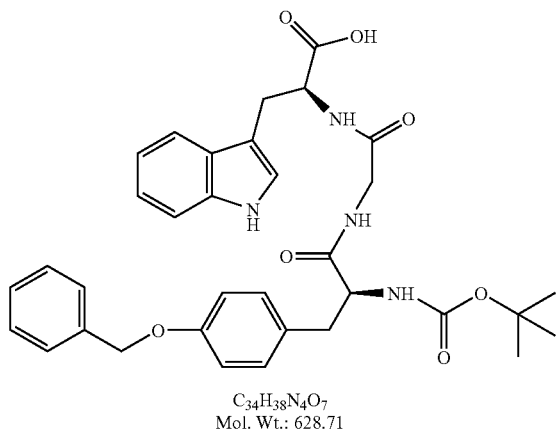

C$_{34}$H$_{38}$N$_4$O$_7$
Mol. Wt.: 628.71

N-Boc-Tyr(Bn)-Gly-Trp-OH: compound NR35. Saponification of N-Boc-Tyr(Bn)-Gly-Trp-OMe (242 mg, 0.385 mmol) in THF (0.5 mL) by 1 M aqueous LiOH (0.5 mL, 0.5 mmol) afforded after acidic treatment and precipitation of the residue with CH$_2$Cl$_2$/pentane N-Boc-Tyr(Bn)-Gly-Trp-OH as a white solid. $^1$H NMR (300 MHz, DMSO-d$_6$) δ 1.28 (s, 9H, (CH$_3$)$_3$), 2.63 and 3.01 (ABX system, 2H, CH$_2$β), 3.05 and 3.17 (ABX system, 2H, CH$_2$β), 3.73 (m, 2H, CH$_2$ Gly), 4.10 (m, 1H, CHα), 4.49 (m, 1H, CHα), 5.04 (broad s, 2H, CH$_2$O), 6.89 (m, 3H), 6.98 (t, J=7.1 Hz, 1H), 7.06 (t, J=6.8 Hz, 1H), 7.15 (m, 3H), 7.35 (m, 6H), 7.42 (d, J=6.5 Hz, 1H), 8.11 (m, 2H), 10.86 (s, 1H). $^{13}$C NMR (75 MHz, DMSO-d$_6$) δ 27.6 (CH$_2$ Trp), 28.5 (CH$_3$)$_3$), 37.0 (CH$_2$ Tyr), 42.2 (CH$_2$αGly), 53.4, 56.3 (CHα Tyr or Trp), 69.5 (CH$_2$ (OBn)), 78.4 (C Boc), 110.0 (aromatic C), 111.7, 114.7, 118.5, 118.7, 121.3, 124.1 (aromatic CH), 127.6 (aromatic C), 127.9, 128.1, 128.8, 130.6 (aromatic CH) 130.7, 136.4, 137.6 (aromatic C), 155.7, 157.2 (Car-O, CO carbamate), 168.9, 172.4, 172.5 (2 CO amide and COOH). Anal. Calcd. for C$_{34}$H$_{38}$N$_4$O$_7$, 1H$_2$O: C, 64.54; H, 6.37; N, 8.85. Found: C, 64.48; H, 6.35; N, 8.70.

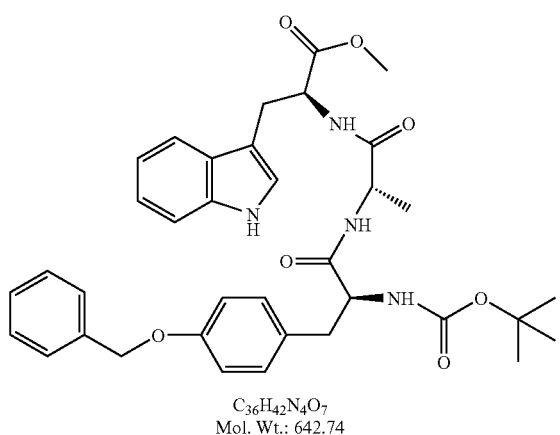

C$_{36}$H$_{42}$N$_4$O$_7$
Mol. Wt.: 642.74

N-Boc-Tyr(Bn)-Ala-Trp-OCH$_3$: compound NR36. Same procedure as above with HCl, Trp-OCH$_3$ (255 mg, 1 mmol), N-Boc-Tyr(Bn)-Ala-OH (444 mg, 1 mmol), DCC (259 mg, 1.26 mmol) and HOBt (172 mg, 1.27 mmol) in THF (15 mL). The crude residue was chromatographed over silica gel to afford a white solid (361 mg, 56%). $^1$H NMR (300 MHz, DMSO-d$_6$) δ 1.22 (d, J=7 Hz, 3H, CH$_3$), 1.29 (s, 9H, (CH$_3$)$_3$), 2.62 and 2.92 (ABX system, 2H, CH₂P), 3.08 and 3.13 (ABX system, 2H, CH₂β) 3.55 (s, 3H, OCH₃), 4.10 (m, 1H, CHα), 4.36 (m, 1H, CHα), 4.49 (m, 1H, CHα), 5.03 (s, 2H, CH₂ (OBn)), 6.85-7.50 (m, 15H, 14 aromatic H+1 NH), 7.97 (d, J=7.3 Hz, 1H), 8.34 (d, J=7.0 Hz, 1H), 10.88 (s, 1NH). ¹³C NMR (75 MHz, DMSO-d₆) δ 18.2 (CH₃), 26.8 (CH₂ Trp), 28.0 ((CH₃)₃), 36.3 (CH₂ Tyr), 47.6, 51.6, 53.0, 55.6 (CHα Ala, Tyr, Trp or OCH₃), 69 (CH₂ (OBn)), 77.9 (C(CH₃)₃), 109.0 (aromatic C), 111.2, 114.2, 117.8, 118.3, 120.8, 123.6 (aromatic CH), 126.9 (aromatic C), 127.4, 127.6, 128.2, 130.0 (aromatic CH), 130.2, 135.9, 137.1 (aromatic C), 155.1, 156.7 (Car-O or CO carbamate), 171.2, 171.9, 172.1 (2 CO amide or CO ester). Anal. Calcd. for C₃₆H₄₂N₄O₇, 0.5H₂O: C, 66.34; H, 6.65; N, 8.60. Found: C, 66.29; H, 6.64; N, 8.48.

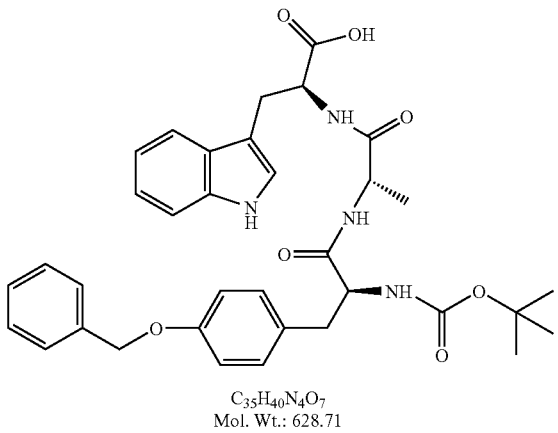

C₃₅H₄₀N₄O₇
Mol. Wt.: 628.71

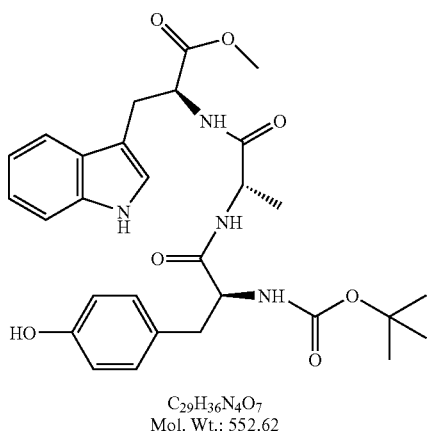

C₂₉H₃₆N₄O₇
Mol. Wt.: 552.62

N-Boc-Tyr-Ala-Trp-OCH₃: compound NR40. N-Boc-Tyr(Bn)-Ala-Trp-OMe (119 mg, 0.185 mmol) in solution in MeOH (4 mL) was hydrogenated overnight at atmospheric pressure in the presence of 10% Pd on charcoal (30 mg). After filtration, evaporation of the solvent and trituration with ether, N-Boc-Tyr-Ala-Trp-OMe (77 mg, 76%) was obtained as a solid. ¹H NMR (300 MHz, DMSO-d₆) δ 1.19 (d, J=7 Hz, 3H, CH₃), 1.29 (s, 9H, (CH₃)₃), 2.55 and 2.80 (ABX system, 2H, CH₂β), 3.13 and 3.16 (ABX system, 2H, CH₂β), 3.55 (s, 3H, OCH₃), 4.05 (m, 1H, CHα), 4.35 (m, 1H, CHα), 4.50 (m, 1H, CHα), 6.63 (d, J=8.3 Hz, 2H), 6.83 (d, J=8.6 Hz, 1H), 7.03 (m, 4H), 7.16 (d, J=2.1 Hz, 1H), 7.34 (d, J=7.9 Hz, 1H), 7.47 (d, J=7.8 Hz, 1H), 7.92 (d, J=7.4 Hz, 1H, NH), 8.32 (d, J=7.3 Hz, 1H, NH), 9.14 (s, 1H, OH), 10.86 (s, 1NH). ¹³C NMR (75 MHz, DMSO-d₆) δ 18.4 (CH₃); 26.9 (CH₂ Trp), 28.1 ((CH₃)₃), 36.4 (CH₂ Tyr), 47.8, 51.7, 53.0, 55.9 (CHα Ala, Tyr, Trp or OCH₃), 77.9 (C(CH₃)₃), 109.1 (aromatic C), 111.4, 114.8, 117.9, 118.4, 120.9, 123.7 (aromatic CH), 127.0, 128.2 (aromatic C), 130.0 (aromatic CH), 136.0 (aromatic C), 155.2, 156.6 (Car-O or CO carbamate), 171.4, 172.0, 172.2 (2 CO amide or CO ester). Anal. Calcd. for C₂₉H₃₆N₄O₇, 1H₂O: C, 61.04; H, 6.71; N, 9.82. Found: C, 61.02; H, 6.62; N, 9.66. HRMS (ESI) calcd for C₂₉H₃₆N₄O₇Na [(M+Na)⁺] 575.2482. Found 575.2480.

N-Boc-Tyr(Bn)-Ala-Trp-OH: compound NR66. Saponification of N-Boc-Tyr(Bn)-Ala-Trp-OMe (580 mg, 0.902 mmol) in THF (5 mL) by 1 M aqueous LiOH (2 mL, 2 mmol) at 4° C. for 1 hour, afforded after acidic treatment and precipitation of the residue with water crude N-Boc-Tyr(Bn)-Gly-Trp-OH. The crude product in MeOH (0.5 mL) was treated by dicyclohexylamine (0.18 mL, 0.91 mmol) and then ether (10 mL). After filtration, the resulting solid was dissolved in CH₂Cl₂ (10 mL) and washed by 10% aqueous citric acid. The organic phase was dried over MgSO₄ and concentrated to afford N-Boc-Tyr(Bn)-Ala-Trp-OH (361 mg, 64%) as a white solid. ¹H NMR (300 MHz, DMSO-d₆) δ 1.20 (d, J=7 Hz, 3H, CH₃), 1.28 (s, 9H, (CH₃)₃), 2.62 and 2.86 (ABX system, 2H, CH₂β), 3.09 and 3.18 (ABX system, 2H, CH₂β), 4.10 (m, 1H, CHα), 4.35 (m, 1H, CHα), 4.46 (m, 1H, CHα), 5.03 (s, 2H, CH₂ (OBn)), 6.87-7.54 (m, 15H, 14 aromatic H+1 NH), 7.96 (d, J=7.5 Hz, 1H), 8.13 (d, J=7.5 Hz, 1H), 10.84 (s, 1NH). ¹³C NMR (75 MHz, CDCl₃) δ 18.2 (CH₃), 27.2 (CH₂ Trp), 28.3 ((CH₃)₃), 37.3 (CH₂ Tyr), 48.9, 53.3, 55.7 (CHα Ala, Tyr or Trp), 70.0 (CH₂ (OBn)), 80.7 (C(CH₃)₃), 109.5 (aromatic C), 111.5, 115.0, 118.6, 119.5, 121.9, 123.8, 127.5, 127.6, 128.1, 128.6, 130.4 (aromatic CH), 136.1, 137.0, 137.1 (aromatic C), 155.8, 157.8 (Car-O or CO carbamate), 171.9, 172.3, 174.2 (2 CO amide or CO acid). Anal. Calcd. for C₃₅H₄₀N₄O₇, 1.5H₂O: C, 64.11%; H, 6.61%; N, 8.54%. Found: C, 64.19%; H, 6.36%; N, 8.79%.

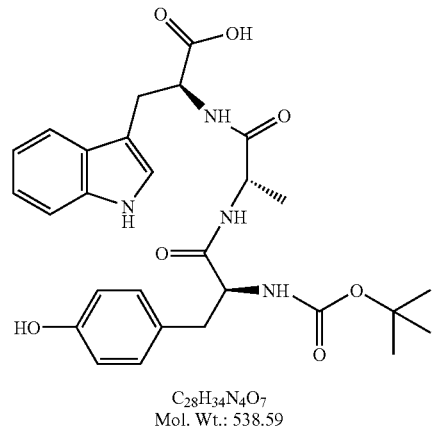

C₂₈H₃₄N₄O₇
Mol. Wt.: 538.59

N-Boc-Tyr-Ala-Trp-OH: compound NR68. N-Boc-Tyr(Bn)-Ala-Trp-OH (233 mg, 0.37 mmol) in solution in MeOH (4 mL) was hydrogenated overnight at atmospheric pressure in the presence of 10% Pd on charcoal (40 mg). After filtration, evaporation of the solvent and trituration with ether, N-Boc-Tyr-Ala-Trp-OMe was obtained as a solid (152 mg, 76%). H NMR (300 MHz, DMSO-d$_6$) δ 1.21 (d, J=7 Hz, 3H, CH$_3$), 1.29 (s, 9H, (CH$_3$)$_3$), 2.51 and 2.83 (ABX system, 2H, CH$_2$β), 3.05 and 3.20 (ABX system, 2H, CH$_2$>), 4.05 (m, 1H, CHα), 4.33 (m, 1H, CHα), 4.42 (m, 1H, CHα), 6.62 (d, J=8.3 Hz, 2H), 6.83 (d, J=8.6 Hz, 1H), 7.0 (m, 4H), 7.14 (d, J=2.1 Hz, 1H), 7.31 (d, J=7.9 Hz, 1H), 7.52 (d, J=7.7 Hz, 1H), 7.93 (d, J=7.5 Hz, 1H, NH), 8.09 (d, J=7.4 Hz, 1H, NH), 9.13 (s, 1H, OH), 10.82 (s, 1NH). $^{13}$C NMR (75 MHz, DMSO-d$_6$) δ 18.4 (CH$_3$), 27.0 (CH$_2$ Trp), 28.1 ((CH$_3$)$_3$), 36.4 (CH$_2$ Tyr), 47.9, 53.0, 55.9 (CHα Ala, Tyr or Trp), 78.0 (C(CH$_3$)$_3$), 109.6 (aromatic C), 111.3, 114.8, 118.1, 118.3, 120.8, 123.6 (aromatic CH), 127.1, 127.2 (aromatic C), 130.0 (aromatic CH), 136.0 (aromatic C), 155.2, 157.6 (Car-O or CO carbamate), 171.4, 172.0, 173.2 (2 CO amide or CO acid). Anal. Calcd. for C$_{29}$H$_{34}$N$_4$O$_7$, 2.5H$_2$O: C, 57.62%; H, 6.74%; N, 9.60%. Found: C, 57.66%; H, 6.57%; N, 9.45%.

VI) Preparation of Tripeptides Containing Oxotryptophane

Compounds IV-3

Hydrogenolysis of L-Z-Trp[O]—NHPh and Coupling to Dipeptides. General Procedure Applied to Boc-Tyr(Bn)-Arg(Z)-2-Trp[O]—NHPh: compound CV11. A mixture of L Z-Trp[O]—NHPh (1.29 g, 3 mmol) and 10% palladium on charcoal (259 mg) in DMF (20 mL) and MeOH (20 mL) was hydrogenated at atmospheric pressure for 5 h. After filtration over a pad of celite, the filtrate was concentrated and the resulting residue was washed with ether to afford L-Trp[O]—NHPh as a white solid (0.76 g, 85%).

To a solution of dipeptide Boc-Tyr(Bn)-Arg(Z)$_2$—OH (517.2 mg, 0.65 mmol) in CH$_2$Cl$_2$ at 0° C. was added HOBt (97.5 mg, 0.72 mmol) and EDC, HCl (137.5 mg, 0.72 mmol). The mixture was stirred for 15 min at 0° C. before adding a solution of L-Trp[O]—NHPh (202.2 mg, 0.68 mmol) in DMF (1.5 mL). After stirring overnight at room temperature, the solvent was evaporated in vacuo. The residue was dispersed in water (3 mL), filtered and successively washed with water and Et$_2$O to afford the crude tripeptide (497 mg). After chromatography on silica gel (30 g, 4% MeOH/CH$_2$Cl$_2$), Boc-Tyr (Bn)-Arg(Z)-2-Trp[O]—NHPh was obtained as a white solid (262 mg, 37%). $^1$H NMR (300 MHz, DMSO-d$_6$), (64/36 mixture of diastereomers) δ 1.25 (s, 9H, (CH$_3$)$_3$), 1.30-1.69 (m, 4H, 2 CH$_2$ (Arg)), 1.89-2.88 (m, 4H, CH$_2$ Trp and CH$_2$ Tyr), 3.44 (m, 1H, CH oxindole), 3.87 (m, 2H, CH$_2$—N (Arg)), 4.11 (m, 1H, CH$_α$), 4.39 (m, 1H, CH$_α$), 4.87 (m, 1H, CH$_α$), 5.01-5.05 (m, 4H, 2 CH$_2$(Z)), 5.17 (m, 2H, CH$_2$ (Bn)), 6.83-7.56 (m, 29H, 28 aromatic H and NH), 8.06-8.62 (m, 2H, 2 NH), 9.15 (broad s, 2H, NH), 9.97 (s, 1H, NH), 10.39 and 10.45 (two s, 1H, oxindolic NH of dia 1 or dia 2). $^{13}$C NMR (75 MHz, DMSO-d$_6$) (mixture of diastereomers) δ 25 (CH$_2$ Arg), 28 (CH$_3$ Boc), 29.4 (CH$_2$ Arg), 33.3 (CH$_2$ Trp), 36.3 (CH$_2$ Tyr), 41.9 (CHγ Trp[O]), 44.4 (CH$_2$—N Arg), 50.9, 52.5, 55.8 (3 CHα), 66.1, 68.1, 69.1 (2 CH$_2$(Z) and CH$_2$(Bn)), 77.9 (C Boc), 109.3-142.5 (35 aromatic CH or C), 154.9, 155.1, 156.8, 159.6, 162.8 (3 CO carbamate, 1 Car-O and 1 C=NH), 169.8, 171.3, 171.8 (3 CO amide), 178.4 et 178.6 (oxindolic CO of dia 1 or dia2). Anal. Calcd. for C$_{60}$H$_{64}$N$_8$O$_{11}$: C, 67.15; H, 6.01; N, 10.44. Found: C, 67.04; H, 6.00; N, 10.15.

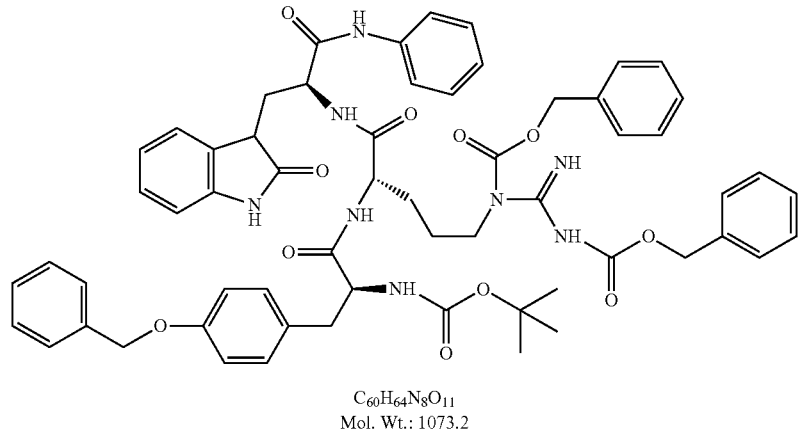

C$_{60}$H$_{64}$N$_8$O$_{11}$
Mol. Wt.: 1073.2

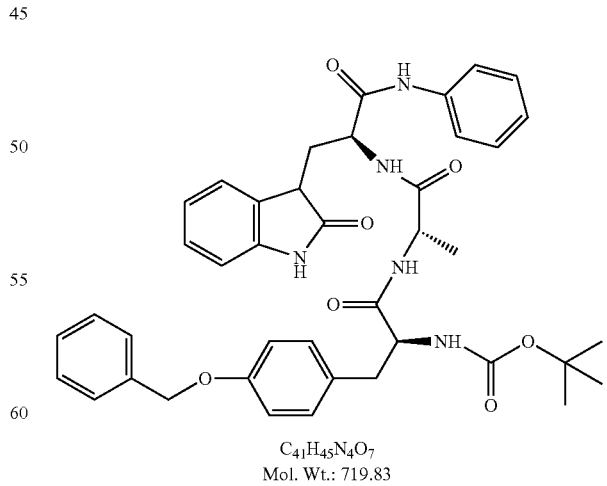

C$_{41}$H$_{45}$N$_4$O$_7$
Mol. Wt.: 719.83

Boc-Tyr(Bn)-Ala-Trp[O]—NHPh: compound CV13. The general procedure starting from dipeptide Boc-Tyr(Bn)-Ala-OH (144.2 mg, 0.32 mmol), HOBt (51.6 mg, 0.37 mmol), EDC, HCl (68.3 mg, 0.35 mmol) and Trp[O]—NHPh (98.7 mg, 0.35 mmol) afforded, after washing with ether (3×5 mL) the tripeptide Boc-Tyr(Bn)-Ala-Trp[O]—NHPh as a white solid (101.2 mg, 44%). ¹H NMR (300 MHz, DMSO-d₆) (50/50 mixture of diastereomers) δ 1.28 (broad s, 12H, CH₃ Boc and CH₃ Ala), 2.07-2.93 (m, 4H, CH₂ Trp[O] and CH₂ Tyr), 3.43 (s, 1H, CHγ Trp[O]), 4.13 (m, 1H, CHα), 4.35 (m, 1H, CHα), 4.8 (m, 1H, CHα), 5.03 (s, 2H, CH₂(Bn)), 6.87-7.61 (m, 19H, 18 aromatic H and NHBoc), 8.10 (m, 1H, NH), 8.28 and 8.53 (two d, 1H, J=7.6 Hz and J=9.0 Hz, dia 1 or dia 2 NH Trp[O]), 9.93 and 9.97 (two s, 1H, NHPh dia I or dia 2), 10.42 and 10.45 (two s, 1H, dia 1 or dia 2 NH oxindole). ¹³C NMR (75 MHz, DMSO-d₆) (mixture of two diastereomers) δ 18 (CH₃ Ala), 28.1 (CH₃ Boc), 33.3 (CH₂β Trp[O]), 36.3 (CH₂β Tyr), 41.9 (CHγ Trp[O]), 48.4, 51, 55.7 (3 CHα), 69.1 (CH₂(Bn)), 78 (C Boc), 109.3-142.5 (23 aromatic C), 155.2 and 156.8 (1 CO carbamate et 1 Car-O), 169.9, 171.1, 172.6 (3 CO amide), 178.5 and 178.6 (CO oxindole dia 1 or dia 2). Anal. Calcd. for C₄₁H₄₅N₅O₇, 1 H₂O: C, 66.73; H, 6.42; N, 9.49. Found: C, 67.06; H, 6.22; N, 9.57. HRMS (ESI) calcd for C₄₁H₄₅N₅O₇Na [(M+Na)⁺] 742.3217. Found 742.3234.

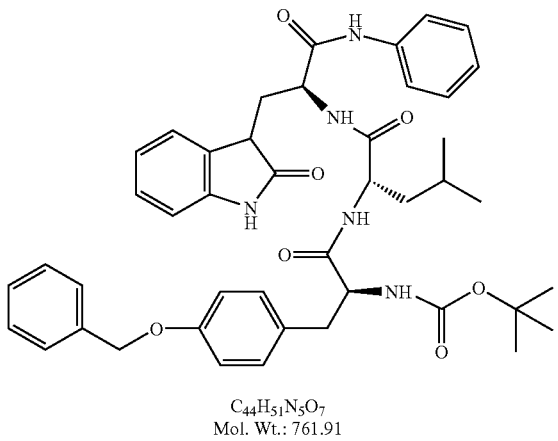

C₄₄H₅₁N₅O₇
Mol. Wt.: 761.91

Boc-Tyr(Bn)-Leu-Trp[O]—NHPh: compound JV602. The general procedure starting from Boc-Tyr(Bzl)-Leu-OH (109.5 mg, 0.226 mmol), HOBt (36.38 mg, 0.269 mmol), EDC, HCl (50.29, 0.262 mmol) and Trp[O]—NHPh (66.32 mg, 0.224 mmol) afforded the crude tripeptide as a solid which was suspended in boiling water (4 mL). After cooling to room temperature, filtration and washing with ether (3×5 mL), the tripeptide Boc-Tyr(Bn)-Leu-Trp[O]—NHPh was obtained as a white solid (117.9 mg, 69%). ¹H NMR (300 MHz, DMSO-d₆) (40/60 mixture of diastereomers dia1/dia2 which equilibrates to a 70/30 mixture within a few days at room temperature) δ 0.88-1.06 (m, 6H, CH₃ Leu), 1.23 and 1.29 (9H, dia1 and dia2, CH₃ Boc), 1.50-1.70 (m, 3H, CHγ and CH₂β Leu), 1.87-2.26 (m, 2H, CH₂β Trp[O]), 2.66-2.93 (m, 2H, CH₂β Tyr), 3.39-3.48 (m, 1H, CH₂γ Trp[O]), 4.11-4.15 (m, 1H, CHα Tyr), 4.33-4.45 (m, 1H, CHα Leu), 4.78-4.90 (m, 1H, CHα Trp[O]), 5.02 (broad s, 2H, CH₂O), 6.80-7.62 (m, 19H, 18 aromatic H and NH Boc), 7.62 and 7.97 (two d, 1H, J=6.8 Hz and J=6.8 Hz, dia 2 and dia 1 NH Leu), 8.31 and 8.58 (two d, 1H, J=6.3 Hz and J=7.7 Hz, dia 2 and dia 1 NH Trp[O]), 9.96 (s, 1H, NHPh), 10.42 and 10.46 (two s, 1H, dia2 and dia 1 indolic NH). ¹³C NMR (75 MHz, DMSO-d₆) (mixture of two diastereomers) δ 21.6, 21.7, 23.0, 23.1, 24.0, 27.8, 28.0 (CH and CH₃), 32.8, 33.2, 36.1, 40.8, 41.9 (CH₂), 50.9, 51.1, 51.7, 55.7 (CH), 69.0 (CH₂), 77.9, 78 (C), 109.3, 114.2, 119.3, 119.4, 121.2, 123.4, 124.2, 125.2, 127.6, 127.7, 128.3, 128.6, 128.9, 129.3, 130.1, 130.2, 130.3 (CH), 137.2, 138.7, 142.4, 142.5, 155.2, 156.8, 169.8, 171.8, 171.9, 172.4, 178.5, 178.6 (C). Anal. Calcd. for C₄₄H₅₁N₅O₇, 0.5H₂O: C, 68.55; H, 6.80; N, 9.07. Found: C, 68.56; H, 6.50; N, 9.25.

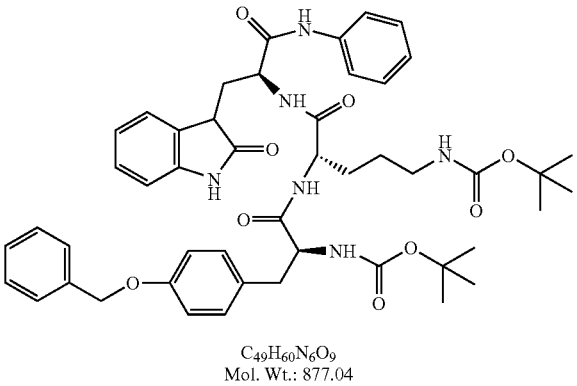

C₄₉H₆₀N₆O₉
Mol. Wt.: 877.04

Boc-Tyr(Bn)-Lys(Boc)-Trp[O]—NHPh: compound CV12. The general procedure starting from dipeptide Boc-Tyr(Bn)-Lys(Boc)-OH (392.3 mg, 0.65 mmol), HOBt (98.6 mg, 0.71 mmol), EDC, HCl (138.2 mg, 0.71 mmol) and Trp[O]—NHPh (201.3 mg, 0.65 mmol) afforded, after washing with ether (3×5 mL) the tripeptide Boc-Tyr(Bn)-Lys(Boc)-Trp[O]—NHPh as a white solid (273.3 mg, 48%). ¹H NMR (300 MHz, DMSO-d₆) (50/50 mixture of diastereomers) δ 1.29 and 1.36 (two s, 9H, CH₃ Boc), 1.51-1.56 (m, 6H, 3CH₂ Lys), 1.70-3.03 (m, 6H, CH₂β Trp[O], CH₂ β Tyr and CH₂—N (Lys)), 3.43 (m, 1H, CHγ Trp[O]), 4.14 (m, 1H, CHα), 4.32 (m, 1H, CHα), 4.80 (m, 1H, CHα), 5.02 (s, 2H, CH₂(Bn)), 6.63-7.63 (m, 20H, 18 aromatic H and 2 NH Boc), 7.97 (m, 1H, NH), 8.32 and 8.60 (two d, 1H, J=6.9 Hz and J=9.2 Hz, NH Trp[O] of dia 1 or dia 2), 9.96 (s, 1H, NHPh), 10.41 and 10.46 (two s, 1H, indolic NH of dia 1 or dia 2). ¹³C NMR (75 MHz, DMSO-d₆) δ 24.5 (CH₂ Lys), 30.1 and 30.2 (2 CH₃ Boc), 31.2 and 33.7 (2 CH₂ Lys), 35.2 (CH₂ Trp[O]), 38.3 (CH₂ Tyr), 41.4 (CH₂—NHBoc), 43.9 (CHγ Trp[O]), 53, 54.6, 57.7 (3 CHα), 71.1 (CH₂(Bn)), 79.3 and 80.1 (2 C Boc), 111.3-144.5 (23 aromatic C), 157.2, 157.5, 158.8 (2 CO carbamate and 1 Car-O), 171.9, 173.8, 174 (3 CO amide), 180.5 and 180.6 (CO oxindole dia 1 or dia 2). Anal. Calcd. for C₄₉H₆₀N₆O₉, 1.5H₂O: C, 65.09; H, 7.02; N, 9.29. Found: C, 65.20; H, 6.71; N, 9.66. HRMS (ESI) calcd for C₄₉H₆₀N₆O₉Na [(M+Na)⁺] 899.4319. Found 899.4322.

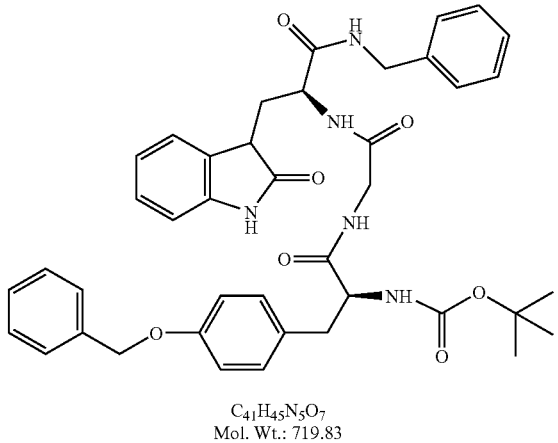

C₄₁H₄₅N₅O₇
Mol. Wt.: 719.83

Boc-Tyr(Bn)-Gly-Trp[O]—NHCH₂Ph: compound NR15. The general procedure starting from dipeptide Boc-Tyr(Bn)-Gly-OH (210 mg, 0.488 mmol), HOBt (67.6 mg, 0.5 mmol), EDC, HCl (94.1 mg, 0.49 mmol) and Trp[O]—NHCH₂Ph (139 mg, 0.449 mmol) afforded, after washing with ether (3×5 mL) the tripeptide Boc-Tyr(Bn)-Gly-Trp[O]—NHCH$_2$Ph as a white solid. $^1$H NMR (300 MHz, DMSO-d$_6$) (70/30 mixture of diastereomers) δ 1.19 and 1.27 (broad s, 9H, CH$_3$ Boc), 1.87-2.24 (m, 2H, CH$_2$ Trp[O]), 2.60-2.96 (m, 2H, CH$_2$ Tyr), 3.43 (m, 1H, CHγ Trp[O]), 3.82 (m, 2H, CH$_2$α Gly), 4.12 (m, 1H, CHα Tyr), 4.28 (broad s, 2H, CH$_2$ NBn), 4.75 (m, 1H, CHα Trp[O]), 5.04 (broad s, 2H, CH$_2$(Bn)), 6.83-7.44 (m, 19H, 18 aromatic H and NHBoc), 8.20 (m, 1H, NH), 8.43 and 8.52 (two d, 1H, J=8.6 Hz and J=6.0 Hz, dia 1 or dia 2 NH Trp[O]), 10.41 and 10.45 (two s, 1H, dia 1 or dia 2 NH oxindole). $^{13}$C NMR (75 MHz, DMSO-d$_6$) (mixture of two diastereomers) δ 28.1 (CH$_3$ Boc), 33.1 and 33.5 (CH$_2$β Trp[O]), 36.4 (CH$_2$β Tyr), 41.8 and 41.9 (CHγ Trp[O]), 42.1 and 42.2 (CH$_2$α Gly and CH$_2$ NBn), 50.1 and 50.8 (CHα Trp[O]), 55.8 ((CHα Tyr), 69.1 (CH$_2$(OBn)), 78.1 (C Boc), 109.2 and 109.3, 114.3, 121.2 and 121.3, 124.1 and 125, 126.1-130.3 (12 aromatic CH and 1 aromatic C), 137.2, 139.2 and 139.3, 142.4 and 142.5, 155.2 and 155.3 (4 aromatic C), 156.8 (1 CO Boc), 168, 8 and 169.2, 170.9 and 171.0, 172.1 (3 CO amide dia 1 or dia 2), 178.6 and 178.7 (CO oxindole dia 1 or dia 2). Anal. Calcd. for C$_{41}$H$_{45}$N$_5$O$_7$, 1H$_2$O: C, 66.73; H, 6.42; N, 9.49. Found: C, 66.30; H, 6.45; N, 9.97. HRMS (ESI) calcd for C$_{41}$H$_{45}$N$_5$O$_7$Na [(M+Na)$^+$] 742.3217. Found 742.3226.

for aromatic CH or C), 135.3, 137.1 and 137.2, 139.1 and 139.3, 142.5 and 142.6 (aromatic C), 155.0, 155.2, 156.8, 159.7, 163.0 (3 CO carbamate, 1 Car-0 or 1 C=NH), 170.9, 171.3, 171.8 (3 CO amide), 178.6 and 178.7 (indolic CO of dia 1 and dia2). Anal. Calcd. for C$_{61}$H$_{66}$N$_8$O$_{11}$: C, 67.39; H, 6.12; N, 10.31. Found: C, 67.15; H, 6.23; N, 10.32.

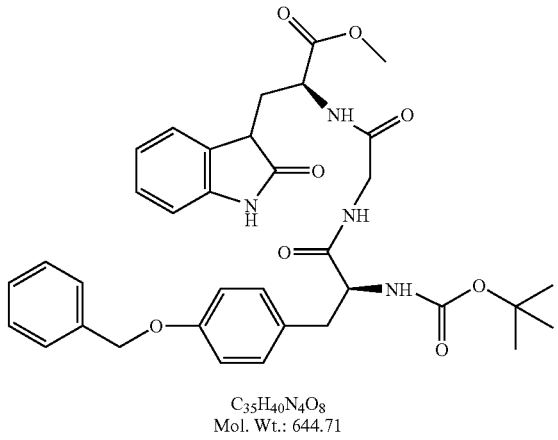

C$_{35}$H$_{40}$N$_4$O$_8$
Mol. Wt.: 644.71

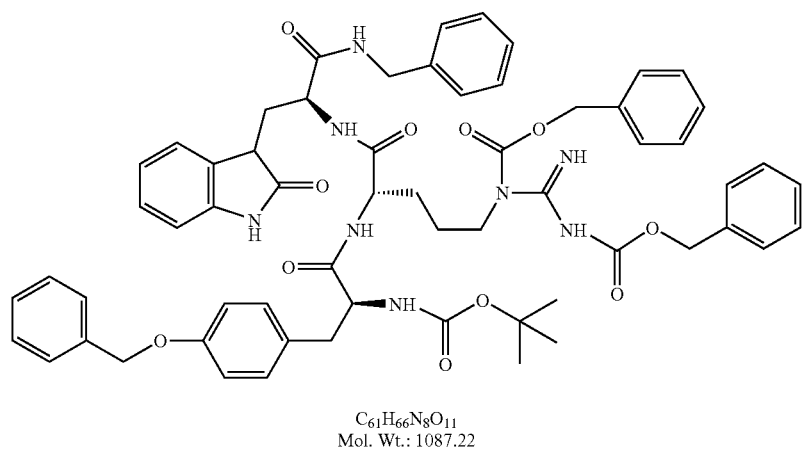

C$_{61}$H$_{66}$N$_8$O$_{11}$
Mol. Wt.: 1087.22

Boc-Tyr(Bn)-Arg(Z)-2-Trp[O]—NHCH$_2$Ph: compound NR16. The general procedure starting from dipeptide Boc-Tyr(Bn)-Arg(Z)$_2$—OH (389 mg, 0.49 mmol), HOBt (67.5 mg, 0.5 mmol), EDC, HCl (100.5 mg, 0.524 mmol) and Trp[O]—NHCH$_2$Ph (151 mg, 0.49 mmol) afforded, after chromatography over silica gel (MeOH/CH$_2$Cl$_2$ 1/20) the tripeptide Boc-Tyr(Bn)-Arg(Z)-2-Trp[O]—NHCH$_2$Ph as a white solid (151 mg, 28%). $^1$H NMR (500 MHz, DMSO-d$_6$), (64/36 mixture of diastereomers, COSY) δ 1.24 (broad s, 9H, (CH$_3$)$_3$), 1.62 (m, 4H, 2 CH$_2$ (Arg)), 1.89-2.30 (m, 2H, CH$_2$βTrp[O]), 2.52-2.84 (m, 2H, CH$_2$ Tyr) 3.38 (m, 1H, CHγ Trp[O]), 3.87 (m, 2H, CH$_2$—N (Arg)), 4.09 (m, 1H, CH$_α$ Tyr), 4.24 (m, 2H, CH$_2$ NBn), 4.37 (m, 1H, CH$_α$ Arg), 4.78 (m, 1H, CH$_α$ Trp[O]), 5.03 (broad s, 4H, 2 CH$_2$(Z)), 5.22 (broad s, 2H, CH$_2$ (OBn)), 6.83-7.40 (m, 29H, 28 aromatic H and NH), 8.05 and 8.12 (two d, 1H, J=8 Hz and J=7 Hz, NH Arg), 8.33 and 8.53 (two m, 1H, NH Trp[O]), 8.44 and 8.48 (two m, 1H, NHBn), 9.17 (brod s, 2H, NH), 10.40 and 10.46 (two s, 1H, oxindolic NH). $^{13}$C NMR (75 MHz, DMSO-d$_6$) (mixture of diastereomers) δ 24.9 (CH$_2$ Arg), 28.1 (CH$_3$ Boc), 29.3 (CH$_2$ Arg), 33.2 and 33.7 (CH$_2$ Trp[O]), 36.3 (CH$_2$ Tyr), 41.9 (CHγ Trp[O]), 42.1 (CH$_2$ NBn), 44.4 (CH$_2$—N Arg), 50.2, 52.6 (3 CHα), 66.1, 68.2, 69.1 (2 CH$_2$(Z) and CH$_2$(Bn)), 78.0 (C Boc), 109.3, 114.24, 121.3, 125.1-130.3 (17 signals Boc-Tyr(Bn)-Gly-Trp[O]—OCH$_3$: compound NR38. The general procedure starting from dipeptide Boc-Tyr(Bn)-Gly-OH (333 mg, 0.777 mmol), HOBt (115.7 mg, 0.856 mmol), EDC, HCl (164.4 mg, 0.857 mmol) and Trp[O]—OMe (0.778 mmol) afforded, after chromatography over silica gel (eluant AcOEt) the tripeptide Boc-Tyr(Bn)-Gly-Trp[O]—OMe as a white solid (119 mg, 24%). 111 NMR (300 MHz, DMSO-d$_6$) (55/45 mixture of diastereomers) δ 1.28 (broad s, 9H, CH$_3$ Boc), 2.08-2.30 (m, 2H, CH$_2$ Trp[O]), 2.60-2.96 (m, 2H, CH$_2$ Tyr), 3.41 (m, 1H, CHγ Trp[O]), 3.53 and 3.60 (two s, 3H, OCH$_3$), 3.77 (m, 2H, CH$_2$α Gly), 4.10 (m, 1H, CHα Tyr), 4.73 (m, 1H, CHα Trp[O]), 5.05 (broad s, 2H, OCH$_2$ (Bn)), 6.81-7.44 (m, 15H, 13 aromatic H and NHBoc), 8.18 (m, 1H, NH Gly), 8.18 and 8.51 (two d, 1H, J=7 Hz and J=8 Hz, NH Trp[O]), 10.44 and 10.46 (two s, 1H, NH oxindole). $^{13}$C NMR (75 MHz, CDCl$_3$) (mixture of two diastereomers) δ 28.3 (CH$_3$ Boc), 31.1 and 31.8 (CH$_2$β Trp[O]), 37.6 (CH$_2$β Tyr), 43.0 (CH$_2$α Gly), 43.4 (CHγ Trp[O]), 50.2 and 50.7 (CHα Trp [O]), 52.6 and 52.7 (OCH$_3$), 55.9 (CHα Tyr), 70.0 (CH$_2$(OBn)), 80.3 (C Boc), 110.3 and 110.4, 115.0, 122.7 and 122.8, 123.9 and 124.5 (aromatic CH), 127.5-130.5 (7 signals for aromatic CH and 2 aromatic C), 137.1, 141.6 and 141.8 (2 aromatic C), 155.9 and 156.0, 157.8 (1 CO Boc and 1 aromatic C), 169.1 and 169.2, 171.9 and 172.0, 172.4 and 172.5 (2 CO amide and 1 CO ester), 180.1 and 180.4 (CO oxindole). Anal. Calcd. for $C_{35}H_{40}N_4O_8$, $1H_2O$: C, 63.43; H, 6.39; N, 8.45. Found: C, 63.02; H, 6.25; N, 8.87. HRMS (ESI) calcd for $C_{35}H_{40}N_4O_8Na$ [(M+Na)$^+$] 667.2744. Found 667.2740.

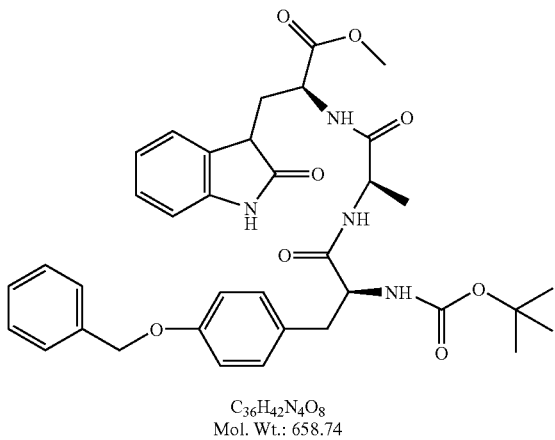

$C_{36}H_{42}N_4O_8$
Mol. Wt.: 658.74

Boc-Tyr(Bn)-Ala-Trp[O]—OCH$_3$: The general procedure starting from dipeptide Boc-Tyr(Bn)-Ala-OH, HOBt, EDC, HCl and Trp[O]—OMe afforded, after chromatography over silica gel the tripeptide Boc-Tyr(Bn)-Ala-Trp[O]—OMe.

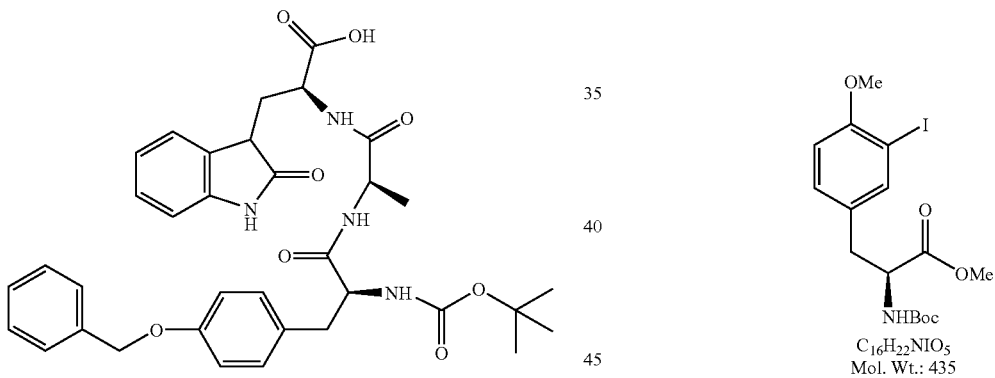

Boc-Tyr(Bn)-Ala-Trp[O]—OH: Saponification of Boc-Tyr(Bn)-Ala-Trp[O]—OMe in THF with aqueous LiOH afforded after acidification with aqueous HCl, Boc-Tyr(Bn)-Ala-Trp[O]—OH.

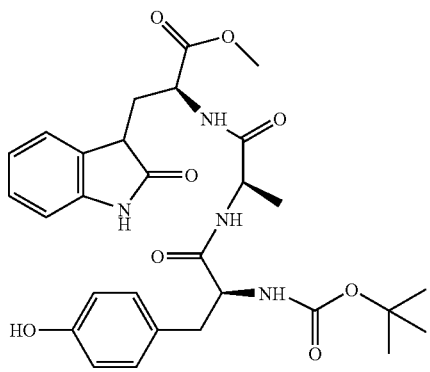

Boc-Tyr-Ala-Trp[O]—OCH$_3$: Stirring of a mixture of Boc-Tyr(Bn)-Ala-Trp[O]—OMe and 10% Pd/C under atmosphere of hydrogene afforded Boc-Tyr-Ala-Trp[O]—OMe

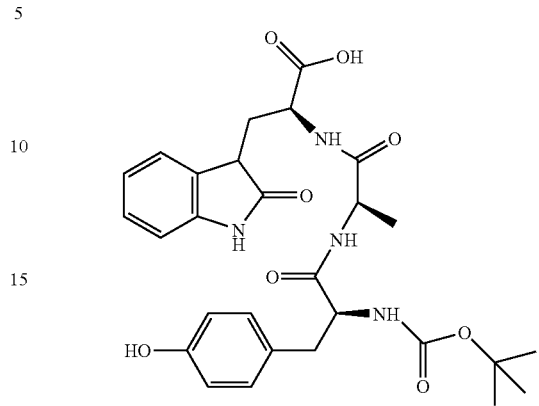

Boc-Tyr-Ala-Trp[O]—OH: Stirring of a mixture of Boc-Tyr(Bn)-Ala-Trp[O]—OH and 10% Pd/C under atmosphere of hydrogene afforded Boc-Tyr-Ala-Trp[O]—OH VII) Preparation of Homologues of Halogenated Tripeptides Compounds IV-1b $C_{16}H_{22}NIO_5$
Mol. Wt.: 435

N-Boc-3-iodo-Tyr(Me)-OMe: To a stirred suspension of $I_2$ (370 mg, 1.46 mmol) and $Ag_2SO_4$ (455 mg, 1.46 mmol) in MeOH (24 mL) was added Boc-Tyr(Me)-OMe (376 mg, 1.22 mmol) at room temperature. The mixture was stirred for 1 h. The yellow solid was removed by filtration over celite and the filtrate was concentrated off. The residue was dissolved in CHCl$_3$ and washed successively with aqueous 0.1 M $Na_2S_2O_3$, water and brine. The organic layer was dried over $Na_2SO_4$ and the solvent was evaporated under vacuum. Purification by flash chromatography on silica gel (1-5% MeOH/ $CH_2Cl_2$) yielded N-Boc-3-iodo-Tyr(Me)-OMe as a yellow foam (370 mg, 69%). $^1$H RMN (300 MHz, CDCl$_3$) δ 1.45 (s, 9H, (CH$_3$)$_3$), 3 (m, 2H, CH$_2$), 3.75 (s, 3H, OCH$_3$), 3.88 (s, 3H, OCH$_3$), 4.51 (m, 1H, CH), 5 (m, 1N, NHBoc), 6.76 (d, J=8.4 Hz, 1H, H5), 7.09 (dd, J=8.4 Hz, J=2.1 Hz, 1H, H6), 7.55 (d, J=2.1, 1H, H2). $^{13}$C NMR (75 MHz, CDCl$_3$) δ 28.3 ((CH$_3$)$_3$), 36.2 (CH$_2$), 52.2 (OCH$_3$), 54.5 (CH), 56.3 (OCH$_3$), 79.8 (C(CH$_3$)$_3$), 85.5 (C3), 110.8 (CH), 130.2 (C, CH), 140.1 (CH), 155 (C4), 157.1 (CO Boc), 172.1 (CO ester).

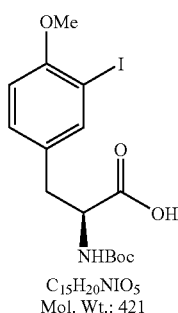

C₁₅H₂₀NIO₅
Mol. Wt.: 421

N-Boc-3-iodo-Tyr(Me)-OH: To a solution of N-Boc-3-iodo-Tyr(Me)-OMe (2.33 g, 5.35 mmol) in THF (30 mL) cooled at 0° C. was added a 1 M aqueous LiOH solution (5.9 mL). The mixture was stirred for 1 h 30 at 0° C. before it was quenched by 2 N aqueous HCl solution (pH=1-2). The aqueous phase was extracted twice by CH$_2$Cl$_2$, the combined organic layers were dried over Na$_2$SO$_4$. Removing of the solvents in vacuo afforded N-Boc-3-iodo-Tyr(Me)-OH (1.96 g, 100%) as a white foam which was used in the next step without further purification. $^1$H NMR (300 MHz, CDCl$_3$) (80:20 mixture of rotamers) δ 1.36 and 1.41 (two s, 9H, (CH$_3$)$_3$), 2.83 and 3.07 (two m, 2H, CH$_2$), 4.88 (s, 3H, OCH$_3$), 4.33 and 4.54 (two m, 1H, CH), 4.96 and 6.13 (two m, 1H, NHBoc), 6.78 (d, J=8.4 Hz, H5), 7.15 (dd, J=8.4 Hz, J=2.1 Hz, H6), 7.61 (d, J=2.1 Hz, 1H, H2). $^{13}$C NMR (75 MHz, CDCl$_3$) δ 28.1 and 28.1 ((CH$_3$)$_3$), 36.5 and 37.6 (CH$_2$), 53.6 and 54.5 (CH), 56.4 (OCH$_3$), 80.3 and 81.8 (C Boc), 85.9 (C3), 130.4 (CH), 130.7 (C), 140.2 (CH), 155.5 (C4), 157.1 and 156.7 (CO Boc), 175.6 (CO acid). Treatment of the crude acid with dicyclohexylamine (1.1 eq.) in Et$_2$O gave an analytical sample of the dicyclohexylamine salt. Anal. Calcd. for C$_{27}$H$_{43}$N$_2$O$_5$I, 0.5H$_2$O: C, 53.03; H, 7.25; N, 4.58. Found: C, 53.30; H, 7.10; N, 4.51.

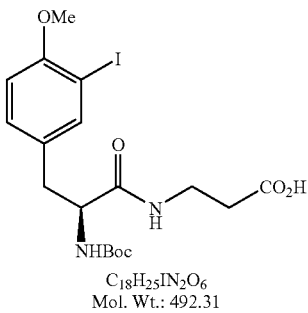

C₁₈H₂₅IN₂O₆
Mol. Wt.: 492.31

N-Boc-3-iodo-Tyr(Me)-βAla-OH: To the crude N-Boc-3-iodo-Tyr(Me)-OH (2.53 g, 6 mmol) in DME (12 mL) cooled at 0° C. was added DCC (1.32 g, 6.4 mmol) and SuOH (0.74 g, 6.4 mmol). The mixture was allowed to warm up overnight before filtration of the DCU precipitate. Washing of the solid with AcOEt and evaporation of the filtrate afforded the activated tyrosine ester (3 g, 100%) which was used in the next step without further purification. To a solution of the crude activated ester (200 mg, 0.36 mmol) in DMF was added βAla (35 mg, 0.38 mmol). The mixture was stirred overnight before being diluted with CH$_2$Cl$_2$ and washed with a 10% aqueous KHSO$_4$ solution. Drying over Na$_2$SO$_4$ and evaporation to dryness gave N-Boc-3-iodo-Tyr(Me)-βAla-OH. Purification by column chromatography (0-20% MeOH/CH$_2$Cl$_2$) afforded N-Boc-3-iodo-Tyr(Me)-βAla-OH (132 mg, 70%) as a white solid. $^1$H NMR (300 MHz, CDCl$_3$) δ 1.3 (s, 9H, (CH$_3$)$_3$), 2.36 (m, 2H, CH$_2$), 2.57-2.65 (m, 1H, CH$_2$), 2.8-2.84 (m, 1H, CH$_2$), 3.23-3.33 (m, 2H, CH$_2$), 3.78 (s, 3H, OCH$_3$), 4.02 (m, 1H, CH), 6.87 (d, J=8.7, 1H, NHBoc), 6.91 (d, J=8.4, 1H, H5), 7.23 (d, J=7.2, 1H, NH), 7.66 (m, 1H, aromatic H), 7.97 (m, 1H, aromatic H). Anal. Calcd. for C$_{18}$H$_{25}$IN$_2$O$_6$, H$_2$O: C, 42.36; H, 5.33; N, 5.49. Found: C, 42.03; H, 5.05; N, 5.34.

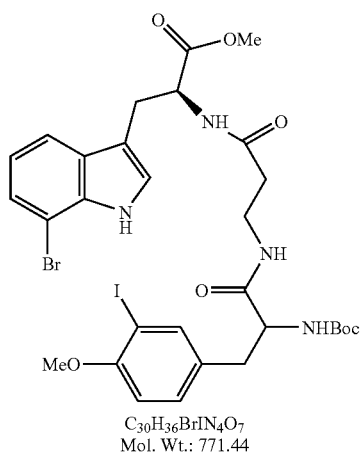

C₃₀H₃₆BrIN₄O₇
Mol. Wt.: 771.44

N-Boc-3-iodo-Tyr(Me)-βAla-7-bromo-Trp-OMe: compound A493. To a suspension of N-Boc-3-iodo-Tyr(Me)-βAla-OH (81 mg, 0.24 mmol), Boc-3-iodo-Tyr(Me)-OH (120 mg, 0.24 mmol), EDC (52 mg, 0.27 mmol) and HOBt (37 mg, 0.27 mmol) in CH$_2$Cl$_2$ (3 mL) was added NEt$_3$ (75 µL, 0.54 mmol) at 0° C. The resulting solution was allowed to warm up to room temperature overnight. The reaction mixture was washed successively with aqueous 5% KHSO$_4$, aqueous 0.5 M KHCO$_3$ and brine. The organic layer was dried over Na$_2$SO$_4$ and the solvent was removed in vacuo. The residue was subjected to flash chromatography on silica gel (1-3% MeOH/CH$_2$Cl$_2$) to afford N-Boc-3-iodo-Tyr(Me)-βAla-7-bromo-Trp-OMe (143 mg, 76%) as a white amorphous solid. $^1$H NMR (300 MHz, CDCl$_3$): δ 1.38 (s, 9H, (CH$_3$)$_3$), 2.23-2.45 (m, 2H, CH$_2$), 2.70-3.04 (m, 1H, CH$_2$ Tyr), 3.21-3.41 (m, 3H, CH$_2$ Trp, CH$_2$), 3.61-3.72 (m, 1H, CH$_2$), 3.79 (s, 3H, OCH$_3$), 3.85 (s, 3H, OCH$_3$), 4.19-4.32 (m, 1H, CHα Tyr), 4.83-4.93 (m, 1H, CHα Trp), 5.16 (m, 1H, NH), 6.36 (m, 1H, NH), 6.74 (d, J=8.4, H5 Tyr), 6.8 (broad s, 1H, NH), 7.03 (t, J=7.7 Hz, 1H, H7 Trp), 7.13 (m, 2 aromatic H), 7.36 (d, J=7.6 Hz, 1H, H4 Trp), 7.49 (d, J=7.9 Hz, H6 Trp), 7.57 (d, J=2 Hz, 1H, H2 Tyr), 8.52 (broad s, 1H, NHind). $^{13}$C NMR (75 MHz, CDCl$_3$) δ 27.3 (CH$_2$ Trp), 28.3 ((CH$_3$)$_3$), 35.9 (2 CH$_2$), 37 (CH$_2$ Tyr), 52.8 (OCH$_3$), 36.4 (OCH$_3$), 80.3 (C(CH$_3$)$_3$), 85.9 (C3 Tyr), 105 (C7 Trp), 110.9 (CH), 111.4 (C), 117.7 (CH), 120.9 (CH), 123.4 (C), 124.7 (CH), 128.6 (C), 130.4 (CH), 131 (C), 134.9 (CH), 140.2 (CH), 156 (C4 Tyr), 157 (CO Boc), 171.6, 171.8 (CO amide and CO ester). Anal. Calcd. for C$_{30}$H$_{361}$N$_4$O$_7$, 0.5H$_2$O: C, 46.17; H, 4.78; N, 7.18. Found: C, 46.39; H, 4.83; N, 7.04.

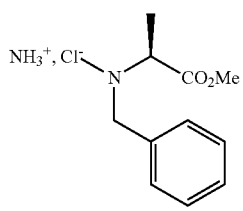

C₁₁H₁₇N₂O₂Cl
Mol. Wt.: 244.5

NH$_2$-(Bn)Ala-OMe hydrochloride salt: BocNH-(Bn)Ala (200 mg, 0.68 mmol prepared according to Hannachi, J. C.; Vidal, J.; Mulatier, J. C.; Collet, A., Electrophilic amination of amino acids with N-Boc-oxaziridines: efficient preparation of N-orthogonally diprotected hydrazino acids and piperazic acid derivatives. J. Org. Chem. 2004, 69, (7), 2367-2373) was solubilized in a 4.5 M anhydrous HCl solution in MeOH. The mixture was allowed to stir overnight and concentrated off. Precipitation of the residue in Et$_2$O and filtration afforded HCl, NH$_2$-(Bn)Ala-OMe (169 mg, 100%) as a white solid. $^1$H NMR (300 MHz, DMSO-d$_6$) δ 1.38 (d, J=7.2 Hz, 3H, CH$_3$), 3.41 (s, 3H, OCH$_3$), 3.95 (q, J=7.2 Hz, 1H, CH), 4.04 (d, J=13.8 Hz, 1H, CH$_2$), 4.14 (d, J=13.8 Hz, 1H, CH$_2$), 7.34 (m, 5 aromatic H), 9.71 (broad s, 3H, NH$_3$$^+$). $^{13}$C NMR (75 MHz, DMSO-d$_6$) δ 14.3 (CH$_3$), 52.6 (OCH$_3$), 57.8 (CH$_2$), 58 (CH), 128.5 (CH), 128.7 (CH), 129.6 (CH), 134 (C), 172 (CO ester).

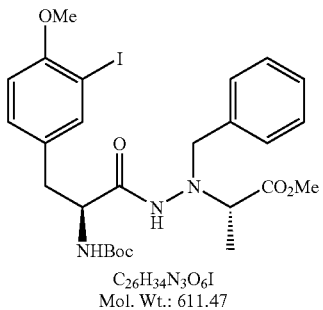

C₂₆H₃₄N₃O₆I
Mol. Wt.: 611.47

N-Boc-3-iodo-Tyr(Me)-NH-(Bn)Ala-OMe: To a suspension of HCl, NH$_2$-(Bn)Ala-OMe (100 mg, 0.41 mmol), Boc-3-iodo-Tyr(Me)-OH (172 mg, 0.41 mmol) and PyBOP (213 mg, 0.41 mmol) HOBt (37 mg, 0.27 mmol) in CH$_2$Cl$_2$ (1 mL) was added DIEA (196 μL, 1.13 mmol) at 0° C. The resulting solution was allowed to warm up and was stirred for 2 h. The reaction mixture was diluted in AcOEt and washed successively with aqueous 5% KHSO$_4$, aqueous 0.5 M KHCO$_3$ and brine. The organic layer was dried over Na$_2$SO$_4$ and the solvent was removed in vacuo. The residue was subjected to flash chromatography on silica gel (30% AcOEt/cyclohexane) to afford N-Boc-3-iodo-Tyr(Me)-NH-(Bn)Ala-OMe (165 mg, 66%) as a white amorphous solid. $^1$H NMR (300 MHz, CDCl$_3$) δ 1.31 (d, J=7.2 Hz, 3H, CH$_3$), 1.4 (s, 9H, (CH$_3$)$_3$), 2.76 (m, 2H, CH$_2$ Tyr), 3.62 (q, J=7.3 Hz, 1H, CH Ala), 3.66 (s, 3H, OCH$_3$), 3.79 (s, 3H, CH$_3$), 3.86 (m, 2H, CH$_2$ Bn), 4.1 (m, 1H, CH Tyr), 5.09 (m, 1H, NHBoc), 6.65 (d, J=8.4 Hz, 1H, H5), 7.02 (dd, J=8.4 Hz, J=2 Hz, 1H, H6), 7.22-7.33 (m, 5 aromatic H), 7.55 (d, J=2 Hz, 1H, H2), 7.48 (s, 1H, NH). $^{13}$C NMR (75 MHz, DMSO-d$_6$) δ 16.3 (CH$_3$), 28.3 ((CH$_3$)$_3$), 36.9 (CH$_2$ Tyr), 51.7 (OCH$_3$), 54.8 (CH Tyr), 56.4 (OCH$_3$), 59.9 (CH Ala), 60.2 (CH$_2$ Bn), 80.1 (C(CH$_3$)$_3$), 86 (C3), 110.9 (CH), 127.7 (CH), 128.3 (CH), 129.2 (CH), 130.4 (CH), 130.8 (C), 136.2 (C), 140.1 (CH), 155.2 (C4), 157.1 (CO Boc), 169.7 (CO amide), 174.4 (CO ester).

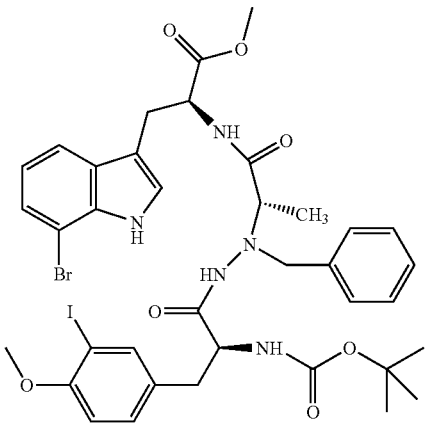

C₃₇H₄₀BrIN₅O₇
Mol. Wt.: 876.58

N-Boc-3-iodo-Tyr(Me)-NH-(Bn)Ala-7-bromo-Trp-OMe. To a solution of N-Boc-3-iodo-Tyr(Me)-NH-(Bn)Ala-OMe (135 mg, 0.22 mmol) in THF (3 mL) cooled at 0° C. was added a 1 M aqueous LiOH solution (0.25 mL). The mixture was stirred for 1 h 30 at 0° C. before it was quenched by 2 N aqueous HCl solution (pH=1-2). The aqueous phase was extracted twice by CH$_2$Cl$_2$, the combined organic layers were dried over Na$_2$SO$_4$. Removing of the solvents in vacuo afforded the crude N-Boc-3-iodo-Tyr(Me)-NH-(Bn)Ala-OH (121 mg, 92%) as a white foam which was used in the next step without further purification. To a suspension of 7-bromo-Trp-OMe (56 mg, 0.17 mmol), N-Boc-3-iodo-Tyr(Me)-NH-(Bn)Ala-OH (100 mg, 0.17 mmol), EDC (35 mg, 0.18 mmol) and HOBt (25 mg, 0.18 mmol) in CH$_2$Cl$_2$ (2 mL) was added NEt$_3$ (52 μL, 1.13 mmol) at 0° C. The resulting solution, allowed to warm up was stirred 2 h. The reaction mixture was diluted in AcOEt and washed successively with aqueous 5% KHSO$_4$, aqueous 0.5 M KHCO$_3$ and brine. The organic layer was dried over Na$_2$SO$_4$ and the solvent was removed in vacuo. The residue was subjected to flash chromatography on silica gel (5% MeOH/CH$_2$Cl$_2$) and precipitated in AcOEt/pentane to afford N-Boc-3-iodo-Tyr(Me)-NH-(Bn)Ala-7-bromo-Trp-OMe (77 mg, 52%) as a white amorphous solid. $^1$H NMR (300 MHz, CDCl$_3$) δ 1.17 (d, J=7 Hz, 3H, CH$_3$), 1.39 (s, 9H, (CH$_3$)$_3$), 2.49-2.69 (m, 2H, CH$_2$ Tyr), 3.22-3.32 (m, 2H, CH$_2$ Trp), 3.41-3.51 (m, 1H, CH Ala), 3.67 (s, 3H, OCH$_3$), 3.7-3.96 (m, 2H, CH$_2$ Bn), 3.8 (s, 3H, OCH$_3$), 3.97-4.08 (m, 1H, CH Tyr), 4.82-4.93 (m, 1H, CH Trp), 5.04 (d, J=8.2 Hz, 1H, NHBoc), 6.62 (d, J=8.2 Hz, 1H, H5 Tyr), 6.93 (dd, J=8.2 Hz, J=2 Hz, 1H, H6 Tyr), 6.99 (t, J=7.7 Hz, 1H, H5 Trp), 7.19-7.24 (m, 6 aromatic H), 7.32 (d, J=7.5, 1 aromatic H), 7.5 (d, J=2 Hz, 1H, H2 Tyr), 7.56 (d, J=7.9 Hz, 1 aromatic H), 7.71 (s, 1H, NH), 8.08 (s, 1H, NH), 8.65 (s, 1H, NH). $^{13}$C NMR (75 MHz, DMSO-d$_6$) δ 13.4 (CH$_3$), 27.6 (CH$_2$ Trp), 28.3 ((CH$_3$)$_3$), 36.1 (CH$_2$ Tyr), 52.5 (OCH$_3$), 54.8 (CH Tyr), 56.4 (OCH$_3$), 59.9 (CH$_2$ Bn), 62.6 (CH Tyr, CH Ala), 80.4 (C(CH$_3$)$_3$), 86 (C3), 104.8 (C7 Trp), 110.9 (CH), 111.7 (C), 118 (CH), 120.6 (CH), 123.8 (CH), 124.5 (CH), 127.8 (CH), 128.4 (CH), 128.7 (CH), 129.2 (CH), 130.3 (CH), 130.4 (C), 130.9 (CH), 131 (C), 134.8 (C), 135.7 (CH), 139.9 (CH), 155.6 (C4), 157 (CO Boc), 170.6, 172.6, 172.7 (2 CO amide, CO ester). Anal. Calcd. for $C_{37}H_{45}N_5O_7BrI$, $H_2O$: C, 49.56; H, 5.28; N, 7.81. Found: C, 49.83; H, 5.08; N, 7.57.

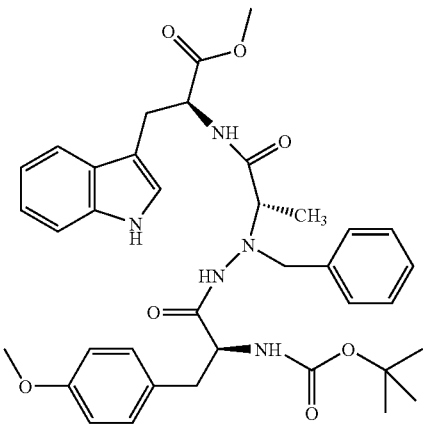

N-Boc-Tyr(Me)-NH-(Bn)Ala-Trp-OMe: Treatment of N-Boc-3-iodo-Tyr(Me)-NH-(Bn) Ala-7-bromo-Trp-OMe in the condition of the suzuki coupling according to Berthelot, A.; Piguel, S.; Le Dour, G.; Vidal, J., Synthesis of macrocyclic peptide analogues of proteasome inhibitor TMC-95A. J. Org. Chem. 2003, 68, (25), 9835-9838 afforded N-Boc-Tyr (Me)—NH(Bn)Ala-Trp-OMe. HRMS (ESI) calcd for $C_{37}H_{45}N_5O_7Na$ [(+Na)$^+$] 694.3217. Found 694.3197.

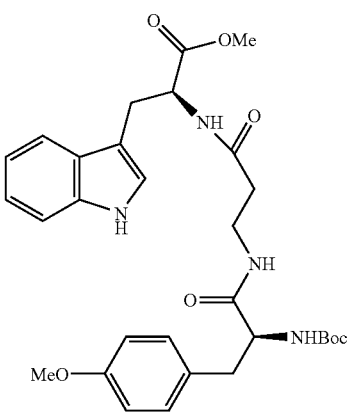

N-Boc-Tyr(Me)-βAla-Trp-OMe: Treatment of N-Boc-3-iodo-Tyr(Me)-βAla-7-bromo-Trp-OMe in the condition of the suzuki coupling according to Berthelot, A.; Piguel, S.; Le Dour, G.; Vidal, J., Synthesis of macrocyclic peptide analogues of proteasome inhibitor TMC-95A. J. Org. Chem. 2003, 68, (25), 9835-9838 afforded N-Boc-Tyr(Me)-βAla-Trp-OMe. HRMS (ESI) calcd for $C_{30}H_{38}N_4O_7Na$ [(M+Na)$^+$] 589.2638. Found 589.2634.

VIII) Enzymatic Evaluation

Proteasome:
20S proteasome from rabbit reticulocyte was from commercial source (Alexis Biochemicals)

Enzymatic Analysis of Inhibition
Semi-automatic fluorescent assays using Suc-LLVY-amc (SEQ ID NO: 2) for chymotrypsin-like activity, Z-LLE-SNA for post-acid activity and Boc-LLR-amc for trypsin-like activity of proteasome were performed at pH 7.5 and 30° C. using BMG Fluostar microplate reader (Suc=succinyl; amc=7-amino-4-methylcoumarin; Z=benzyloxycarbonyl; NA=2-naphtylamine; Boc=tert-butoxycarbonyl). The buffers were: 20 mM Tris, 1 mM DTT, 10% glycerol, 3% (v/v) DMSO (ChT-L and PA activities); 20 mM Tris, 1 mM DTT, 10% glycerol, 3% (v/v) DMSO. Studied compounds were dissolved in DMSO prior dissolution in the buffer. Proteasome was incubated for 15 min at 30° C. in the presence of the studied compound (0.1-100 μM). A control assay in the absence of tested compounds contained DMSO at the same concentration (3%, v/v). The fluorogenic proteasome substrate was then added and the hydrolysis of the appropriate fluorescent substrate was monitored for 1 h ($\lambda_{exc}$=360, $\lambda_{em}$=465 nm for amc substrates and $\lambda_{exc}$=340, $\lambda_{em}$=405 nm for the βNA substrate). Initial rates determined in control experiments were considered to be 100% of the peptidasic activity; initial rates that were above 100% in the presence of a test compound were considered to be activations, while initial rates below 100% were considered to be inhibitions. For weak inhibitors, the percentage of inhibition at a reference concentration (100 μM) is reported. The results, expressed in % inhibition (or activation factor), were obtained by calculating the average of at least two independent experiments, the variability was less than 10%. The inhibitory activity of more efficient compounds are expressed as $IC_{50}$ calculated by fitting the experimental data to the equation 1: % Inhibition=100 $[I]_0/(IC_{50}+[I]_0)$=100 $(v_0-v_i/v_0)$, or equation 2: % Inhibition=100 $[I]_0^{nH}/(IC_{50}^{nH}+[I]_0^{nH})$, nH is the Hill number. $v_0$ and $v_i$ are the initial rates in the absence and in the presence of inhibitor. A Dixon plot has been used to determine the inhibition constant $K_i$ for competitive inhibition by compound A215. The reversible character of inhibition or activation was determined by measuring the activity of treated enzyme after the inhibitor molecule has been withdrawn from the reaction medium.

Results:
Inhibition of Rabbit 20 S Proteasome (pH=7.5, 30° C.)

|  | CT-L % inhibition (at 100 μM) or $IC_{50}$ | PA % inhibition (at 100 μM) or $IC_{50}$ | T-L % inhibition (at 100 μM) or $IC_{50}$ |
|---|---|---|---|
| Compounds II |  |  |  |
| A374F1 | ni | 18% |  |
| A291 | ni | 19% |  |
| A389F1pI2 | ni | 55% | ni |
| Compounds III |  |  |  |
| SP221 | ni | ni |  |
| SP225F2 |  | 25% | 49% |
| SP226F1 | ni | ni | 23% |
| Compounds IV-1A |  |  |  |
| A248 | ni | 32% | ni |
| A215 | $IC_{50}$ = 6.8 μM ($K_i$ = 2 μM) | $IC_{50}$ = 11.3 μM | $IC_{50}$ = 14.4 μM |
| SP274 | 62% | 45% | ni |
| A363 | ni | 20% |  |
| A340 | ni | 17% | ni |
| A174 | ni | ni | ni |
| A268 | ni | ni |  |
| A385 | 28% | 38% | ni |
| A254 | 38% | 60% | ni |
| Compounds IV-2 |  |  |  |
| PSV11R |  | 59% |  |
| NR35 | ni | ni |  |
| SP303r2 |  |  |  |

-continued

| | CT-L % inhibition (at 100 μM) or IC$_{50}$ | PA % inhibition (at 100 μM) or IC$_{50}$ | T-L % inhibition (at 100 μM) or IC$_{50}$ |
|---|---|---|---|
| SP304R | ni | 45% | |
| SP313P | 26% | IC$_{50}$ = 4 μM | ni |
| NR36 | 34% | 39% | |
| NR40 | IC$_{50}$ = 40 μM | IC$_{50}$ = 35 μM | |
| A424P | | ni | |
| A414P | | ni | |
| A418P | ni | 32% | |
| SP296P | 22% | 59% | |
| SP314C2 | | ni | |
| A416 | 28% | 35% | |
| SP318C | 15% | 66% | |
| SP325 | IC$_{50}$ = 5.4 μM | IC$_{50}$ = 2.5 μM | IC$_{50}$ = 19 μM |
| SP324 | IC$_{50}$ = 9 μM | IC$_{50}$ = 3 μM | IC$_{50}$ = 21 μM |
| SP310C | | ni | |
| SP315C2 | | ni | |
| SP320P2 | ni | ni | ni |
| SP306P | | ni | |
| SP307P | | ni | |
| SP319P | 36% | ni | 14% |
| SP308P | | ni | |
| Compounds IV-3 | | | |
| CV11 | ni | ni | |
| CV12 | ni | IC$_{50}$ = 10.4 μM | |
| CV13 | 32% | IC$_{50}$ = 3.9 μM | ni |
| JV602 | 22% | 26% | |
| NR15 | IC$_{50}$ = 2.2 μM | 87% | |
| NR38 | IC$_{50}$ = 13.5 μM | 81% | |
| NR16 | 12% | ni | |
| Compound IV-1B | | | |
| A493 | 29% | 40% | | ni: non inhibitor

Activation of Rabbit 20 S Proteasome (pH=7.5, 30° C., [Compound]=100 μM)

| | CT-L Activation factor | PA Activation factor | T-L Activation factor |
|---|---|---|---|
| Compounds II | | | |
| A374F1 | | | 1.8 |
| A291 | | | 1.4 |
| Compounds III | | | |
| SP221 | | | 1.4 |
| Compounds IV-1A | | | |
| A363 | | | 1.9 |
| A268 | | | 2 |

-continued

| | CT-L Activation factor | PA Activation factor | T-L Activation factor |
|---|---|---|---|
| Compounds IV-2 | | | |
| PSV11R | 1.2 | | 1.7 |
| NR35 | | | 1.8 |
| SP303r2 | 1.4 | | 1.6 |
| SP304R | | | 1.7 |
| SP305R | 1.5 | 1.2 | 3.2 |
| NR36 | | | 9.8 |
| NR40 | | | 6 |
| A424P | 1.2 | | 1.9 |
| A414P | 1.3 | | 1.9 |
| A418P | | | 1.6 |
| SP296P | | | 2.3 |
| SP314C2 | 1.5 | | 2.5 |
| A416 | | | 2.2 |
| SP318C | | | 1.2 |
| SP323C2 | 1.6 | 1.2 | 2.2 |
| SP310C | 1.7 | | 1.6 |
| SP315C2 | 1.2 | | 1.9 |
| SP311C | 1.3 | 1.2 | 1.9 |
| SP306P | 1.2 | | 1.6 |
| SP307P | 1.3 | | 1.8 |
| SP308P | 1.6 | | 1.9 |
| Compounds IV-3 | | | |
| CV11 | | | 1.7 |
| CV12 | | | 1.5 |
| JV602 | | | 1.3 |
| NR15 | | | 12.3 |
| NR38 | | | 9.8 |
| NR16 | | | 8.2 |
| Compound IV-1B | | | |
| A493 | | | 8.2 |

FIGURE LEGENDS

SEQUENCE LISTING

<160> NUMBER OF SEQ ID NOS: 2

Figure 1:
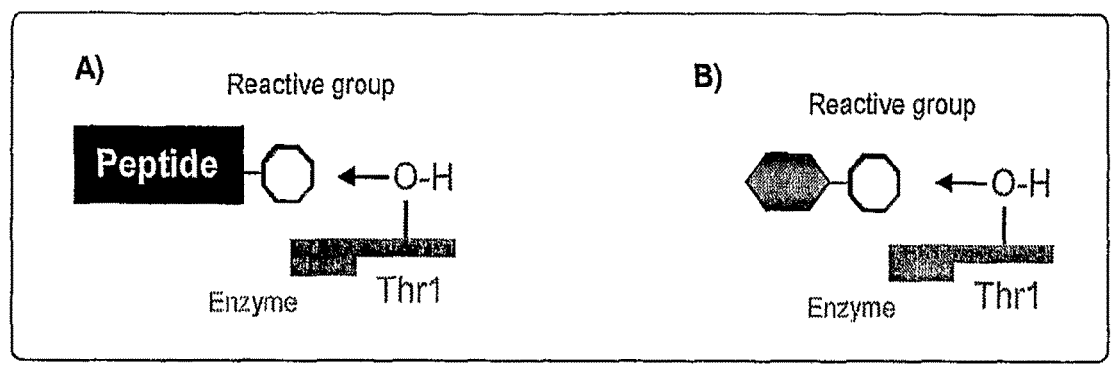
FIG. 1. Schematic representation of the reaction of: (A) peptidic inhibitors (aldehydes, boronates, vinylsulfones), and (B) non peptidic inhibitors such as clastolactacystin-β-lactone, (−)epigallocatechin-3-gallate with the catalytic Thr1 of the active sites of proteasome. Adducts (A) or stable acyl-enzymes (B) are obtained after the formation of a covalent bond between Thr1 and the reactive group of the inhibitor.
Figure 2A:
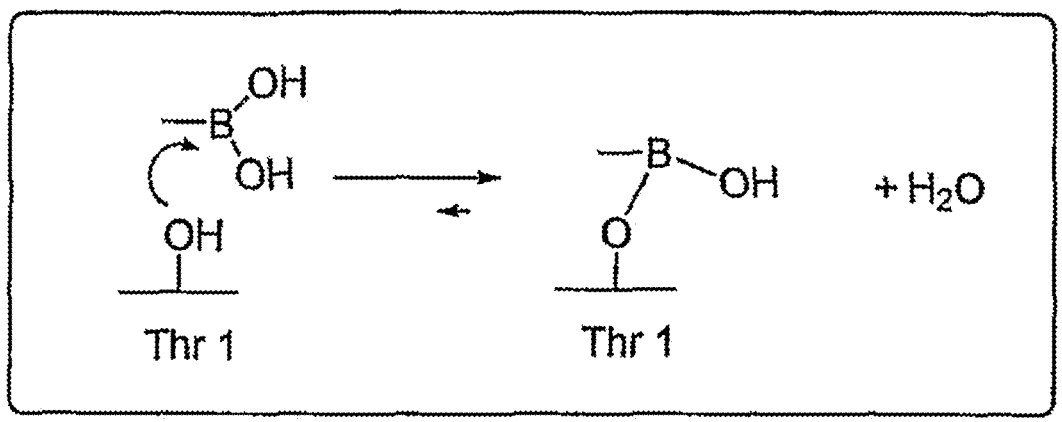
FIG. 2A: Mechanism of inhibition of proteasome by Velcade
Figure 2B:
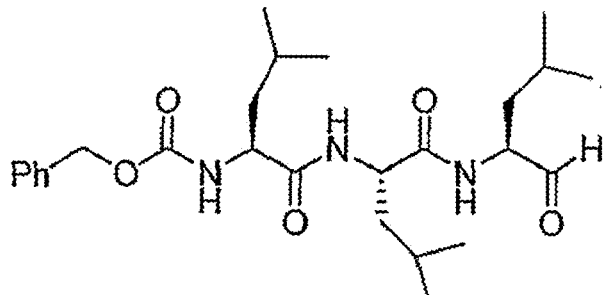
FIG. 2B: Structures of proteasome inhibitors
Figure 2B:
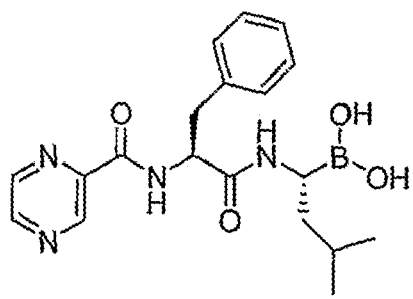
Figure 2B:
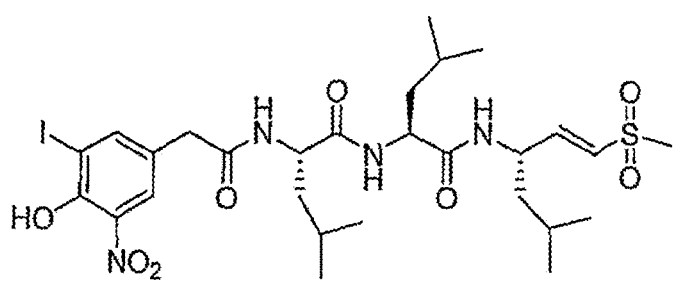
Figure 2B:
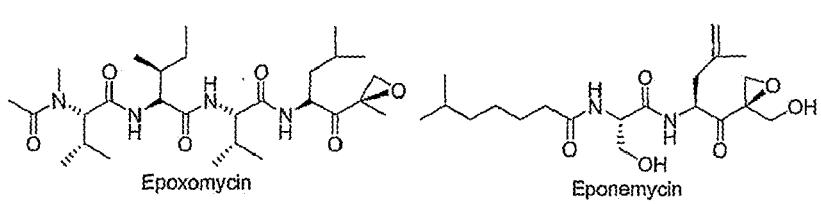
Figure 2B:
Figure 2B:
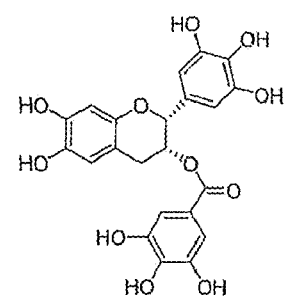
Figure 2B:
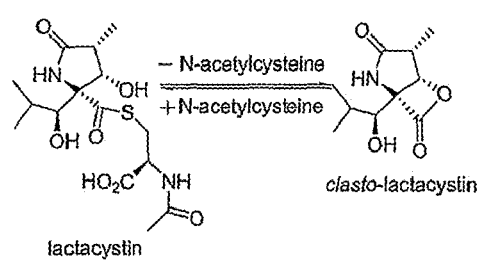
Figure 3:
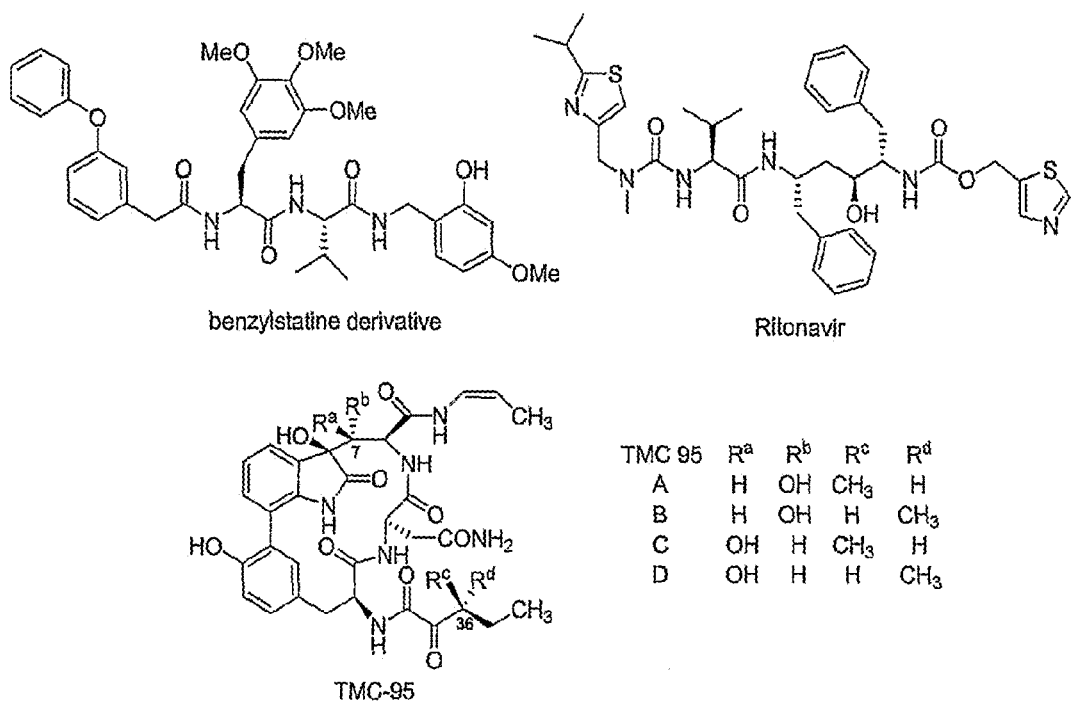
FIG. 3: Structures of known non covalent inhibitors of proteasome

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Modified at N-terminus by benzyloxycarbonyl

```
        group (Z)
<220> FEATURE:
<221> NAME/KEY: MISC_FEATURE
<222> LOCATION: (2)..(2)
<223> OTHER INFORMATION: Modified by terbutyl group (OtBu)
<220> FEATURE:
<221> NAME/KEY: MISC_FEATURE
<222> LOCATION: (4)..(4)
<223> OTHER INFORMATION: COOH is COH (Leucinal)

<400> SEQUENCE: 1

Ile Glu Ala Leu
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Modified at N-terminus by succinyl group (Suc)
<220> FEATURE:
<221> NAME/KEY: MISC_FEATURE
<222> LOCATION: (4)..(4)
<223> OTHER INFORMATION: Modified at C-terminus by
      7-amino-4-methylcoumarin group (amc)

<400> SEQUENCE: 2

Leu Leu Val Tyr
1
```

The invention claimed is:

1. A method for treating diseases wherein a proteasome is involved, comprising administering to a human or animal organism in need thereof an effective amount of a compound represented by the following general formula (IV):

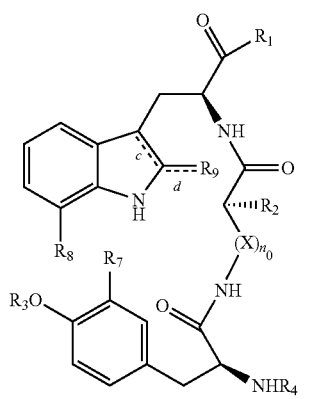

wherein, only one of the bonds c or d is present, provided that:

when the bond c is present and d is absent, then $R_9$ is H;

when the bond d is present and c is absent, then $R_9$ is an oxygen atom O;

$n_0$ is 0 or 1, and when $n_0$ is 1, $X=CH_2$ or $NCH_2C_6H_5$;

$R_1$ is

OH, or a $OR_{10}$ group in which $R_{10}$ is a linear or branched alkyl group of from 1 to 5 carbon atoms, or a group of formula $NH-(CH_2)_{n_1}-R_{11}$ in which $n_1=0$ or an integer from 1 to 5, $R_{11}$ is a linear or branched alkyl group of from 1 to 5 carbon atoms, an aryl group, wherein said alkyl group or said aryl group is optionally substituted, $NH_2$, or $NHR_{12}$ in which $R_{12}$ is a protecting group of amine functions;

$R_2$ is

H, or a linear or branched alkyl group of from 1 to 5 carbon atoms, or a group of formula $(CH_2)_{n_2}-(CO)_{n_3}-NR_{13}R_{14}$, in which $n_2$ is an integer from 1 to 5, $n_3=0$ or 1, $R_{13}$ and $R_{14}$, independently from one another, are H, a protecting group of amine functions or a group of formula $C(=NH)NHR_{15}$ in which $R_{15}$ is H, a protecting group of amine functions or a side chain from proteinogenic amino acids;

$R_3$ is H, or a linear or branched alkyl group of from 1 to 5 carbon atoms, optionally substituted with an aryl group;

$R_4$ is a protecting group of amine functions; and $R_7$ and $R_8$, independently from one another, are H or a halogen atom.

2. The method according to claim 1, wherein the compound to be administered is represented by the following formula (IV-1):

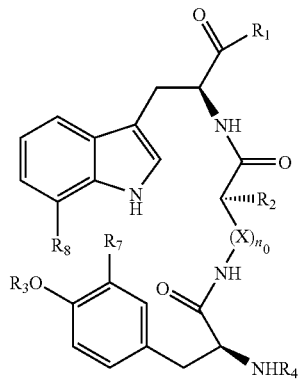

(IV-1)

corresponding to a compound represented by the formula (IV) in which:

the bond c is present, and $R_9$ is H;

$n_0$=0 or 1;

X=$CH_2$ or $NCH_2C_6H_5$;

$R_1$ is OH, or a group $OR_{10}$ in which $R_{10}$ is a linear or branched alkyl group of from 1 to 5 carbon atoms, or a group of formula NH—$(CH_2)_{n1}$—$R_{11}$ in which $n_1$=0 and $R_{11}$ is a linear or branched alkyl group of from 1 to 5 carbon atoms;

$R_2$ is H, a linear or branched alkyl group of from 1 to 5 carbon atoms, or a group of formula $(CH_2)_{n2}$—$(CO)_{n3}$—$NR_{13}R_{14}$, in which $n_2$=1 to 5, $n_3$=1, and $R_{13}$=$R_{14}$=H;

$R_3$ is a linear or branched alkyl group of from 1 to 5 carbon atoms, optionally substituted with an aryl group;

$R_4$ is a protecting group of amine functions; and $R_7$ and $R_8$, independently from one another, are a halogen atom.

3. The method according to claim 2, wherein the compound to be administered is represented by the formula (IV-1) in which:

$R_1$ is OH, $OCH_3$, $OCH_2CH_3$, or $NHCH_3$;

$R_2$ is H, $CH_3$, $CH_2$—$CH(CH_3)_2$, or $CH_2CONH_2$;

$R_3$ is $CH_3$, or $CH_2$—$C_6H_5$;

$R_4$ is Boc;

$R_7$ is I; and $R_8$ is Br.

4. The method according to claim 3, wherein the compound to be administered is represented by the following formula (IV-1a):

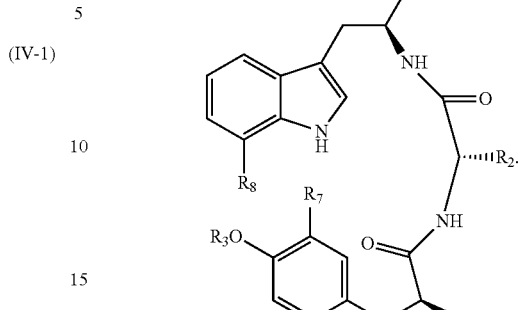

(IV-1a)

5. The method according to claim 4, wherein the compound to be administered is represented by the formula (IV-1a) in which:

$R_1$ is $OCH_3$, $R_2$ is $CH_3$, $R_3$ is $CH_2$—$C_6H_5$, $R_4$ is Boc, $R_7$ is I, and $R_8$ is Br (compound A248); or $R_1$ is OH, $R_2$ is $CH_3$, $R_3$ is $CH_2$—$C_6H_5$, $R_4$ is Boc, $R_7$ is I, and $R_8$ is Br (compound A215); or $R_1$ is $OCH_3$, $R_2$ is $CH_2CONH_2$, $R_3$ is $CH_2$—$C_6H_5$, $R_4$ is Boc, $R_7$ is I, and $R_8$ is Br (compound SP274); or $R_1$ is $OCH_3$, $R_2$ is $CH_2$—$CH(CH_3)_2$, $R_3$ is $CH_3$, $R_4$ is Boc, $R_7$ is I, and $R_8$ is Br (compound A363); or $R_1$ is $OCH_2CH_3$, $R_2$ is $CH_2$—$CH(CH_3)_2$, $R_3$ is $CH_3$, $R_4$ is Boc, $R_7$ is I, and $R_8$ is Br (compound A340); or $R_1$ is $OCH_2CH_3$, $R_2$ is $CH_2$—$CH(CH_3)_2$, $R_3$ is $CH_2$—$C_6H_5$, $R_4$ is Boc, $R_7$ is I, and $R_8$ is Br (compound A174); or $R_1$ is $OCH_3$, $R_2$ is $CH_2$—$CH(CH_3)_2$, $R_3$ is $CH_2$—$C_6H_5$, $R_4$ is Boc, $R_7$ is I, and $R_8$ is Br (compound A268); or $R_1$ is $OCH_3$, $R_2$ is $CH_3$, $R_3$ is $CH_3$, $R_4$ is Boc, $R_7$ is I, and $R_8$ is Br (compound A385); or $R_1$ is $NHCH_3$, $R_2$ is $CH_3$, $R_3$ is $CH_2$—$C_6H_5$, $R_4$ is Boc, $R_7$ is I, and $R_8$ is Br (compound A254).

6. The method according to claim 1, wherein in $R_{12}$ the protecting group of amine functions is tertiobutyloxycarbonyl (Boc) or CO—O—$CH_2$—$C_6H_5$ (Z).

7. The method according to claim 1, wherein in $R_{13}$ and $R_{14}$ the protecting group of amine functions is tertiobutyloxycarbonyl (Boc) or CO—O—$CH_2$—$C_6H_5$ (Z).

8. The method according to claim 1, wherein in $R_{15}$ the protecting group of amine functions is tertiobutyloxycarbonyl (Boc) or CO—O—$CH_2$—$C_6H_5$ (Z).

9. The method according to claim 1, wherein in $R_4$ the protecting group of amine functions is tertiobutyloxycarbonyl (Boc) or CO—O—$CH_2$—$C_6H_5$ (Z).

10. The method according to claim 1, wherein in $R_7$ and $R_8$ the halogen atom is Br, I or Cl.

11. The method according to claim 2, wherein in $R_4$ the protecting group of amine functions is tertiobutyloxycarbonyl (Boc).

12. The method according to claim 2, wherein in $R_7$ and $R_8$ the halogen atom is Br or I.

* * * * *